US009096636B2

(12) United States Patent
Crooke

(10) Patent No.: US 9,096,636 B2
(45) Date of Patent: *Aug. 4, 2015

(54) CHIMERIC OLIGOMERIC COMPOUNDS AND THEIR USE IN GENE MODULATION

(75) Inventor: Stanley T. Crooke, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 3052 days.

This patent is subject to a terminal disclaimer.

(21) Appl. No.: 10/701,265

(22) Filed: Nov. 4, 2003

(65) Prior Publication Data

US 2004/0147023 A1  Jul. 29, 2004

Related U.S. Application Data

(60) Continuation-in-part of application No. 10/078,949, filed on Feb. 20, 2002, now Pat. No. 7,695,902, which is a continuation of application No. 09/479,783, filed on Jan. 7, 2000, now abandoned, which is a division of application No. 08/870,608, filed on Jun. 6, 1997, now Pat. No. 6,107,094, which is a continuation-in-part of application No. 08/659,440, filed on Jun. 6, 1996, now Pat. No. 5,898,031.

(60) Provisional application No. 60/423,760, filed on Nov. 5, 2002, provisional application No. 60/503,271, filed on Sep. 15, 2003.

(51) Int. Cl.
C07H 21/02 (2006.01)
C07H 21/04 (2006.01)
C12N 15/11 (2006.01)

(52) U.S. Cl.
CPC ............... C07H 21/02 (2013.01); C07H 21/04 (2013.01); C12N 15/111 (2013.01); C12N 2310/11 (2013.01); C12N 2310/14 (2013.01); C12N 2310/315 (2013.01); C12N 2310/321 (2013.01); C12N 2310/322 (2013.01); C12N 2310/341 (2013.01); C12N 2310/342 (2013.01); C12N 2310/346 (2013.01); C12N 2320/51 (2013.01)

(58) Field of Classification Search
CPC combination set(s) only.
See application file for complete search history.

(56) References Cited

U.S. PATENT DOCUMENTS

| 3,687,808 | A | 8/1972 | Merigan et al. ............... 195/28 |
| 4,373,071 | A | 2/1983 | Itakura ........................... 525/375 |
| 4,381,344 | A | 4/1983 | Rideout et al. |
| 4,401,796 | A | 8/1983 | Itakura ........................... 525/340 |
| 4,415,732 | A | 11/1983 | Caruthers et al. |
| 4,426,330 | A | 1/1984 | Sears |
| 4,458,066 | A | 7/1984 | Caruthers et al. |
| 4,469,863 | A | 9/1984 | Ts'o et al. ...................... 536/27 |
| 4,476,301 | A | 10/1984 | Imbach et al. |
| 4,500,707 | A | 2/1985 | Caruthers et al. |
| 4,507,433 | A | 3/1985 | Miller et al. ............... 525/54.11 |
| 4,511,713 | A | 4/1985 | Miller et al. |
| 4,534,899 | A | 8/1985 | Sears |
| 4,587,044 | A | 5/1986 | Miller |
| 4,605,735 | A | 8/1986 | Miyoshi |
| 4,667,025 | A | 5/1987 | Miyoshi |
| 4,668,777 | A | 5/1987 | Caruthers et al. |
| 4,689,320 | A | 8/1987 | Kaji |
| 4,720,483 | A | 1/1988 | Jansz et al. |
| 4,725,677 | A | 2/1988 | Koster et al. |
| 4,757,141 | A | 7/1988 | Fung et al. |
| 4,760,017 | A | 7/1988 | McCormick |
| 4,762,779 | A | 8/1988 | Snitman |
| 4,789,737 | A | 12/1988 | Miyoshi |
| 4,812,512 | A | 3/1989 | Buendia et al. ............ 525/54.11 |
| 4,824,941 | A | 4/1989 | Gordon |
| 4,828,979 | A | 5/1989 | Klevan |
| 4,835,263 | A | 5/1989 | Nguyen |
| 4,845,205 | A | 7/1989 | Huynh Dinh et al. |
| 4,849,320 | A | 7/1989 | Irving et al. |
| 4,849,513 | A | 7/1989 | Smith et al. |
| 4,876,335 | A | 10/1989 | Yamane |
| 4,904,582 | A | 2/1990 | Tullis |
| 4,908,405 | A | 3/1990 | Bayer et al. ...................... 525/61 |
| 4,924,624 | A | 5/1990 | Suhadolnik et al. |
| 4,948,882 | A | 8/1990 | Ruth |
| 4,958,013 | A | 9/1990 | Letsinger |

(Continued)

FOREIGN PATENT DOCUMENTS

CA  2017369 C   1/2001
DE  3915432 A1  11/1990

(Continued)

OTHER PUBLICATIONS

Lee, et al. (1993) The *C. elegans* Heterochronic Gene Lin-4 Encodes Small RNAs With Antisense Complementarity to Lin-14. Cell, v.75:843-54.*

(Continued)

*Primary Examiner* — Jennifer McDonald

(74) *Attorney, Agent, or Firm* — Isis Pharmaceuticals, Inc. Patent Dept.

(57) ABSTRACT

Oligomer compositions comprising first and second oligomers are provided wherein at least a portion of the first oligomer is capable of hybridizing with at least a portion of the second oligomer, at least a portion of the first oligomer is complementary to and capble of hybridizing to a selected target nucleic acid, and at least one of the first or second oligomers includes at least one nucleotide comprising a chimeric organic composition. Oligomer/protein compositions are also provided comprising an oligomer complementary to and capable of hybridizing to a selected target nucleic acid and at least one protein comprising at least a portion of an RNA-induced silencing complex (RISC), wherein at least one nucleotide comprising a chimeric organic composition.

7 Claims, No Drawings

(56) References Cited

U.S. PATENT DOCUMENTS

| | | |
|---|---|---|
| 4,965,350 A | 10/1990 | Inoue et al. |
| 4,973,679 A | 11/1990 | Caruthers et al. |
| 4,981,957 A | 1/1991 | Lebleu |
| 5,000,000 A | 3/1991 | Ingram et al. |
| 5,013,556 A | 5/1991 | Woodle et al. |
| 5,013,830 A | 5/1991 | Ohtsuka et al. ................. 536/27 |
| 5,023,243 A | 6/1991 | Tullis ............................. 514/44 |
| 5,034,506 A | 7/1991 | Summerton et al. .......... 528/391 |
| 5,082,830 A | 1/1992 | Brakel |
| 5,082,934 A | 1/1992 | Saba et al. |
| 5,108,921 A | 4/1992 | Low et al. |
| 5,109,124 A | 4/1992 | Ramathandran |
| 5,112,963 A | 5/1992 | Pieles |
| 5,118,800 A | 6/1992 | Fung |
| 5,118,802 A | 6/1992 | Smith |
| 5,130,302 A | 7/1992 | Spielvogel et al. ............. 514/45 |
| 5,132,418 A | 7/1992 | Caruthers et al. |
| 5,134,066 A | 7/1992 | Rogers et al. |
| 5,138,045 A | 8/1992 | Cook |
| 5,142,047 A | 8/1992 | Summerton et al. ........... 514/44 |
| RE34,069 E | 9/1992 | Koster et al. |
| 5,149,782 A | 9/1992 | Chang et al. |
| 5,149,797 A | 9/1992 | Pederson et al. ................ 536/27 |
| 5,151,510 A | 9/1992 | Stec et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. ............. 514/45 |
| 5,185,444 A | 2/1993 | Summerton et al. |
| 5,188,897 A | 2/1993 | Suhadolnik et al. |
| 5,194,599 A | 3/1993 | Froehler et al. |
| 5,212,295 A | 5/1993 | Cook |
| 5,213,804 A | 5/1993 | Martin et al. |
| 5,214,134 A | 5/1993 | Weis et al. |
| 5,214,135 A | 5/1993 | Srivastava et al. |
| 5,214,136 A | 5/1993 | Lin |
| 5,216,141 A | 6/1993 | Benner |
| 5,218,105 A | 6/1993 | Cook |
| 5,220,007 A | 6/1993 | Pederson et al. ............. 536/23.1 |
| 5,223,618 A | 6/1993 | Cook et al. .................... 544/276 |
| 5,227,170 A | 7/1993 | Sullivan |
| 5,235,033 A | 8/1993 | Summerton et al. .......... 528/391 |
| 5,245,022 A | 9/1993 | Weis |
| 5,254,469 A | 10/1993 | Warren |
| 5,256,775 A | 10/1993 | Froehler ...................... 536/25.6 |
| 5,258,506 A | 11/1993 | Urdea |
| 5,262,536 A | 11/1993 | Hobbs |
| 5,264,221 A | 11/1993 | Tagawa et al. |
| 5,264,423 A | 11/1993 | Cohen et al. |
| 5,264,562 A | 11/1993 | Matteucci .................... 536/23.1 |
| 5,264,564 A | 11/1993 | Matteucci .................... 536/23.1 |
| 5,272,250 A | 12/1993 | Spielvogel |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita |
| 5,317,098 A | 5/1994 | Shizuya |
| 5,319,080 A | 6/1994 | Leumann |
| 5,321,131 A | 6/1994 | Agrawal et al. |
| 5,354,844 A | 10/1994 | Beug et al. |
| 5,356,633 A | 10/1994 | Woodle et al. |
| 5,359,044 A | 10/1994 | Cook et al. ................... 536/23.1 |
| 5,366,878 A | 11/1994 | Pederson et al. ............. 435/91.3 |
| 5,367,066 A | 11/1994 | Urdea et al. |
| 5,371,241 A | 12/1994 | Brush |
| 5,378,825 A | 1/1995 | Cook et al. .................. 536/25.34 |
| 5,386,023 A | 1/1995 | Sanghvi et al. ............... 536/25.3 |
| 5,391,667 A | 2/1995 | Dellinger .................... 526/264 |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler et al. |
| 5,403,711 A | 4/1995 | Walder et al. ..................... 435/6 |
| 5,405,938 A | 4/1995 | Summerton et al. |
| 5,405,939 A | 4/1995 | Suhadolnik et al. |
| 5,414,077 A | 5/1995 | Lin |
| 5,416,016 A | 5/1995 | Low et al. |
| 5,416,203 A | 5/1995 | Letsinger |
| 5,417,978 A | 5/1995 | Tari et al. |
| 5,424,413 A | 6/1995 | Hogan et al. |
| 5,432,272 A | 7/1995 | Benner |
| 5,434,257 A | 7/1995 | Matteucci et al. |
| 5,446,137 A | 8/1995 | Maag |
| 5,451,463 A | 9/1995 | Nelson |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,191 A | 10/1995 | Cook et al. .................. 536/27.13 |
| 5,459,127 A | 10/1995 | Felgner et al. |
| 5,459,255 A | 10/1995 | Cook et al. .................. 536/27.13 |
| 5,462,854 A | 10/1995 | Coassin et al. |
| 5,466,677 A | 11/1995 | Baxter et al. |
| 5,466,786 A | 11/1995 | Buhr et al. .................. 536/26.26 |
| 5,469,854 A | 11/1995 | Unger et al. |
| 5,470,967 A | 11/1995 | Huie et al. |
| 5,476,925 A | 12/1995 | Letsinger et al. ............. 536/23.1 |
| 5,484,908 A | 1/1996 | Froehler et al. ............. 536/24.31 |
| 5,486,603 A | 1/1996 | Buhr |
| 5,489,677 A | 2/1996 | Sanghvi et al. ............... 536/22.1 |
| 5,491,133 A | 2/1996 | Walder et al. ..................... 514/44 |
| 5,502,177 A | 3/1996 | Matteucci et al. |
| 5,506,212 A | 4/1996 | Hoke et al. |
| 5,506,337 A | 4/1996 | Summerton et al. .......... 528/391 |
| 5,506,351 A | 4/1996 | McGee ........................ 536/55.3 |
| 5,508,270 A | 4/1996 | Baxter et al. ..................... 514/47 |
| 5,510,475 A | 4/1996 | Agrawal |
| 5,512,295 A | 4/1996 | Kornberg et al. |
| 5,512,439 A | 4/1996 | Hornes |
| 5,512,667 A | 4/1996 | Reed |
| 5,514,785 A | 5/1996 | Van Ness |
| 5,514,786 A | 5/1996 | Cook et al. |
| 5,519,126 A | 5/1996 | Hecht |
| 5,519,134 A | 5/1996 | Acevedo et al. ............... 544/243 |
| 5,521,291 A | 5/1996 | Curiel et al. |
| 5,525,465 A | 6/1996 | Haralambidis |
| 5,525,711 A | 6/1996 | Hawkins et al. |
| 5,527,528 A | 6/1996 | Allen et al. |
| 5,527,899 A | 6/1996 | Froehler |
| 5,532,130 A | 7/1996 | Alul |
| 5,534,259 A | 7/1996 | Zalipsky et al. |
| 5,536,821 A | 7/1996 | Agrawal et al. |
| 5,539,082 A | 7/1996 | Nielsen et al. |
| 5,539,083 A | 7/1996 | Cook et al. .................... 530/333 |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea |
| 5,547,932 A | 8/1996 | Curiel et al. |
| 5,550,111 A | 8/1996 | Suhadolnik et al. |
| 5,552,538 A | 9/1996 | Urdea |
| 5,552,540 A | 9/1996 | Haralambidis |
| 5,556,948 A | 9/1996 | Tagawa et al. |
| 5,561,043 A | 10/1996 | Cantor et al. |
| 5,561,225 A | 10/1996 | Maddry et al. |
| 5,563,253 A | 10/1996 | Agrawal et al. |
| 5,565,350 A | 10/1996 | Kmiec ........................ 435/172.3 |
| 5,565,552 A | 10/1996 | Magda |
| 5,565,555 A | 10/1996 | Froehler et al. |
| 5,567,810 A | 10/1996 | Weis |
| 5,567,811 A | 10/1996 | Mistura et al. .............. 536/25.34 |
| 5,571,799 A | 11/1996 | Tkachuk et al. |
| 5,574,142 A | 11/1996 | Meyer |
| 5,576,302 A | 11/1996 | Cook et al. |
| 5,576,427 A | 11/1996 | Cook et al. .................... 536/23.1 |
| 5,578,717 A | 11/1996 | Urdea |
| 5,578,718 A | 11/1996 | Cook |
| 5,580,575 A | 12/1996 | Unger et al. |
| 5,580,731 A | 12/1996 | Chang |
| 5,582,188 A | 12/1996 | Benderev et al. |
| 5,583,020 A | 12/1996 | Sullivan |
| 5,585,481 A | 12/1996 | Arnold |
| 5,587,361 A | 12/1996 | Cook et al. |

(56) References Cited

U.S. PATENT DOCUMENTS

| | | |
|---|---|---|
| 5,587,371 A | 12/1996 | Sessler |
| 5,587,469 A | 12/1996 | Cook et al. |
| 5,591,584 A | 1/1997 | Chang |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda |
| 5,595,756 A | 1/1997 | Bally et al. |
| 5,596,086 A | 1/1997 | Matteucci et al. |
| 5,596,091 A | 1/1997 | Switzer et al. |
| 5,597,696 A | 1/1997 | Linn |
| 5,597,909 A | 1/1997 | Urdea |
| 5,599,797 A | 2/1997 | Cook et al. |
| 5,599,923 A | 2/1997 | Sessler |
| 5,599,925 A | 2/1997 | Torii |
| 5,599,928 A | 2/1997 | Hemmi et al. |
| 5,602,240 A | 2/1997 | De Mesmaeker et al. ... 536/22.1 |
| 5,607,922 A | 3/1997 | De Clercq et al. ............ 514/43 |
| 5,607,923 A | 3/1997 | Cook et al. |
| 5,608,046 A | 3/1997 | Cook |
| 5,610,289 A | 3/1997 | Cook et al. |
| 5,610,300 A | 3/1997 | Altmann |
| 5,612,469 A | 3/1997 | Goodchild |
| 5,614,617 A | 3/1997 | Cook et al. .................. 536/23.1 |
| 5,614,621 A | 3/1997 | Ravikumar et al. |
| 5,618,704 A | 4/1997 | Sanghvi et al. |
| 5,623,065 A | 4/1997 | Cook et al. .................. 536/23.1 |
| 5,623,070 A | 4/1997 | Cook et al. |
| 5,625,050 A | 4/1997 | Beaton et al. |
| 5,627,053 A | 5/1997 | Usman |
| 5,631,148 A | 5/1997 | Urdea |
| 5,633,360 A | 5/1997 | Bischofberger et al. |
| 5,634,488 A | 6/1997 | Martin, Jr. |
| 5,635,488 A | 6/1997 | Cook et al. |
| 5,639,647 A | 6/1997 | Usman et al. |
| 5,639,873 A | 6/1997 | Barascut et al. ............. 536/25.3 |
| 5,643,889 A | 7/1997 | Suhadolnik et al. |
| 5,645,985 A | 7/1997 | Froehler et al. |
| 5,646,265 A | 7/1997 | Mcgee |
| 5,646,269 A | 7/1997 | Matteucci et al. |
| 5,652,355 A | 7/1997 | Metelev et al. .............. 536/24.5 |
| 5,652,356 A | 7/1997 | Agrawal ......................... 536/245 |
| 5,658,731 A | 8/1997 | Sproat et al. |
| 5,658,873 A | 8/1997 | Bertsch-Frank |
| 5,661,134 A | 8/1997 | Cook et al. |
| 5,663,312 A | 9/1997 | Chaturvedula |
| 5,663,360 A | 9/1997 | Bortolaso et al. |
| 5,670,633 A | 9/1997 | Cook et al. |
| 5,672,662 A | 9/1997 | Harris et al. |
| 5,672,695 A | 9/1997 | Eckstein et al. |
| 5,672,697 A | 9/1997 | Buhr et al. |
| 5,677,289 A | 10/1997 | Torrence et al. |
| 5,677,437 A | 10/1997 | Teng et al. |
| 5,677,439 A | 10/1997 | Weis et al. |
| 5,681,940 A | 10/1997 | Wang et al. .................. 536/22.1 |
| 5,681,941 A | 10/1997 | Cook et al. |
| 5,684,142 A | 11/1997 | Mishra et al. |
| 5,684,143 A | 11/1997 | Gryaznov et al. |
| 5,684,243 A | 11/1997 | Gururaja et al. |
| 5,688,941 A | 11/1997 | Cook |
| 5,698,687 A | 12/1997 | Eckstein et al. |
| 5,700,785 A | 12/1997 | Suhadolnik et al. |
| 5,700,920 A | 12/1997 | Altmann |
| 5,700,922 A | 12/1997 | Cook ........................... 536/23.1 |
| 5,714,166 A | 2/1998 | Tomalia et al. |
| 5,714,331 A | 2/1998 | Buchardt et al. |
| 5,716,824 A | 2/1998 | Beigelman et al. |
| 5,719,262 A | 2/1998 | Buchardt et al. |
| 5,719,271 A | 2/1998 | Cook et al. |
| 5,721,218 A | 2/1998 | Froehler et al. |
| 5,726,297 A | 3/1998 | Gryaznov et al. |
| 5,750,666 A | 5/1998 | Caruthers et al. |
| 5,750,669 A | 5/1998 | Rösch et al. ................. 536/24.3 |
| 5,750,692 A | 5/1998 | Cook et al. |
| 5,760,202 A | 6/1998 | Cook et al. |
| 5,760,209 A | 6/1998 | Cheruvallath et al. ..... 536/25.34 |
| 5,763,588 A | 6/1998 | Matteucci et al. |
| 5,770,713 A | 6/1998 | Imbach et al. |
| 5,770,716 A | 6/1998 | Khan et al. |
| 5,777,092 A | 7/1998 | Cook et al. |
| 5,780,607 A | 7/1998 | Goodnow, Jr. et al. ....... 536/22.1 |
| 5,789,576 A | 8/1998 | Daily et al. |
| 5,792,608 A | 8/1998 | Swaminathan et al. |
| 5,792,747 A | 8/1998 | Schally |
| 5,792,844 A | 8/1998 | Sanghvi et al. |
| 5,792,847 A | 8/1998 | Buhr et al. |
| 5,801,154 A * | 9/1998 | Baracchini et al. ............. 514/44 |
| 5,804,683 A | 9/1998 | Usman et al. ............... 536/25.31 |
| 5,808,023 A | 9/1998 | Sanghvi et al. |
| 5,808,036 A | 9/1998 | Kool ............................ 536/24.3 |
| 5,817,781 A | 10/1998 | Swaminathan et al. |
| 5,830,635 A | 11/1998 | Agnello |
| 5,830,653 A | 11/1998 | Froehler et al. |
| 5,837,835 A | 11/1998 | Gryaznov et al. |
| 5,837,852 A | 11/1998 | Chung et al. ................. 536/24.5 |
| 5,840,876 A | 11/1998 | Beigelman et al. |
| 5,854,410 A | 12/1998 | Arnold, Jr. et al. .......... 536/23.1 |
| 5,859,221 A | 1/1999 | Cook et al. |
| 5,861,493 A | 1/1999 | Cook et al. |
| 5,872,232 A | 2/1999 | Cook et al. |
| 5,874,553 A | 2/1999 | Peyman et al. |
| 5,891,683 A | 4/1999 | Usman et al. ............... 435/91.31 |
| 5,891,684 A | 4/1999 | Usman et al. |
| 5,898,031 A | 4/1999 | Crooke et al. ............. 435/172.3 |
| 5,914,396 A | 6/1999 | Cook et al. |
| 5,936,080 A | 8/1999 | Stec et al. |
| 5,945,521 A | 8/1999 | Just et al. |
| 5,955,443 A | 9/1999 | Bennett et al. .................. 514/44 |
| 5,962,425 A | 10/1999 | Walder et al. ................... 514/44 |
| 5,965,720 A | 10/1999 | Gryaznov et al. |
| 5,965,721 A | 10/1999 | Cook et al. |
| 5,969,116 A | 10/1999 | Martin |
| 5,969,118 A | 10/1999 | Sanghvi et al. |
| 5,986,083 A | 11/1999 | Dwyer et al. |
| 5,998,203 A | 12/1999 | Matulic-Adamic et al. |
| 5,998,588 A | 12/1999 | Hoffman et al. |
| 6,001,841 A | 12/1999 | Cook et al. |
| 6,005,087 A | 12/1999 | Cook et al. |
| 6,005,094 A | 12/1999 | Simon et al. |
| 6,005,096 A | 12/1999 | Matteucci et al. |
| 6,007,992 A | 12/1999 | Lin et al. |
| 6,013,785 A | 1/2000 | Bruice et al. |
| 6,015,886 A | 1/2000 | Dale et al. |
| 6,020,475 A | 2/2000 | Capaldi et al. |
| 6,025,140 A | 2/2000 | Langel et al. |
| 6,028,183 A | 2/2000 | Lin et al. |
| 6,028,188 A | 2/2000 | Arnold, Jr. et al. |
| 6,033,910 A | 3/2000 | Monia et al. |
| 6,037,463 A | 3/2000 | Uhlmann et al. ............. 536/24.5 |
| 6,043,060 A | 3/2000 | Imanishi |
| 6,043,352 A | 3/2000 | Manoharan et al. |
| 6,046,306 A | 4/2000 | Breipohl et al. ............. 530/322 |
| 6,051,699 A | 4/2000 | Ravikumar |
| 6,087,484 A | 7/2000 | Goodchild |
| 6,096,875 A | 8/2000 | Khan et al. |
| 6,107,094 A | 8/2000 | Crooke ........................ 435/455 |
| 6,111,085 A | 8/2000 | Cook et al. |
| 6,117,657 A | 9/2000 | Usman et al. ............... 435/91.31 |
| 6,121,437 A | 9/2000 | Guzaev et al. |
| 6,127,346 A | 10/2000 | Peyman et al. |
| 6,127,533 A | 10/2000 | Cook et al. |
| 6,133,246 A | 10/2000 | McKay et al. |
| 6,147,200 A | 11/2000 | Manoharan et al. |
| 6,150,510 A | 11/2000 | Seela et al. ................... 536/22.1 |
| 6,153,737 A | 11/2000 | Manoharan et al. |
| 6,166,188 A | 12/2000 | Cook et al. |
| 6,169,177 B1 | 1/2001 | Manoharan |
| 6,172,208 B1 | 1/2001 | Cook |
| 6,172,209 B1 | 1/2001 | Manoharan et al. |
| 6,172,216 B1 | 1/2001 | Bennett et al. |
| 6,207,646 B1 | 3/2001 | Krieg et al. |
| 6,210,892 B1 | 4/2001 | Bennett et al. |
| 6,222,025 B1 | 4/2001 | Cook et al. |
| 6,227,982 B1 | 5/2001 | Wurster |

(56) References Cited

U.S. PATENT DOCUMENTS

| | | |
|---|---|---|
| 6,239,265 B1 | 5/2001 | Cook |
| 6,239,272 B1 | 5/2001 | Beigelman et al. |
| 6,262,036 B1 | 7/2001 | Arnold, Jr. et al. ............ 514/44 |
| 6,262,241 B1 | 7/2001 | Cook et al. |
| 6,268,490 B1 | 7/2001 | Imanishi et al. |
| 6,271,358 B1 | 8/2001 | Manoharan et al. |
| 6,274,723 B1 | 8/2001 | Nilsen |
| 6,277,634 B1 | 8/2001 | McCall et al. |
| 6,277,967 B1 | 8/2001 | Manoharan |
| 6,281,201 B1 | 8/2001 | Suhadolnik et al. |
| 6,284,538 B1 | 9/2001 | Monia et al. |
| 6,287,860 B1 | 9/2001 | Monia et al. |
| 6,294,522 B1 | 9/2001 | Zablocki et al. ............... 541/46 |
| 6,300,319 B1 | 10/2001 | Manoharan |
| 6,307,040 B1 | 10/2001 | Cook et al. |
| 6,326,358 B1 | 12/2001 | Manoharan |
| 6,326,478 B1 | 12/2001 | Cheruvallath et al. |
| 6,329,346 B1 | 12/2001 | Muhlegger et al. ............. 514/44 |
| 6,331,617 B1 | 12/2001 | Weeks et al. |
| 6,335,432 B1 | 1/2002 | Segev |
| 6,335,434 B1 | 1/2002 | Guzaev et al. |
| 6,335,437 B1 | 1/2002 | Manoharan et al. |
| 6,344,436 B1 | 2/2002 | Smith et al. |
| 6,358,931 B1 | 3/2002 | Cook et al. |
| 6,365,379 B1 | 4/2002 | Lima et al. |
| 6,380,169 B1 | 4/2002 | Adams et al. .................. 514/44 |
| 6,395,437 B1 | 5/2002 | Wollesen |
| 6,395,474 B1 | 5/2002 | Buchardt et al. ................ 435/6 |
| 6,395,492 B1 | 5/2002 | Manoharan et al. |
| 6,410,702 B1 | 6/2002 | Swaminathan et al. |
| 6,414,127 B1 | 7/2002 | Lin et al. |
| 6,420,549 B1 | 7/2002 | Cook et al. |
| 6,426,220 B1 | 7/2002 | Bennett et al. |
| 6,436,640 B1 | 8/2002 | Simmons et al. ................ 435/6 |
| 6,440,943 B1 | 8/2002 | Cook et al. |
| 6,444,806 B1 | 9/2002 | Veerapanani et al. |
| 6,465,628 B1 | 10/2002 | Ravikumar et al. |
| 6,476,205 B1 | 11/2002 | Buhr et al. |
| 6,486,308 B2 | 11/2002 | Kutyavin et al. |
| 6,506,559 B1 | 1/2003 | Fire et al. |
| 6,525,031 B2 | 2/2003 | Manoharan |
| 6,528,631 B1 | 3/2003 | Cook et al. |
| 6,531,584 B1 | 3/2003 | Cook et al. |
| 6,534,639 B1 | 3/2003 | Manoharan et al. |
| 6,559,279 B1 | 5/2003 | Manoharan et al. |
| 6,573,072 B1 | 6/2003 | Goodchild ................. 435/91.31 |
| 6,593,466 B1 | 7/2003 | Manoharan et al. |
| 6,656,730 B1 | 12/2003 | Manoharan |
| 6,670,461 B1 | 12/2003 | Wengel et al. |
| 6,673,611 B2 | 1/2004 | Thompson et al. |
| 6,683,167 B2 | 1/2004 | Metelev et al. |
| 6,794,499 B2 | 9/2004 | Wengel et al. |
| 6,818,759 B2 | 11/2004 | Beigelman et al. |
| 6,849,726 B2 | 2/2005 | Usman et al. ................ 536/23.1 |
| 6,887,906 B1 | 5/2005 | Teng et al. |
| 7,022,828 B2 | 4/2006 | McSwiggen |
| 2002/0049173 A1 | 4/2002 | Bennett et al. |
| 2002/0068708 A1 | 6/2002 | Wengel et al. ................. 514/44 |
| 2002/0071826 A1 | 6/2002 | Tamarkin et al. |
| 2002/0081577 A1 | 6/2002 | Kilkuskie et al. |
| 2002/0081736 A1 | 6/2002 | Conroy et al. |
| 2002/0102267 A1 | 8/2002 | Lu et al. |
| 2002/0132788 A1 | 9/2002 | Lewis et al. .................. 514/44 |
| 2002/0147332 A1 | 10/2002 | Kaneko |
| 2002/0151512 A1 | 10/2002 | Peyman et al. |
| 2002/0156235 A1 | 10/2002 | Manoharan et al. |
| 2002/0160393 A1 | 10/2002 | Symonds et al. ................ 435/6 |
| 2002/0162126 A1 | 10/2002 | Beach et al. |
| 2002/0165189 A1 | 11/2002 | Crooke |
| 2003/0004325 A1 | 1/2003 | Cook et al. |
| 2003/0027780 A1 | 2/2003 | Hardee et al. |
| 2003/0096286 A1 | 5/2003 | Crooke |
| 2003/0096287 A1 | 5/2003 | Crooke |
| 2003/0096784 A1 | 5/2003 | Crooke |
| 2003/0119777 A1 | 6/2003 | Crooke |
| 2003/0125241 A1 | 7/2003 | Wissenbach et al. |
| 2003/0139585 A1 | 7/2003 | Uhlmann et al. |
| 2003/0143732 A1 | 7/2003 | Fosnaugh et al. ............. 435/325 |
| 2003/0158403 A1 | 8/2003 | Manoharan et al. |
| 2003/0166282 A1 | 9/2003 | Brown et al. |
| 2003/0175906 A1 | 9/2003 | Manoharan et al. |
| 2003/0187240 A1 | 10/2003 | Cook et al. |
| 2003/0190635 A1 | 10/2003 | McSwiggen |
| 2003/0206887 A1 | 11/2003 | Morrissey et al. ........... 424/93.2 |
| 2003/0207804 A1 | 11/2003 | Manoharan et al. |
| 2003/0224377 A1 | 12/2003 | Wengel et al. |
| 2004/0001811 A1 | 1/2004 | Kreutzer et al. |
| 2004/0009938 A1 | 1/2004 | Manoharan et al. |
| 2004/0014957 A1 | 1/2004 | Eldrup et al. |
| 2004/0018999 A1 | 1/2004 | Beach et al. .................... 514/44 |
| 2004/0029275 A1 | 2/2004 | Brown et al. |
| 2004/0102618 A1 | 5/2004 | Crooke et al. |
| 2004/0146867 A1 | 7/2004 | Slattum et al. |
| 2004/0171033 A1 | 9/2004 | Baker et al. |
| 2004/0180351 A1 | 9/2004 | Giese et al. |
| 2004/0259247 A1 | 12/2004 | Tuschl et al. |
| 2005/0020525 A1 | 1/2005 | McSwiggen et al. |
| 2005/0080246 A1 | 4/2005 | Allerson et al. |
| 2005/0142535 A1 | 6/2005 | Damha et al. |
| 2005/0164209 A1 | 7/2005 | Bennett et al. |
| 2005/0181382 A1 | 8/2005 | Zamore et al. |
| 2005/0221275 A1 | 10/2005 | Bennett et al. |
| 2005/0245474 A1 | 11/2005 | Baker et al. |
| 2005/0273868 A1 | 12/2005 | Rana |
| 2006/0127891 A1 | 6/2006 | McSwiggen et al. |
| 2007/0032446 A1 | 2/2007 | Cook et al. |

FOREIGN PATENT DOCUMENTS

| | | | |
|---|---|---|---|
| DE | 4110085 A1 | 1/1992 | |
| DE | 10100588 A1 | 7/2002 | |
| EP | 0260032 A2 | 3/1988 | |
| EP | 0 266 168 A2 | 5/1988 | |
| EP | 0269574 A2 | 6/1988 | |
| EP | 0287313 A2 | 10/1988 | |
| EP | 0339330 A2 | 11/1989 | |
| EP | 339842 | 11/1989 | |
| EP | 0339842 A2 * | 11/1989 | ............ C07H 21/00 |
| EP | 0417999 A1 | 3/1991 | |
| EP | 1389637 A1 | 2/2004 | |
| WO | WO 86/05518 A1 | 9/1986 | |
| WO | WO 89/12060 A1 | 12/1989 | |
| WO | WO 90/15814 A1 | 12/1990 | |
| WO | WO 91/06556 A1 | 5/1991 | |
| WO | WO 91/10671 A1 | 7/1991 | |
| WO | WO 91/15499 A1 | 10/1991 | |
| WO | WO 92/02258 A1 | 2/1992 | |
| WO | WO 92/03452 A1 | 3/1992 | |
| WO | WO 92/03568 A1 | 3/1992 | |
| WO | WO 92/07065 | 4/1992 | |
| WO | WO 92/20822 | 11/1992 | |
| WO | WO 92/20823 | 11/1992 | |
| WO | WO 92/22651 | 12/1992 | |
| WO | WO 93/07883 A1 | 4/1993 | |
| WO | WO 93/24510 A1 | 12/1993 | |
| WO | WO 94/01550 | 1/1994 | |
| WO | WO 94/01550 A1 | 1/1994 | |
| WO | WO 94/02498 A1 | 2/1994 | |
| WO | WO 94/02499 | 2/1994 | |
| WO | WO 94/02501 | 2/1994 | |
| WO | WO 94/17093 | 8/1994 | |
| WO | WO 94/23026 A1 | 10/1994 | |
| WO | WO 94/26764 A1 | 11/1994 | |
| WO | WO 96/07392 A2 | 3/1996 | |
| WO | WO 96/11205 A1 | 4/1996 | |
| WO | WO 97/26270 A2 | 7/1997 | |
| WO | WO 97/30064 A1 | 8/1997 | |
| WO | WO 97/46570 A1 | 12/1997 | |
| WO | WO 98/16550 A1 | 4/1998 | |
| WO | WO 98/39352 A1 | 9/1998 | |
| WO | WO 98/52614 A2 | 11/1998 | |
| WO | WO 99/14226 | 3/1999 | |
| WO | WO 99/32619 | 7/1999 | |
| WO | WO 00/08044 A1 | 2/2000 | |

(56) References Cited

FOREIGN PATENT DOCUMENTS

| | | |
|---|---|---|
| WO | WO 00/44895 | 8/2000 |
| WO | WO 00/44914 | 8/2000 |
| WO | WO 00/49035 | 8/2000 |
| WO | WO 00/63364 | 10/2000 |
| WO | WO 00/76554 A1 | 12/2000 |
| WO | WO 01/29058 | 4/2001 |
| WO | WO 01/36641 A2 | 5/2001 |
| WO | WO 01/36646 A1 | 5/2001 |
| WO | WO 01/48183 A2 | 7/2001 |
| WO | WO 01/49687 A2 | 7/2001 |
| WO | WO 01/75164 A3 | 10/2001 |
| WO | WO 02/36743 A2 | 5/2002 |
| WO | WO 02/38578 A1 | 5/2002 |
| WO | WO 02/44321 | 6/2002 |
| WO | WO 02/44321 A2 | 6/2002 |
| WO | WO 03/004602 A2 | 1/2003 |
| WO | WO 03/070918 A2 | 8/2003 |
| WO | WO 03/072705 A2 | 9/2003 |
| WO | WO 2004/015107 A2 | 2/2004 |
| WO | WO 2004/041889 A2 | 5/2004 |
| WO | WO 2004/043977 A2 | 5/2004 |
| WO | WO 2004/043978 A2 | 5/2004 |
| WO | WO 2004/043979 A2 | 5/2004 |
| WO | WO 2004/044133 A2 | 5/2004 |
| WO | WO 2004/044136 A2 | 5/2004 |
| WO | WO 2004/044138 A2 | 5/2004 |
| WO | WO 2004/044139 A2 | 5/2004 |
| WO | WO 2004/044140 A2 | 5/2004 |
| WO | WO 2004/083430 A2 | 9/2004 |
| WO | WO 2004/097049 A1 | 11/2004 |
| WO | WO 2004/113496 A2 | 12/2004 |
| WO | WO 2005/027962 A2 | 3/2005 |

OTHER PUBLICATIONS

Manche, et al. (1992) Interactions Between Double-Stranded RNA Regulators and the Protein Kinase DAI. Molecular and Cellular Biology, v.12(11):5238-48.*

Monia, et al (1993) Evaluation of 2'-Modified Oligonucleotides Containing 2'-Deoxy Gaps as Antisense Inhibitors of Gene Expression, The Journal of Biological Chemistry, v.268(9):14514-22.*

Manche, et al. (1992) Interactions Between Double-Stranded RNA Regulators and the Protein Kinase DAI, Molecular and Cellular Biology, v.12(11):5238-48.*

Wyatt, et al. (1989) Deoxynucleotide-Containing Oligoribonucleotide Duplexes: Stability and Susceptibility to RNase v1 and RNase H, Nucleic Acids Research, v.17(19):7833-42.*

Elbashir, *EMBO J.*, 2001, 20, 6877-6888.

Table listing related applications and office actions and rejections from those related applications.

Hunzlker, J., et al., "Nucleic acid analogues: synthesis and properties," *Modern Synthetic Methods*, 1995, 331, 334-417.

Rajwanshi, V.K., et al., "LNA stereoisomers: *xylo*-LNA (β-D-*xylo* configured locked nucleic acid) and α-L-ribo configured locked nucleic acid)," *Chem. Commun.*, 1999, 1395-1396.

Steffens, R., et al., "Synthesis and thermodynamic and biophysical properties of tricycle-DNA," *Am. Chem. Soc.*, 1999, 121(14), 3249-3255.

Amarzguioui, M., et al., "Tolerance for mutations and chemical modifications in a siRNA," *Nucleic Acids Res.*, 2003, 31(2), 589-595.

Bass, B.L., "Double-stranded RNA as a template for gene silencing," *Cell*, 2000, 101, 235-238.

Wang, J., et al., "Cyclohexene nucleic acids (CeNA): serum stable oligonucleotides that activate RNase H and increase duplex stability with complementary RNA," *J. Am. Chem. Soc.*, 2000, 122, 8595-8602.

PCT International Search Report dated Aug. 23, 2004 (PCT/US03/35063).

Beigelman, L., et al., "Chemical modification of hammerhead ribozymes," *J. of Biological Chem.*, 1995, 270(43), 257082-25708.

Caplen, N.J., et al., "Specific inhibition of gene expression by small double-stranded RNAs in invertebrate and vertebrate systems," *PNAS*, 2001, 98(17), 9742-9747.

Czauderna, F., et al., "Structural variations and stabilizing modifications of synthetic siRNAs in mammalian cells," *Nucleic Acids Res.*, 2003, 31(11), 2705-2716.

Paddison, P.J., et al., "Stable suppression of gene expression by RNAi in mammalian cells," *PNAS*, 2002, 99(3), 1443-1448.

Sui, G., et al., "A DNA vector-based RNAi technology to suppress gene expression in mammalian cells," *PNAS*, 2002, 99(8), 5515-5520.

Yu, J.-Y., et al., "RNA interference by expression of short-interfering RNAs and hairpin RNAs in mammalian cells," *PNAS*, 2002, 99(9), 6047-6052.

PCT International Search Report dated Aug. 2, 2004 (PCT/US03/35068).

Zhou, Y., et al., "Post-transcriptional suppression of gene expression in *Xenopus* embryos by small interfering RNA," *Nucleic Acids Res.*, 2002, 30(7), 1664-1669.

The PCT International Search Report dated Apr. 13, 2004 (PCT/US03/35072).

The PCT International Search Report dated Dec. 1, 2003 (PCT/US03/19043).

Beaucage S. and Iyer, R., "Advances in the synthesis of oligonucleotides by the phosphoramidite approach", *Tetrahedron Letters*, 1992, 48, 2223-2311.

Bhat, et al., "A Simple and Convenient Method for the Selective N-Acylations of Cytosine Nucleosides", *Nucleosides and Nucleotides*, 1989, 8, 179-183.

Crooke, S.T. and Bennett, C.F., "Progress in Antisense Oligonucleotide Therapeutics", *Annu. Rev. Pharmacol. Toxicol.*, 1996, 36, 107-129.

Crooke, et al., "Kinetic characteristics of *Escherichia coli* Rnase H1: cleavage of various antisense oligonucleotide-RNA duplexes", *Biochem. J.*, 1995, 312, 599-608.

Dagle, et al., "Targeted degradation of mRNA in *Xenopus* oocytes and embryos directed by modified oligonucleotides: studies of An2 and cyclin in embryogenesis", *Nucleic Acids Research*, 1990, 18, 4751-4757.

Dagle, et al., "Pathways of Degradation and Mechanism of Action of Antisense Oligonucleotides in *Xenopus laevis* Embryos", *Antisense Res. and Dev.*, 1991, 1, 11-20.

Dagle, et al., "Physical properties of oligonucleotides containing phosphoramidate-modified internucleoside linkages", *Nucleic Acids Research*, 1991, 19, 1805-1810.

Englisch, U. and Gauss, D.H., "Chemically Modified Oligonucleotides as Probes and Inhibitors", *Angewandt Chemie, International Edition Engl.*, 1991, 30, 613-629.

Haeuptle and Dobberstein, "Translation arrest by oligonucleotides complementary to mRNA coding sequences yields polypeptides of predetermined length", *Nucleic Acids Res.*, 1986, 14, 1427-1448.

Eder, P.S. and Walder, J.A., "Ribonuclease H from K562 Human Erythroleukemia Cells", *J. Biol. Chem.*, 1991, 266, 6472-6479.

Kawasaki, et al., "Uniformly Modified 2'-Deoxy-2'-fluoro Phosphorothioate Oligonucleotides as Nuclease-Resistant Antisense Compounds with High Affinity and Specificity for RNA Targets", *J. Med. Chem.*, 1993, 36, 831-841.

Kawasaki, et al., "Synthesis and Biophysical Studies of 2'-dRIBO-2'-F Modified Oligonucleotides", ISIS Pharmaceuticals, Inc., 2280 Faraday Avenue, Carlsbad, CA 92008, USA.

Monia, et al., "Selective Inhibition of Mutant Ha-ras mRNA Expression by Antisense Oligonucleotides", *J. Biol. Chem.*, 1992, 267, 19954-19962.

Monia, et al., "Evaluation of 2'-Modified Oligonucleotides Containing 2'-Deoxy Gaps as Antisense Inhibitors of Gene Expression", *J. Biol. Chem.*, 1993, 268, 14514-14522.

Robins, et al., "Nucleic acid related compounds. 41. Restricted furanose conformations of 3',5'-O(1,1,3,3-tetraisoprpyldisilox-1,3-diyl)nucleosides provide a convenient evaluation of anomeric configuration[1,2]", *Can. J. Chem.*, 1983, 61, 1911-1920.

(56) References Cited

OTHER PUBLICATIONS

Saison-Behmoaras, T., et al., "Short modified antisense oligonucleotides directed against Ha-ras point mutation induce selective cleavage of the mRNA and inhibit T24 cells proliferation", *EMBO*, 1991, 10, 1111-1118.

Concise Encyclopedia of Polymer Science and Engineering, pp. 858-859, Kroschwitz, J.I., Ed., John Wiley & Sons, 1990.

Oligonucleotide and Analogs, A Practical Approach, F. Eckstein, Ed., IRL Press, 1991, Chapters 1-7.

De Mesmeker, et al., "Antisense Oligonucleotides", *Acc. Chem. Res.*, 1995, 28, 366-374.

Sands, et al., "Biodistribution and Metabolism of Internally [3]H-Labeled Olionucleotides. II. 3',5'-Blocked Oligonucleotides", *Am. Soc. Pharmacol. Exp. Ther.*, 1995, 47, 636-646.

Strickland, et al., "Antisense RNA Directed Against the 3' Noncoding Region Prevents Dormant mRNA Activation in Mouse Oocytes", *Science*, 1988, 241, 680-684.

Goodchild, et al., "Conjugates of Oligonucleotides and Modified Oligonucleotides: A Review of their Synthesis and Properties", *Bioconjugate Chem.*, 1990, 1(3), 165-187.

Tseng, et al., "Antisense Oligonucleotide Technology in the Development of Cancer Therapeutics", *Cancer Gene Therapeutics*, 1994, 1, 65-71.

Westermann, et al., "Inhibition of expression of SV40 virus large T-antigen by antisense oligodeoxyribonucleotides", *Biomed. B. Acta.*, 1989, 48, 85-93.

Stein, C.A. et al., "Antisense Oligonucleotides as Therapeutic Agents—Is the Bullet Really Magical?", *Science*, 1993, 261, 1004-1012.

Stull, et al., "Antigene, Ribozyme and Aptamer Nucleic Acid Drugs: Progress and Prospects", *Pharm. Res.*, 1995, *Pharm. Rev.*, 12, 465-482.

Uhlmann, et al., "Antisense Oligonucleotides: A New Therapeutic Principle", *Chem. Rev.*, 1990, 90, 543.

Akashi, et al., "Novel Stationary Phases for Affinity Chromatography. Nucleobase-Selective Recognition of Nucleosides and Nucleotides on Poly(9-vinyladenine)-Supported Silica Gel[1]", *Chem. Letters*, 1988, 1093-1096.

Alberts, et al., "DNA-Cellulose Chromatography", *Meth. Enzymol.*, 1971, 21, 198-217.

Arndt-Jovin, et al., "Covalent Attachment of DNA to Agarose", *Eur. J. Biochem.*, 1975, 54, 411-418.

Blanks, et al., "An oligodeoxynucleotide affinity column for the isolation of sequence specific DNA binding proteins", *Nucleic Acids Res.*, 1988, 16, 10283-10299.

Blomberg, P., "Control of replication of plasmid R1: the duplex between the antisense RNA, CopA, and its target, CopT, is processed specifically in vivo and in vitro by Rnase III", *EMBO J.*, 1990, 9, 2331-2340.

Bunemann, et al., Immobilization of denatured DNA to macroporous supports: I. Efficiency of different coupling procedures, *Nucleic Acids Res.*, 1982, 10, 7163-7180.

Bunemann, H., "Immobilization of denatured DNA to macroporous supports: II. Steric and kinetic parameters of heterogeneous hybridization reactions", *Nucleic Acids Res.*, 1982, 10, 7181-7196.

Chodosh, et al., "A Single Polypeptide Possesses the Binding and Transcription Activities of the Adenovirus Major Late Transcription Factor", *Mol. Cell. Biol.*, 1986, 6, 4723-4733.

Crooke, et al., "Phmarmacokinetic Properties of Several Novel Oligonucleotide Analogs in mice", *J. Pharmacol. Exp. Therm.*, 1996, 277, 923-927.

Dake, et al., "Purification and Properties of the Major Nuclease from Mitochondria of *Saccharomyces cerevisiae*", *J. Biol. Chem.*, 1988, 263, 7691-7702.

Day, et al., "Immobilization of polynucleotides on magnetic particles", *Biochem. J.*, 1991, 278, 735-740.

Drmanac, et al., "DNA Sequence Determination by Hybridization: A Strategy for Efficient Large-Scale Sequencing", *Science*, 1993, 260, 1649-1652.

Duncan, et al., "Affinity Chromatography of a Sequence-Specific DNA Binding Protein Using Teflon-Linked Oligonucleotides", *Anal. Biochem.*, 1988, 169, 104-108.

Dunn, J.J. and Studier, F.W., "Effect of RNAase III Cleavage on Translation of Bacteriophage T7 Messenger RNAs", *J. Mol. Biol.*, 1975, 99, 487-499.

Elela, et al., "RNase III Cleaves Eukaryotic Preribosomal RNA at a U3 snoRNP-Dependent Site", *Cell*, 1996, 85, 115-124.

Fahy, et al., "Design and synthesis of polyacrylamide-based oligonucleotide supports for use in nucleic acid diagnostics", *Nucl. Acids Res.*, 1993, 21, 1819-1826.

Fishel, et al., "Z-DNA Affinity Chromatography", *Methods Enzymol.*, 1990, 184, 328-342.

Fodor, et al., "Light-Directed, Spatially Addressable Parallel Chemical Synthesis", *Science*, 1991, 251, 767-773.

Fusi, et al., "Ribonucleases from the extreme thermophilic archaebacterium *S. solfataricus*", *Eur. J. Biochem.*, 1993, 16, 305-310.

Gabrielsen, et al., "Magnetic DNA affinity purification of yeast transcription factor τ—a new purification principle for the ultrarapid isolation of near homogeneous factor", *Nucleic Acids Research*, 1989, 17, 6253-6267.

Gbenle, "*Trypanosoma brucei*: Calcium-Dependent Endoribonuclease is Associated with Inhibitor Protein",, *Exp. Parasitol.*, 1990, 71, 432-438.

Gbenle, "Simultaneous Isolation of Cytoplasmic Endoribonuclease and Exoribonucease of *Trypanosoma brucei*", *Mol. Biochem. Parasitol.*, 1985, 15, 37-47.

Gerdes, K., et al., "Mechanism of Killer Gene Activation. Antisense RNA-dependent Rnase III Cleavage Ensures Rapid Turn-over of the Stable-Hok, SrnB and PndA Effector Messenger RNAs", *J. Mol. Biol.*, 1992, 226, 637-649.

Gingeras, et al., "Hybridization properties of immobilized nucleic acids", *Nucl. Acids Res.*, 1987, 15, 5373-5391.

Goldkorn, T. and Prockop, D.J., "A simple and efficient enzymatic method for covalent attachment of DNA to cellulose. Application for hybridization-restriction analysis and for in vitro synthesis of DNA probes", *Nucleic Acids Res.*, 1986, 14, 9171-9191.

Goss, T.A. and Bard, M., "High-performance affinity chromatography of DNA", *J. Chromatogr.*, 1990, 508, 279-287.

Guo, et al., "Direct fluorescence analysis of genetic polymorphisms by hybridization with oligonucleotide arrays on glass supports", Nucl. Acids Res., 1994, 22, 5456-5465.

Kadonaga, J.T. and Tjian, R., "Affinity purification of sequence-specific DNA binding proteins", *Proc. Natl. Acad. Sci. USA*, 1986, 83, 5889-5893.

Kadonaga, J.T., "Purification of Sequence-Specific Binding Proteins b DNA Affinity Chromatography", *Methods in Enzymology*, 1991, 208, 10-23.

Kasher, et al., "Rapid Enrichment of HeLa Trancription Factors IIIB and IIIC by Using Affinity Chromatography Based on Avidin-Biotin Interactions", *Mol. and Cell. Biol.*, 1986, 6, 3117-3127.

Kawaguchi, et al., "Purification of DNA-binding transcription factors by their selective adsorption of the affinity atex particles", *Nucleic Acids Research*, 1989, 17, 6229-6240.

Kennedy, "Hydrophobic Chromatography", *Methods in Enzymology*, 1990, 182, 339-343.

Knecht, D., "Application of Antisense RNA to the Study of the Cytoskeleton: Background, Principles, and a Summary of Results Obtained with Myosin Heavy Chain", *Cell Motil. and Cytoskel.*, 1989, 14, 92-102.

Knochbin and Lawrence, "An antisense RNA involved in p53 mRNA maturation in murine erythroleukemia cells induced to differentiate", *EMBO J.*, 1989, 8, 4107-4114.

Krinke, L. and Wulff, D., "RNase III-dependent hydrolysis of λcII-O gene mRNA mediated by λ OOP antisense RNA" *Genes & Devel.*, 1990, 4, 2223-2233.

Krystal, et al., "N-*myc* mRNA Forms an RNA-RNA Duplex with Endogenous Antisense Transcripts", *Mol. and Cell. Biol.*, 1990, 10, 4180-4191.

Liao, "A pyrimidine-guanine sequence-specific ribonuclease from *Rana catesbeiana* (bullfrog) oocytes", *Nucl. Acids Res.*, 1992, 20, 1371-1377.

(56) References Cited

OTHER PUBLICATIONS

Lohrmann, et al., "New Solid Supports for DNA Synthesis" *DNA*, 1984, 3, 122.

Lund, et al., "Assessment of methods for covalent binding of nucleic acids to magnetic beads, Dynabead™, and the characteristics of the bound nucleic acids in hybridization reactions", *Nucl. Acids Res.*, 1988, 16, 10861-10880.

Maniak, M. and Nellen, W., "Evidence for a feedback regulated back-up promoter which controls permanent expression of a *Dictyostelium* gene", *Nucl. Acids Res.*, 1990, 18, 5375-5380.

Matson, et al., "Biopolymer Synthesis on Polypropylene Supports", *Anal. Biochem.*, 1994, 217, 306-310.

Maskos, U. and Southern, E.M., "Oligonucleotide hybridisations on glass supports: a novel linker for oligonucleotide synthesis and hybridisation properties of oligonucleotides synthesised in situ", *Nucl. Acids. Res.*, 1992, 20, 1679-1684.

Meegan, J.M. and Marcus, P.I., "Double-Stranded Ribonuclease Coinduced with Interferon", *Science*, 1989, 244, 1089-1091.

Narhi, et al., "Hydrophobic Interaction Chromatography in Alkaline pH", *Anal. Biochem.*, 1989, 182, 266-270.

Nellen, W., C., "What makes an mRNA anti-sense-itive?", *Curr. Opin. Cell. Biol.*, 1993, 18, 419-424.

Nellen, W., et al., "Mechanisms of gene regulation by endogenous and artificially introduced antisense RNA", *Biochem., Soc. Trans.*, 1992, 20, 750-754.

Nitta, et al., "Purification and Some Properties of Ribonuclease from *Xenopus laevis* Eggs", *Biol. Pharm. Bull.* (Jpn.), 1993, 16, 353-356.

Noguchi, et al., "Characterization of an Antisense Inr Element in the eIF-2α Gene", *J. Biol. Chem.*, 1994, 269, 29161-29167.

Noyes, et al., "Nucleic Acid Hybridization Using DNA Covalently Coupled to Cellulose", *Cell*, 1975, 5, 301-310.

Pease, et al., "Light-generated oligonucleotide arrays for rapid DNA sequence analysis", *Proc. Natl. Acad. Sci. USA*, 1994, 91, 5022-5026.

Pon, et al., "Derivatization of Controlled Pore Glass Beads for Solid Phase Oligonucleotide Synthesis", *BioTech.*, 1988, 6, 768-773.

Prokipcak, et al., "Purification and Properties of a Protein that Binds to the C-terminal Coding Region of Human c-myc mRNA", *J. Biol. Chem.*, 1994, 269, 9261-2969.

Saito, H. and Richardson, C., "Processing of mRNA by Ribonuclease III Regulates Expression of Gene 1.2 of Bacteriophage T7", 1981, *Cell*, 27, 533-542.

Seliger,H. and Aumann, G., "Oligonucleotide Synthesis on a Polymer Support Soluble in Water and Pyridine", *Tetrahedron Letters*, 1973, No. 31, 2911-2914.

Siddell, S.G., "RNA Hybridization to DNA Coupled with Cyanogen-Bromide-Activated Sephadex", *Eur. J. Biochem.*, 1978, 92, 621-629.

Smith, et al., "The synthesis of oigonucleotides containing an aliphatic amino group at the 5' terminus: synthesis of fluorescent DNA primers for use in DNA sequence analysis", *Nucl. Acids Res.*, 1985, 13, 2399-2412.

Stoldt, P. and Zillig, W., "Antisense RNA mediates transcriptional procesing in an archaebacterium, indicating a novel kind of RNase activity", *Mol. Microbiol.*, 1993, 7, 875-882.

Syvanen, et al., "Quantification of polymerase chain reaction products by affinity-based hybrid collection", *Nucl. Acids Res.*, 1988, 16, 11327-11338.

Szyf, et al., "Growth Regulation of Mouse DNA Methyltransferase Gene Expression", *J. Biol. Chem.*, 1991, 266, 10027-10030.

McBride, L.J. and Caruthers, M.H.,"An Investigation of Several Deoxynucleoside Phosphoramidites Useful for Synthesizing Deoxyoligonucleotides", *Tetrahedron Letters*, 1983, 24, 245-248.

Van Ness, et al., "A versatile solid support system for oligodeoxynucleotide probe-based hybridization assays", *Nucleic Acids Research*, 1991, 19, 3345-3350.

Volk, et al., "An antisense transcript from the *Xenopus laevis* bFGF gene coding for an evolutionariy conserved 24 kd protein", *EMBO J.*, 1989, 8, 2983-2988.

Wetlaufer, et al., "Surfactant-Mediated Protein Hydrophobic-Interaction Chromatography", *J. Chromatography*, 1986, 359, 55-60.

Wu, et al., "Purification and Properties of *Drosophila* Heat Shock Activator Protein", *Science*, 1987, 238, 1247-1253.

Wu, et al., "High Resolution Separation and Analysis of Biological Macromolecules", *Methods in Enzymology*, 1996, 270, 27-47.

Yashima, et al., "High-performance affinity chromatography of oligonucleotides on nucleic acid analogue immobilized silica gel columns", *J. Chromatog.*, 1992, 603, 111-119.

Yasuda, et al., "Purification and characterization of a ribonuclease from human spleen", *Eur. J. Biochem.*, 1990, 191, 523-529.

Zarytova, et al., "Affinity Chromatography of DNA Fragments and P-Modified Oligonucleotides", *Analyt. Biochem.*, 1990, 188, 214-218.

Zuckermann, et al., "Efficient methods for attachment of thiol specific probes to the 3'-ends of synthetic oligodeoxyribonucleotides", *Nucleic Acids Research*, 1987, 15, 5305-5321.

Hyrup, B. and Nielsen, P., "Peptide Nucleic Acids (PNA): Synthesis, Properties and Potential Applications", *Bioorganic & Med. Chem.*, 1996, 4, 5-23.

Agrawal, S. et al., "Synthesis and Anti-HIV Activity of Oligoribonucleotides and Their Phosphorothioate Analogs," *Ann. N.Y. Acad. Sci.*, 1992, 2-10.

Shibahara, S. et al., "Inhibition of human immunodeficiency virus (HIV-1) replication by synthetic oligo-RNA derivatives," *Nucl. Acids Res.*, 1989, 17(1), 239-252.

Agrawal, S., "Antisense Oligonucleotides: Towards Clinical Trials," *Tibtech*, 1996, 14, 376-388.

Branch, A., "A Good Antisense is Hard to Find," *TIBS*, 1998, 23, 45-50.

Metelev, et al., "Study of antisense oligonucleotide phosphorothioates containing segments of oligodeoxynucleotides and 2'-methyloligoribonucleotides", *Bioorg. & Med. Chem. Lett.*, 1994, 4, 2929-2934.

Monia, et al., "Antitumor activity of a phosphorothioate antisense oligodeoxynucleotide targeted against c-raf kinase", *Nature Medicine*, 1996, 2, 668-675.

Ohtsuki, et al., "Isolation and purification of double-stranded ribonuclease from calf thymus", *J. Biol. Chem.*, 1977, 252, 483-491.

Arya, S. K. et al., "Inhibition of RNA Directed DNA Polymerase of Murine Leukemia Virus by 2'-O-Alkylated Polyadenylic Acids," *Biochemical and Biophysical Research Communications*, 1974, 59(2), 608-615.

Arya, S. K. et al., "Inhibition of Synthesis of Murine Leukemia Virus in Cultured Cells by Polyribonucleotides and Their 2'-O-Alkyl Derivatives," *Molecular Pharmacology*, 1976, 12, 234-241.

Hobbs, J. et al., "Polynucleotides Containing 2'-Amino 2'-deoxyribose and 2'-Azido-2'-deoxyribose†," *Biochem.*, 1973, 12, 5138-5145.

Hobbs, J. et al., Poly 2'-Deoxy-2'-Aminouridylic Acid, 1972, 46(4), 1509-1515.

Hobbs, J. et al., "Polynucleotides Containing 2'-Chloro-2'-deoxyribose," *Biochem.*, Eckstein et al., Ed., 1972, 11, 4336-4344.

Wincott et al., "Synthesis, deprotection, analysis and purification of RNA and ribozymes," *Nucl. Acids Res.*, 1995, 23(14), 2677-2684.

DeClercq, E. et al., "Influence of various 2- and 2'-substituted polyadenyl acids on murine leukemia virus reverse transcriptase," *Cancer Letters*, 1979, 7, 27-37.

Pieken, W. et al., "Kinetic Characterization of Ribonuclease-Resistant 2'-Modified Hammerhead Ribozymes," *Science*, 1991, 253, 314-317.

Pilet, J. et al., "Structural parameters of single and double helical polyribonucleotides," *Biochem Biophys Res Commun*, 1973, 52(2), 517-523.

Rottman, F. et al., "Polynucleotides Containing 2'-0-Methyladenosine. I. Synthesis by Polynucleotide Phosphorylase," *Biochem*, 1968, 7, 2634-2641.

Rottman, F. et al., "Polymers Containing 2'-O-Methylnucleotides. II. Synthesis of Heteropolymers," *Biochem*, 1969, 8(11), 4354-4361.

Zmudzka, B. et al., "Poly 2'-0-methylcytidylic acid and the role of the 2'-hydroxyl in polynucleotide structure," *Biochem Biophys Res Commun*, 1969, 37(6), 895-901.

Boutla, A., et al., "Short 5'-phosphorylated double-stranded RNAs induce RNA interference in *Drosophila*," *Curr. Biol.*, 2001, 11, 1776-1780.

(56) References Cited

OTHER PUBLICATIONS

Brantl, S., "Antisense-RNA regulation and RNA interference," *Biochimica et Biophysica Acta*, 2002, 1575, 15-25.
Carmell, M.A., et al., "The argonaute family: tentacles that reach into RNAi, developmental control, stem cell maintenance, and tumorigenesis," *Genes and Development*, 2002, 16, 2733-2742.
Chiu, Y.-L., et al., "RNAi in human cells: basic structural and functional features of small interfering RNA," *Molecular Cell*, Sep. 2002, 10, 549-561.
Cogoni, C., et al., "Post-transcriptional gene silencing across kingdoms," *Curr. Opinion in Genes Dev.*, 2000, 10, 638-643.
Elbashir, S.M., et al., "Functional anatomy of siRNAs for mediating efficient RNAi in *Drosophila melanogaster* embryo lysate," *EMBO J.*, 2001, 29(23), 6877-6888.
Elbashir, S.M., et al., "RNA interference is mediated by 21- and -22-nucleotide RNA's," *Genes & Dev.*, 2001, 15, 188-200.
Elbashir, S.M., et al., "Duplexes of 21-nucleotide RNAs mediate RNA interference in cultured mammalian cells," *Nature*, May 24, 2001, 411, 494-498.
Fire, A., et al., "Potent and specific genetic interference by double-stranded RNA in *Caenorhabditis elegans*," *Nature*, Feb. 19, 1998, 391, 806-811.
Guo, S., et al., "*par*-1, a gene required for establishing polarity in *C. elegans* embryos, encodes a putative Ser/Thr kinase that is asymmetrically distributed," *Cell*, May 19, 1995, 81, 611-620.
Gura, T., "A silence that speaks volumes," *Nature*, Apr. 20, 2000, 404, 804-808.
Jorgensen, R.A., et al., "Chalcone sythase cosuppression phenotypes in petunia flowers: comparison of sense vs. antisense contructs and single-copy vs. complex T-DNA sequences," *Plant Mol. Biol.*, 1996, 31, 957-973.
Lipardi, C., et al., "RNAi as random degradative PCR: siRNA primers convert mRNA into dsRNAs that are degraded to generate new siRNAs," *Cell*, Nov. 2, 2001, 107, 297-307.
Martinez, J., et al., "Single-stranded antisense siRNAs guide target RNA cleavage in RNAi," *Cell*, Sep. 6, 2002, 110, 563-574.
Mellitzer, G., et al., "Spatial and temporal 'knock down' of gene expression by electroporation of double-stranded RNA and morpholinos into early postimplantation mouse embryos," *Mechanisms of Development*, 2002, 118, 57-63.
Montgomery, M.K., et al., "RNA as a target of double-stranded RNA-mediated genetic interference in *Caenorhabditis elegans*," *Proc. Natl. Acad. Sci. USA*, Dec. 1998, 95, 15502-15507.
Napoli, C., et al., "Introduction of a chimeric chalcone synthase gene into petunia results in reversible co-suppression of homologous genes *in trans*," *Plant Cell*, Apr. 1990, 2, 279-289.
Nishikura, K., "A short primer on RNAi: RNA-directed RNA polymerase acts as a key catalyst," *Cell*, Nov. 16, 2001, 107, 415-418.
Parrish, S., et al., "Functional anatomy of a dsRNA trigger: differential requirement for the two trigger strands in RNA interference," Molecular Cell, Nov. 2000, 6, 1077-1087.
Schwarz, D.S., et al., "Evidence that siRNAs function as guides, not primers, in the *Drosophila* and human RNAi pathways," *Molecular Cell*, Sep. 2002, 10, 537-548.
Sijen, T., et al., "On the role of RNA amplification in dsRNA-triggered gene silencing," *Cell*, Nov. 16, 2001, 107, 465-476.
Tabara, H., et al., "RNAi in *C. elegans*: soaking in the genome sequence," *Science*, Oct. 16, 1998, 282, 430-431.
Tijsterman, M., et al., "RNA helicase MUT-14-dependent gene silencing triggered in *C. elegans* by short antisense RNAs," *Science*, Jan. 25, 2002, 295, 694-697.
Tinunons, L., et al., "Ingestion of bacterially expressed dsRNAs can produce specific and potent genetic interferences in *Caenorhabditis elegans*," *Gene*, 2001, 263, 103-112.
Timmons, L., et al., "Specific interference by ingested dsRNA," *Nature*, Oct. 29, 1998, 395, p. 854.
Tuschl, T., et al., "Targeted mRNA degradation by double-stranded RNA in vitro," *Genes & Dev.*, 1999, 13, 3191-3197.
Leydier, C. et al., "4'-Thio-RNA: Synthesis of Mixed Base 4'-Thio-Oligoribonucleotides, Nuclease Resistance, and Base Pairing Properties with Complementary Single and Double Strand," Antisense Research and Development, 1995, 5, 167-174.
Abe, A., et al., "Conformational energies and the random-coil dimensions and dipole moments of the polyoxides $CH3O[CH2)yO]xCH3$," J. Am. Chem. Soc., 1976, 98(21), 6468-6476.
Afonina, I. et al., "Sequence-specific arrest of primer extension on single-stranded DNA by an oligonucleotide-minor groove binder conjugate," Proc. Natl. Acad. Sci. USA (1996) 93:3199-3204.
Agarwal, et al., "Oligodeoxynucleoside Phosphoramidates and Phosphorothioates as Inhibitors of Human Immunodeficiency Virus" Proc. Natl. Acad. Sci. USA , 1988, 85, 7079-7083.
Agarwal, et al., "Synthesis and Enzymatic Properties of Deoxyribooligonucleotides Containing Methyl and Phenylphosphonate Linkages", Nucleic Acid Research 1979, 6, 3009-3024.
Agrawal, S. et al., "Antisense therapeutics: is it as simple as complementary base recognition?," Molecular Med. Today, vol. 6(2), pp. 72-81 (2000).
Agris, et al., "Inhibition of Vesicular Stomatitis Virus Protein Synthesis and Infection by Sequence-Specific Oligodeoxyribonucleoside Methylphosphonates", Biochemistry 1986, 25, 6268-6275.
Allerson, C.R. et al., Abstract of the 227th ACS National Meeting, Anaheim, CA, Mar. 28-Apr. 1, 2004.
Allerson, C.R. et al., "Fully 2'-Modified Oligonucleotide Duplexes with Improved in Vitro Potency and Stability Compared to Unmodified Small Interfering RNA," J. Med. Chem., 2005, 48, 901-904.
Altmann, K.-H. et al., "Second generation antisense oligonucleotides—inhibition of PKC-alpha and c-RAF kinase expression by chimeric oligonucleotides incorporating 6'-substituted carbocyclic nucleosides and 2'-O-ethylene glycol substituted ribonucleosides," Nucleosides & Nucleotides, 1997, 16(7-9), 917-926.
Altmann, K.-H., et al., "Second generation of antisense oligonucleotides: from nuclease resistance to biological efficacy in animals," Chimia, 1996, 50, 168-176.
Altmann, K.H., et al., "Second-generation antisense oligonucleotides: structure-activity relationships and the design of improved signal-transduction inhibitors," Biochem. Soc. Trans., 1996, 24, 630-637.
Altschul, S.F. et al., "Basic Local Alignment Search Tool," J. Mol. Biol., 1990, 215, 403-410.
Ambros, V. et al., "A uniform system for MicroRNA annotation," RNA (2003) 9: 277-279.
Ambros, V. et al., "MicroRNAs and Other Tiny Endogenous RNAs in *C. elegans*, "Curr Biol. (2003) 13: 807-818.
Ambros, V. et al., "MicroRNAs: Tiny Regulators with Great Potential," Cell (2001) 107: 823-826.
Antopolsky, M. et al., "Peptide-Oligonucleotide Phosphorothioate Conjugates with Membrane Translocation and Nuclear Localization Properties," Bioconjuxate Chem. (1999) 10(4):598-606.
Arar, K. et al., "Synthesis and Antiviral Activity of Peptide-Oligonucleotide Conjugates Prepared by Using Na-(Bromoaceytl)peptides," Bioconjugate Chem. (1995) 6(5):573-577.
Arnott, S., et al., "Optimised parameters for A-DNA and B-DNA," Biochem. & Biophys. Res. Comm., 1972, 47(6), 1504-1510.
Asseline, U. et al., "Nucleic acid-binding molecules with high affinity and base sequence specificity: Intercalating agents covalently linked to oligodeoxynucleotides," Proc. Natl. Acad. Sci USA (1984) 81: 3297-3301.
Astriab-Fisher et al., "Conjugates of antisense olgonucleotides with the TAT and antennapedia cell-penetrating peptides: effects on cellular update, binding to target sequences and biologic actions," Pharmaceutical Research (2002) 19(6): 744-754.
Astriab-Fisher, A. et al., "Antisense Inhibition of P-glycoprotein Expression Using Peptide-Oligonucleotide Conjugates," Biochem. Pharmacol. (2000) 60, 83-90.
Baker, B. F. et al., "Oligonucleotide-europium complex conjugate designed to cleave the 5'cap structure of the ICAM-I transcript potentiates antisense activity in cells," Nucleic Acids Res. (1999) 27(6):1547-1551.

(56) References Cited

OTHER PUBLICATIONS

Baker, B.F., et al., "2'-O-(2-methoxy)ethyl-modified anti-intercellular adhesion molecule 1 (ICAM-1) oligonucleotides selectively increase the ICAM-1 mRNA level and inhibit formation of the ICAM-1 translation initiation complex in human umbilical vein endothelial cells," J. Biol. Chem., 1997, 272(18), 11944-12000.
Bartel, B. et al., "MicroRNAs: At the Root of Plant Development," Plant Physiol. (2003) 132: 709-717.
Bayer, E. et al., "A New Support for Polypeptide Synthesis in Columns," Tetrahedron Letters, 1970, 51, 4503-4505.
Beaucage et al. "The Functionalization of Oligonucleotides Via Phosphoramidite Derivatives", (1993) Tetrahedron 49(10):1925-1963.
Beaucage S. and Iyer, R., "The synthesis of modified oligonucleotides by the phosphoramidite approach and their applications", Tetrahedron, 1993, 49, 6123-6194.
Beaucage, S.L. et al., "Deoxynucleoside Phosphoramidites—A New Class of Key Intermediates for Deoxypolynucleotide Synthesis,", Tetrahedron Letts., 1981, 22, 1859-1862.
Biggadike, et al., "Short convergent route to homochiral carbocyclic 2'-deoxynucleosides and carbocyclic robonucleosides", J. Chem. Soc. Chem. Commun. 1987, 1083-1084.
Bollig, F. et a]., "Affinity purification of ARE-binding proteins identifies poly(A)-binding protein 1 as a potential substrate in MK2-induced mRNA stabilization," Biochem. Bioophys. Res. Commun. (2003) 301: 665-670.
Bongartz, J.-P. et al., "Improved biological activity of antisense oligonucleotides conjugated to a fusogenic peptide," Nucleic Acids Res. (1994) 22(22):4681-4688.
Bonora, G. M. et al., "Antisense activity of an anti-HIV oligonucleotide conjugated to linear and branched high molecular weight polyethylene glycols," Farmaco (1998) 53:634-637.
Bonora, G. M. et al., "Biological Properties of Antisense Oligonucleotides Conjugated to—Different High-Molecular Mass Poly(Ethylen Glycols)," Nucleosides Nucleotides (1999) 18(6&7):1723-1725.
Bonora, G.M., et al., "A liquid-phase process suitable for large-scale synthesis of phosphorothioate oligonucleotides," Organic Process Res. & Develop., 2000, 225-231.
Borer, et al., "Stability of ribonucleic acid double-stranded helices," J. Mol. Biol., 1974, 86, 843-853.
Braasch et al., "Antisense inhibition of gene expression in cells by oligonucleotides incorporating locked nucleic acids: effect of mRNA target sequence and chimera design," Nucleic Acids Research, 2002, 30, 5160-5167.
Braasch, D.A. et al., "Locked nucleic acid (LNA): fine-tuning the recognition of DNA and RNA," Chem Biol, 2001, 8, 1-7.
Braasch, D.A. et al., "RNA Interference in Mammalian Cells by Chemically-Modified RNA," Biochemistry, 2003, 42, 7967-7975.
Braasch, D.A., et al., "Novel antisense and peptide nucleic acid strategies for controlling gene expression," Biochemistry, Apr. 9, 2002, 41(14), 4503-4510.
Branda et al., "Amplification of antibody production by phosphorothioate oligodeoxynucleotides," J. Lab. Clin. Med., 1996, 128(3), 329-338.
Branden, L. J. et al., "A peptide nucleic acid-nuclear localization signal fusion that mediates nuclear transport of DNA," Nature Biotech (1999) 17:784-787.
Brazma, A., et al., "Gene expression data analysis," FEBS Lett., 2000, 480, 17-24.
Brill, et al., "Synthesis of Oligodeoxynucleoside Phosphorodithioates Via Thioamidites", J. Am. Chem. Soc. 1989, 111, 2321-2322.
Brown-Driver et al., "Inhibition of Translation of Hepatitis C Virus RNA by 2'-Modified Antisense Oligonucleotides," Antisense Nucleic Acid Drug Dev. (1999) 9(2): 145-154.
Buhr, C.A. et al., "Oligodeoxynucleotides containing C-7 propyne analogs of 7-deaza-2'-deoxyguanosine and 7-deaza-2'-deoxyadenosine," Nucleic Acids Research, 1996, 24(15), 2974-2980.

Butke, et al., "Facile synthesis of 2'amino-2deoxynucleoside from the corresponding arabino derivative," Nucleic Acid Chemistry, 1986, Part Three, 149-152.
Butler, M. et al., "Specific Inhibition of PTEN Expression Reverses Hyperglycemia in Diabetic Mice," Diabetes, 2002, 51, 1028-1034.
Caplen et al., "dsRNA-mediated gene silencing in cultured Drosophila cells: a tissue culture model for the analysis of RNA interference," GENE (2000) 252: 95-105.
Carulli, J.P., et al., "High throughput analysis of differential gene expression," J. Cellular Biochem. Suppl., 1998, 30(31), 286-296.
Caruthers, M., "Synthesis of Oligonucleotides and Oligonucleotide Analogues", in "Oligonucleotides. Antisense Inhibitors of Gene Expression.", J.S. Cohen, Ed., CRC Press, Inc., 7-24, (1989).
Castle, et al., "Imidazo[4, 5-D]pyridazines. I. Synthesis of 4,7-disubstituted derivatives", Journal of Organic Chemistry, 1958, 23, 1534-1538.
Cazalla, D. et al., "Nuclear Export and Retention Signals in the RS Domain of SR Proteins," Mol. Cell. Biol. (2002) 22(19):6871-6882.
Cazenave, C. et al., "Enzymatic amplification of translation inhibition of rabbit β-globin mRNA mediated by anti-messenger oligodeoxynucleotides covalently linked to intercalating agents", Nucl. Acids Res., 1987, 15, 4717-4736.
Celis, J.E., et al., "Gene expression profiling: monitoring transcription and translation production using DNA microarrays and proteomics," FEBS Lett., 2000, 480, 2-16.
Cerutti, H., "RNA interference: traveling in the cell and gaining functions?" Trends in Genetics (2003) 19(1): 39-46.
Chaloin, L. et al., "Design of Carrier Peptide-Oligonucleotide Conjugates with Rapid Membrane Translocation and Nuclear Localization Properties," Biochem. Biophys. Res. Commun. (1998) 243:601-608.
Chaput, J.C., et al., "DNA polymerase-mediated DNA synthesis on a TNA template," J. Am. Chem. Soc., 2003, 125, 856-857.
Chen and Wu, "Studies on Fluoroalkylation and Fluroalkoxylation. Part 33. Direct Trifluoromethylation of Aryl Halides with Fluorosulphonyldifluoromethyl Iodide in the Presence of Copper: an Electron Transfer Induced Process," J. Chem. Soc., Perkin Transactions, 1989, 1, 2385-2387.
Chiang et al., "Antisense Oligonucleotides Inhibit Intercellular Adhesion Molecule 1 Expression by Two Distinct Mechanisms," J. Biol. Chem., 1991, 266, 18162-18171.
Chirila, T.V. et al., "The use of synthetic polymers for delivery of therapeutic antisense oligodeoxynucleotides," Biomaterials, vol. 23(2), pp. 321-342 (2002).
Chiu et al., "siRNA function in RNAi: a chemical modification analysis," RNA, 2003, 9, 1034-1048.
Chladek, et al., "Facile Synthesis of 2'Amino-2'Deoxyadenosine," J. Carbohydtrates, Necleosides & Nucleotides, 1980, 7, 63-75.
Choung, S. et al., "Chemical modification of siRNAs to improve serum stability without loss of efficacy," Biochemical and Biophysical Research Communications, 2006, 342, 919-927.
Christofferson et al., "Ribozymes as human therapeutic agents", J. Med. Chem., 1995, 38(12), 2023-2037.
Chun-Nam Lok et al., "Potent gene-specific inhibitory properties of mixed backbone antisense oligonucleotides comprised of 2'-deoxy-2'-fluoro-D-arabinose and 2'-deoxyribose nucleotides," Biochemistry, 2002, 41, 3457-3467.
Cohen, G. L. et al., "Sequence Dependent Binding of cis-Dichlorodiamrnineplatinum(II) to DNA," J. Am. Chem. Soc. (1980) 102(7), 2487-2488.
Constant et al., "Heterodimeric Molecules Including Nucleic Acid Bases and 9-Aminoacridine Spectroscopic Studies, Conformations, and Interactions with DNA", Biochemistry, 1988, 27, 3997-4003.
Conte, M.R., et al., "Conformational properties and thermodynamics of the RNA duplex r(CGCAAAUUUGCG)2: comparison with the DNA analogue d(CGCAAATTTGCG)2," Nucleic Acids Res., 1997, 25(13), 2627-2634.
PCT International Search Report dated Jan. 24, 2005 (PCTUS03/35087).
Corey, D. R. et al., "Generation of a Hybrid Sequence-Specific Single-Stranded Deoxyribonuclease," Science (1987) 238:1401-1403.

(56) References Cited

OTHER PUBLICATIONS

Corey, D. R. et al., "Sequence-Selective Hydrolysis of Duplex DNA by an Oligonucleotide-Directed Nuclease," J. Am. Chem. Soc. (1989) 111(22):8523-8525.
Corey, D. R., "48000-fold Acceleration of Hybridization by Chemically Modified Oligonucleotides," J. Am. Chem. Soc. (1995) 117(36):9373-9374.
Cornell, W. D. et al., "A Second Generation Force Field for the Simulation of Proteins, Nucleic Acids, and Organic Molecules," J. Am. Chem. Soc., 1995, 117, 5179-5197.
Cossum, P.A. et al., "Disposition of the 14C-Labeled Phosphorothioate Oligonucleotide ISIS 2105 after Intravenous Administration to Rats," J. Pharmacol. Exp. Ther., 1993, 267(3), 1181-1190.
Couzin, J., "Small TNAs Make Big Splash," Science (2002) 298: 2296-2297.
Crawford, J.M., "Role of Vesicle-Mediated Transport Pathways in Hepatocellular Bile Secretion," Semin. Liver Dis., 1996, 16(2), 169-189.
Crooke, S.T., Antisense Research & Application, Chapter 1, pp. 1-50, Publ. Springer-Verlag, Ed. S.T. Crooke (1998).
Cummins, L.L. et al., "Characterization of fully 2'modified oligoribonucleotide hetero- and homoduplex hybridization and nuclease sensitivity," Nucleic Acids Research, 1995, 23(11), 2019-2024.
Dahl, B.H. et al., "A Highly Reactive, Odourless Substitute for Thiphenol/Triethylmaine as a Deprotection Reagent in the Synthesis of Oligonucleotides and their Analogues," Acta Chem. Scand., 1990, 44, 639-641.
Damha, et al., "Solution and solid phase chemical synthesis of arabinonucleotides", Can J. Chem., 1989, 831-839.
Dande, P. et al., Abstract from The 227th ACS National Meeting, Anaheim, CA, Mar. 28-Apr. 1, 2004.
De las Heras, et al., "3'-C-Cyano-3'-Deoxythymidine," Tetrahedron Letters, 1988, 29, 941-944.
Dellinger, D.J. et al., "Solid-Phase Chemical Synthesis of Phosphonoacetate and Thiophosphonoacetate Oligodexynucleotides," J. Am. Chem. Soc., 2003, 125(4), 940-950.
Denny, W.A., "DNA-intercalating ligands as anti-cancer drugs: prospects for future design," Anti-Cancer Drug Design, 1989, 4, 241-263.
Dignam, et al., "Accurate transcription initiation by RNA polymerase II in a soluble extract from isolated mammalian nuclei," Nucleic Acids Res., 1983, 11, 1475-1489.
Divakar, et al., "Approaches to the Synthesis of 2'-Thio Analogues of Pyrimidine Ribosides", J. Chem. Soc., Perkins Trans., I, 1990, 969-974.
Divakar, et al., "Reaction Between 2,2'-Anhydro-1-β-D-arrabinofuranosyluracil and Thiolate Ions", J. Chem. Soc., Perkins Trans. I, 1982, 1625-1628.
Dreyer, et al., "Sequence-specific cleavage of single-stranded DNA: Oligodeoxynucleotide-EDTA-Fe(II)", Proc. Natl. Acad. Sci. USA, 1985, 82, 968-972.
Duff, R. J. et al., "[17] Intrabody Tissue-Specific Delivery of Antisense Conjugates in Animals: Ligand-Linker-Antisense Oligomer Conjugates," Methods Enzymol. (2000) 313:297-321.
Eckstein, et al., "Polynucleotides Containing 2'Chloro-2'Deoxyribose", Biochemistry, 1972, 11, 4336-4344.
Eddy, S.R., "Non-Coding RNA Genes and the Modern RNA World," Nature Rev. Genetics (2001) 2: 919-929.
Efimov, V. A. et al., "Synthesis of Polyethylene Glycol—Oligonucleotide Conjugates," Bioorg. Khim. (1993) 19(8):800-804.
Egli, M. et al., "RNA Hydration: A Detailed Look," Biochemistry, 1996, 35, 8489-8494.
Elayadi, A.N. et al., "Application of PNA and LNA oligomers to chemotherapy," Curr. Opin. Investig. Drugs, 2001, 2(4), 558-561.
Elmén, J. et al., "Locked nucleic acid (LNA) mediated improvements in siRNA stability and functionality," Nucleic Acids Res. 2005, 33(1), 439-447.
EP Supplementary Search Report for EP 03716922 dated May 12, 2006.

Faria, M. et al., "Phosphoramidate oligonucleotides as potent antisense molecules in cells and in vivo," Nature Biotech., 2001, 19, 40-44.
Fazakerley, G.V., et al., "A→Z transition in the synthetic hexanucleotide (dCdGfl)3," FEBS, 1985, 182(2), 365-369.
Fedoroff, O.Y. et al., "Structure of a DNA:RNA Hybrid Duplex," J. Mol. Biol., 1993, 233, 509-523.
Fieser, L. et al., Fieser and Fieser's Reagents for Organic Synthesis (1994), John Wiley & Sons, New York.
Fire et al., "RNA-triggered gene silencing," TIG (1999) 15(9): 358-363.
Firestone, R. A., "Low-Density Lipoprotein as a Vehicle for Targeting Antitumor Compounds to Cancer Cells," Bioconjugate Chem. (1994) 105-113.
Flanagan, W. M. et al., "A cytosine analog that confers enhanced potency to antisense oligonucleotides," Proc. Natl. Acad. Sci. USA, Mar. 1999, 96, 3513-3518.
Flanagan, W.M. et al., "Cellular penetration and antisense activity by a phenoxazine-substituted heptanucleotide," Nature Biotechnol. (1999) 17(1): 48-52.
Fluiter, K. et al., "In vivo tumor growth inhibition and biodistribution studies of locked nucleic acids (LNA) antisense oligonucleotides," Nucleic Acids Res., 2003, 31(3), 953-962.
Fox, et al., "Nucleosides. XVIII. Synthesis of 2'-Fluorothymidine, 2'-Flurodeoxyuridine, and Other 2'-Halogeno-2'-Deoxy Nucleosides 12", J Org. Chem., 1964, 29, 558-564.
Francis, A.W. et al., "Probing the Requirements for Recognition and Catalysis in Fpg and MutY with Nonpolar Adenine Isosteres," J. Am. Chem. Soc. (2003) 125(52): 16235-16242.
Fraser, A., et al., "Synthesis and conformational properties of 2'-deoxy-2'-methylthiopyrimidine and -purine nucleosides:potential antisense applications," J. Heterocycl. Chem., 1993, 30, 1277-1287.
Fraser, A.G. et al., "Functional genomic analysis of C. elegans chromosome 1 by systemic RNA interference," Nature, 2000, 408, 325-330.
Freier, S. M. et al., "The ups and downs of nucleic acid duplex stability: structure-stability studies on chemically-modified DNA:RNA duplexes," Nucleic Acids Research, 1997, 25(22), 4429-4443.
Freskos, "Synthesis of 2'Deoxypyrimidine Nucleosides Via Copper (I) Iodine Catalysis," Nucleosides & Nucleotides, 1989, 8, 1075, 1076.
Frieden, M. et al., Expanding the design horizon of antisense oligonucleotides with alpha-L-LNA, Nucleic Acids Res., 2003, 31(21), 6365-6372.
Fromageot, H.P.M. et al., "The Synthesis of Oligonucleotides," Tetrahedron, 1967, 23, 2315-2331.
Fuchs, B. et al., "Identification of Differentially Expressed Genes by Mutually Subtracted RNA Fingerprinting," Anal. Biochem., 2000, 286, 91-98.
Gaffney, et al., "A New Strategy for the Protection of eoxyguanosine During Oligonucleotide Synthesis," Tetrahedron Letters, 1982, 23, 2257-2260.
Gait, M.J. et al., "Application of chemically synthesized RNA," RNA: Protein Interactions (1998) Smith (ed.), pp. 1-36.
Gait, M.J., Oligoribonucleotides, Antisense Research and Applications, 1993, Crooke, S.T. and Lebleu, B. (eds.), CRC Press, Boca Raton, pp. 289-301.
Gallo, M. et al., "2'-C-Methyluridine phosphoramidite: a new building block for the preparation of RNA analogues carrying the 2'-hydroxyl group," Tetrahedron, 2001, 57(27), 5707-5713.
Gao, J. et al., "Expanded-Size Bases in Naturally Sized DNA: Evaluation of Steric Effects in Watson-Crick Pairing," J. Am. Chem. Soc. (2004) 126(38): 11826-11831.
Geary, R.S. et al., "Pharmacokinetic Properties of 2'-O-(2-Methoxyethyl)-Modified Oligonucleotide Analogs in Rats," J. Pharmacol. Exp. Therap., 1998, 296(3), 890-897.
Going, J.J., et al., "Molecular pathology and future developments," Eur. J. Cancer, 1999, 35(14), 1895-1904.
Gonzalez, C. et al., "Structure and Dynamics of a DNA-RNA Hybrid Duplex with a Chral Phosphorothioate Moiety: NMR and Molecular Dynamics with Conventional and Time-Averaged Restraints," Biochemistry, 1995, 34, 4969-4982.

(56) References Cited

OTHER PUBLICATIONS

Gorlach, M. et al., "The mRNA Poly(A)-Binding Protein: Localization, Abundance, and RNABinding Specificity," Exp. Cells Res. (1994) 211:400-407.

Graham, et al., "Tritium Labeling of Antisense Oligonucleotides by Exchange with Tritiated Water," Nucleic Acids. Res., 1993, 16, 3737-3743.

Graham, M.J. et al., "In Vivo Distribution and Metabolism of a Phosphorothioate Oligonucleotide within Rat Liver after Intravenous Administration," J. Pharmacol. Exp. Therap., 1998, 286(1), 447-458.

Gravert, D.J., et al., "Organic synthesis on soluble polymer supports," Chem. Rev., 1997, 97, 489-509.

Griffey, R.H. et al., "2'-O-Aminopropyl Ribonucleotides: A Zwitterionic Modification that Enhances the Exonuclease Resistance and Biological Activity of Antisense Oligonucleotides," J. Med. Chem., 1996, 39(26), 5100-5109.

Griffin, B.E. et al., "The Synthesis of Oligoribonucleotides," Tetrahedron, 1967, 23, 2301-2313.

Grishok, A. et al., "Genetic Requirements for Inheritance of RNAi in C. elegans," Science, 2000, 287, 2494-2497.

Grünweller, A. et al., "Comparison of different antisense strategies in mammalian cells using locked nucleic acids, 2'-O-methyl RNA, phosphorothioates and small interfering RNA," Nucleic Acids Research, 2003, 31(12), 3185-3193.

Gryaznov, S. et al., "Oligodeoxynucleotide N3'P5' Phosphoramidates: Synthesis and Hybridization Properties," J. Am. Chem. Soc., 1994, 116(7), 3143-3144.

Guckian, K.M. et al., "Structure and Base Pairing Properties of a Replicable Nonpolar Isostere for Deoxyadenosine," J Org Chem (1998) 63(26);9652-9656.

Guillerm, D. et al., "Synthesis of 4'-fluoroadenosine as an inhibitor of S-adenosyl-L-homocysteine hydrolase," Bioorganic & Medicinal Chemistry Letters, 1995, 5(14), 1455-1460.

Guschlbauer, et al., "Nucleoside conformation is Determined by the Electronegativity of the Sugar Substituent," Nucleic Acids Res., 1980, 8, 1421-1433.

Guschlbauer, W. et al., "Poly-2'-deoxy-2'-fluoro-cytidylic acid: enzymatic synthesis, spectroscopic characterization and interaction with poly-inosinic acid," Nucleic Acid Research, 1977, 4(6),1933-1943.

Guschlbauer, W., et al., "Use of 2'-deoxy-2'-fluoro-necleosides in the study of polynucleotide conformation: a progress report," Nucleic Acid Research Symposium Series, 1982, 11,113-116.

Gutierrez, A.J. et al., "Antisense Gene Inhibition by C-5 Substituted Deoxyuridine-Containing Oligodeoxynucleotides," Biochemistry, 1997, 36(4), 743-748.

Guzaev, A. et al., "Conjugation of Oligonucleotides Via an Electrophilic Tether: N-Chloroacetarnidohexyl Phosphoramidite Reagent," Bioorg. Med. Chem. lett . (1998) 8:3671-3676.

Hakimelahi, G.H. et al., "High Yield Selective 3'-Silylation of Ribonucleosides," Tetrahedron Lett., 1981, 22(52), 5243-5246.

Hall, J. et al., "Efficient sequence-specific cleavage of RNA using novel europium complexes conjugated to oligonucleotides," Chem. Biol. (1994) 1(3):185-190.

Hamada et al., "Effects on RNA Interference in Gene Expression (RNAi) in Cultured Mammalian Cells of Mismatches and the Introduction of Chemical Modifications at the 3'Ends of siRNAs," Antisense and Nucleic Acid Drug Development (2002) 12:301-309.

Hamilton et al., "A species of small antisense RNA in post-transcriptional gene silencing in plants," Science (1999) 286 (5441): 950-952.

Hansske, et al., "2'and 3'-ketonucleosides and their arabino and XYLO reduction products," Tetrahedron, 1984, 40, 125-135.

Hariton-Gazal, E. et al., "Targeting of Nonkaryophilic Cell-Permeable Peptides into the Nuclei of Intact Cells by Covalently Attached Nuclear Localization Signals," Biochemistry (2002) 41(29):9208-9214.

Harry O'Kuru, R.E. et al., "A Short, Flexible Route toward 2'-C-Branched Ribonucleosides," J. Org. Chem., 1997, 62(6), 1754-1759.

Heasman, J., "Morpholino Oligos: Making Sense of Antisense?" Dev. Biol., 2002, 243, 209-214.

Henderson, B. R. et al., "A Comparison of the Activity, Sequence Specificity, and CRM1-Dependence of Different Nuclear Export Signals," Exp. Cell Res. (2000) 256:213-224.

Hertel, et al., "Synthesis of 2-deoxy-2,2-difluoro-D-ribose and 2-deoxy-2,2-difluoro-D-ribofuranosyl nucleosides," J. Org. Chem., 1988, 53, 2406-2409.

Hill, F. et al., "Polymerase recognition of synthetic oligodeoxyribonucleotides incorporating degenerate pyrimidine and purine bases," Proc. Natl. Acad. Sci. USA, 1998, 95, 4258-4263.

Hoffman, K., "Imidazole and its Derivatives" in The Chemistry of Heterocyclic Compounds, Weissberger, A., Ed.,Interscience Publishers, Inc., New York, 1953, 447.

Holen, T., et al., "Similar behaviour of single-strand and double-strand siRNAs suggests they act through a common RNAi pathway," Nucleic Acids Res., 2003, 31(9), 2401-2407.

Hornbeck, P. et al., Enzyme-Linked Immunosorbet Assays (ELIASE), Curr. Protocols Mol. Biol., 1991, John Wiley & Sons, pp. 11.2.1-11.2.22.

Hornung, V. et al., "Sequence-specific potent induction of IFN-a by short ineterfering RNA in plasmacytoid dendritic cells through TLR7," Nature Med., 2005, 11(3), 263-270.

Horton, N. C. et al., "The Structure of an RNA/DNA Hybrid: A Substrate of the Ribonuclease Activity of HIV-1 Reverse Transcriptase," J. Mol. Biol., 1996, 264, 521-533.

Huang, L. et al., "Oligonucleotide conjugates of Eu(III) tetraazamacrocycles with pendent alcohol and amide groups promote sequence-specific RNA cleavage," J Biol Inorg. Chem (2000) 5:85-92.

Huh, N. et al., "Design, Synthesis, and Evaluation of Mitomycin-Tethered Phosphorothioate Oligodeoxynucleotides," Bioconjugate Chem. (1996) 7:659-669.

Hunter, "Genetics: a touch of elegance with RNAi," Current Biology, Current Science (1999) 9(12): R440-R442.

Ikehara, et al, "Studies of Nucleosides and Nucleotides-LXV' Purine Cyclonucleosides-26 A Versatile Method for the Synthesis of Purine O-Cyclo-Bucleosides. The First Synthesis of 8,2'Anhydro-8-Oxy 9-B-D-Arabinofuranosylguanine," Tetrahedron, 1975, 31, 1369-1372.

Ikehara, et al, "Studies of Nucleosides and Nucleotides-LXXXVII. 1, Purine Cyclonucleosides. XLII. Synthesis of 2'deoxy-2'fluorofunaosine," Chem. and Pharm. Bull., 1981, 29, 1034-1038.

Ikehara, et al. "Purine cyclonucleosides. (43). Synthesis and properties of 2'halogen-2'deoxyguanosines 1," Chem and Pharm Bull., 1981, 29, 3281-3285.

Ikehara, et al., "A Linear Relationship Between Electronegativity of 2'-Substituents and Conformation of Adenine Nucleosides," Tetrahedron Letters, 1979, 42, 4073-4076.

Ikehara, et al., "Improved Synthesis of 2'-fluoro-2'deoxyadenosine and Synthesis and Carbon-13 NMR Spectrum of its 3',5'-cyclic Phosphate Derivative," Nucleosides & Nucleotides, 1983, 2, 373-385.

Ikehara, et al., "Polynucleotides. L. synthesis and properties of poly (2'chloro-2'-deoxyadenylic acid) and poly (2'-bromo-2'-deoxyadenylic acid)", Nucleic Acids Res., 1978, 4, 4249-4260.

Ikehara, et al., "Polynucleotides. LII. Synthesis and properties of poly (2'-deox-2'-fluoroadenylic acid)," Nucleic Acids Research, 1978, 5, 1877-1887.

Ikehara, et al., "Polynucleotides. LVI. Synthesis and Properties of Poly(2'-deoxy-2'-fluoroinosinic Acid)", Nucleic Acids Res., 1978, 5, 3315-3324.

Ikehara, et al., "Purine 8-Cyclonucleosides," Accts. Chem Res., 1969, 2, 47-53.

Ikehara, et al., "Studies of Nucleosides and Nucleotides-LXXIV1 Purine Cyclonucleosides-34 A New Method for the Synthesis of 2'-substituted 2'-deoxyadenosines," Tetrahedron, 1978, 34, 1133-1138.

Ikehara, et al., "Studies of Nucleosides and Nucleotides—LXXXII. 1 Cyclonucleosides. (39). 2 Synthesis and properties of 2'halogen-2'-deoxyadenosines," Chem. Pharm. Bull., 1978, 26, 2449-2453.

Ikehara, M., "2'-substituted 2'-deoxypurineucleotides their conformation and properties," Heterocycles, 1984, 21(1), 75-90.

Imazawa, et al., "Nucleosides and nucleotides. XII.1) Synthesis and properties of 2'-deoxy-2'-mercaptouridine and its derivates", Chem. Pharm. Bull., 1975, 23, 604-610.

(56) References Cited

OTHER PUBLICATIONS

Inoue et al., "Sequence dependent hydrolysis of RNA using modified oligonucleotide splints and Rnase H", FEBS Lett., 1987, 215(2), 327-330.
Inoue, et al., "Synthesis and hybridization studies on two complementary nona(2'-O-methyl) ribonucleotides", Nucleic Acid Res., 1987, 15, 6131-6148.
International Search Report Dated Aug. 23, 2004 for International Application No. PCT/US03/09808.
International Search Report dated Mar. 24, 2005 for International Application No. PCT/US03/35088.
International Search Report dated Nov. 18, 2004 for International Application No. PCT/US03/29294.
Jacobson, K.A. et al., "Methanocarba Analogues of Purine Nucleosides as Potent and Selective Adenosine Receptor Agonists," J. Med. Chem., 2000, 43(11), 2196-2203.
Jäger, A. et al., "Oligonucleotide N-alkylphosphoramidates: Synthesis and binding to polynucleotides", Biochemistry 1988, 27, 7237-7246.
Janik, B., et al., "Synthesis and Properties of Poly 2'-Fluoro-2'-Deoxyuridylic Acid," Biochem. Biophys. Res. Comm., 1972, 46(3), 1153-1160.
Jarvi, et al., "Synthesis and biological evaluation of dideoxunucleosides containing a difluoromethylene unit", Nucleosides & Nucleotides, 1989, 8, 1111-1114.
Jaschke, A. et al., "Synthesis and properties of oligodeoxyribonucleotide-polyethyleneg lycol conjugates," Nucleic Acids Res. (1994) 22(22):4810-4817.
Jayaraman, et al., "Selective Inhibition of *Escherichia coli* Protein Synthesis and Growth by Nonionic Oligonucleotides Complementary to the 3' end of 16S rRNA", Proc. Natl. Acad. Sci. USA 1981, 78(3), 1537-1541.
Jen et al., "Suppression of Gene Expression by Targeted Disruption of Messenger RNA: Available Options and Current Strategies," Stem Cells, 2000, 18, 307-319.
Jones, et al., "4'-substituted nucleosides. 5. hydroxymethylation of nucleoside 5'-aldehydes", J. Org. Chem., 1979, 44, 1309-1317.
Jones, et al., "Transient protection: Efficient one-flask synthesis of protected deoxynucleosides", J. Am. Chem. Soc., 1982, 104, 1316-1319.
Jones, L.J. et al., "RNA Quantitation by Fluorescence-Based Solution Assay: RiboGreen Reagent Characterization," Anal. Biochem., 1998, 265, 368-374.
Jones, S.S. et al., "Migration of t-Butyldimethylsilyl Protecting Groups," J.C.S. Perkin 1, 1979, 2762-2764.
Juby, C. D. et al., "Facile Preparation of 3'0ligonucleotide-Peptide Conjugates," Tetrahedron Letters (1991) 32(7):879-882.
Jungblut, P.R., et al., "Proteomics in human disease: cancer, heart and infectious diseases," Electrophoresis, 1999, 20, 2100-2110.
Jurecic, R., et al., "Long-distance DD-PCR and cDNA microarrays," Curr. Opin. Mocrobiol., 2000, 3, 316-321.
Kabanov, A.V.,"A new class of antivirals: antisense olgonucleotides combined with a hydrophobic substituent effectively inhibit influenza virus reproduction and synthesis of virus-specific proteins in MDCK cells", FEBS Letts., 1990, 259, 327-330.
Kawasaki, H/ et al., "Hesl is a target of MicroRNA-23 during retinoic-acid-induced neuronal differentiation of NT2 cells," Nature (2003) 423: 838-842.
Khurshid et al., "The unique conformational stability of poly 2'-O-Ethyladenylic Acid," FEBS Letters, 1972, 28(1), 25.
Khvorova, A. et al., "Functional siRNAs Exhibit Strand Bias," Cell, 2003, 115(2), 209-216.
Kiaris, H. et al., "Antagonists of Growth Hormone-Releasing Hormone Inhibit the Growth of U-87MG Human Gliobastoma in Nude mice," Neoplasia, 2000, 2(3), 242-250.
Kielanowska et al., "Preparation and properties of poly 2'-O-ethylcytidylic acid," Nucl. Acids Res., 1976, 3(3), 817-824.
Kingston, R.E. et al., "Calcium Phosphate Transfection", Current Protocols in Neuroscience, 1997, Supplement 1, A.1C.1-A.1C.8.

Klopffer, A.E. et al., "Synthesis of 2'-Aminoalkyl-Substituted Fluorinated Nucleobases and Their Influence on the Kinetic Properties of Hammerhead Ribozymes," ChemBioChem (2004) 5: 707-716.
Klopffer, A.E. et al., "The effect of universal fluorinated nucleobases on the catalytic activity of ribozymes ," Nucleosides Nucleotides Nucleic Acids (2003) 22(5-8): 1347-1350.
Knorre, et al., "Complementary-Addressed Sequence-Specific Modification of Nucleic Acids", Progress in Nucleic Acid Research and Molecular Biology 1985, 32, 291-321.
Koole, et al., "Synthesis of phosphate-methylated DNA fragments using 9-fluorenylmethoxycarbonyl as transient base protecting group", J. Org. Chem., 1989, 54, 1657-1664.
Koshkin, A.A., et al., "LNA (locked nucleic acid): an RNA mimic forming exceedingly stable LNA:LNA duplexes," J. Am. Chem. Soc., 1998, 120, 13252-13253.
Koshkin, A.A., et al., "LNA (locked nucleic acids): synthesis of the adenine, cytosine, guanine, 5-methylcytosine, thymine and uracil bicyclonucleoside monomers, oligomerisation, and unprecedented nucleic acid recognition," Tetrahedron, 1998, 54, 3607-3630.
Kraynack, B.A. et al., "Small interfering RNAs containing full 2'-O-methylribonucleotide-modified sense strands display Argonaute2/eIF2C2-dependent activity," RNA, 2006, 12, 163-176.
Krieg, A. M. et al., "Uptake of Oligodeoxyribonucleotides by Lymphoid Cells Is Heterogeneous and Inducible," Antisense Research and Development (1991) 1:161-171.
Kroschwitz, J.I. (Ed.), The Concise Encyclopedia of Polymer Science and Engineering, John Wiley & Sons, 1990, 858-859.
Krug, A., et al., "Synthesis of oligonucleotide probes containing 2'-deoxy-2'-fluoronucleosides for cleavage of RNA by RNase H," Biomed. Biochem. Acta, 1990, 49, 161-166.
Krug, A., et al., "The behaviour of 2'-deoxy-2'-fluorouridine incorporated into oligonucleotides by the phosphoramidite approach," Nucleosides & Nucleotides, 1989, 8(8), 1473-1483.
Kuijpers, W. H. A. et al., "Specific Recognition of Antibody-Oligonucleotide Conjugates by Radiolabeled Antisense Nucleotides: A Novel Approach for Two-Step Radioimmunotherapy of Cancer," Bioconjugate Chem. (1993) 4(1):94-102.
Kumar et al., "Antisense RNA: function and fate of duplex RNA in cells of higher eukaryotes," Microbiology and Molecular Biology Reviews (1998) 62(4): 1415-1434.
Kumar, R., et al., "The first analogues of LNA (locked nucleic acids): phosphorothioate-LNA and 2'-thio-LNA," Bioorg. Med. Chem. Lett., 1998, 8, 2219-2222.
Kurchavov, N.A., et al., "A new phosphoramidite reagent for the incorporation of diazaphenoxazinone nucleoside with enhanced base-pairing properties into oligodeoxynucleotides," Nucleosides and Nucleotides, 1997, 16, 1837-1846.
Kurreck, J., "Antisense technologies, Improvement through novel chemical modifications," Eur. J. Biochem., 2003, 270(8), 1628-1644.
Kusmierek et al., "Alkyation of cytidine-5'-phosphate: Mechanisms of alkylation, influence of O'-alkylation on susceptibility of pyrimidine nucleotides to some nucleolytic enzymes, and synthesis of 2'-O-alkyl polynucleotides," ACTA Biochim. Polonica, 1973, 20(4), 365-381.
Lacerra, G., et al., "Restoration of hemoglobin a synthesis in erythroid cells from peripheral blood of thalassemic patients," Proc. Natl. Acad. Sci. USA, Aug. 15, 2000, 97(17), 9591-9596.
Lai J. S. et al., "Fluorinated DNA Bases as Probes of Electrostatic Effects in DNA Base Stacking," Angew. Chem. Int. Ed. (2003) 42: 5973-5977.
Lai, J. S. et al., "Selective Pairing of Polyfluorinated DNA Bases," J. Am. Chem. Soc. (2004) 126(10): 3040-3041.
Lane, A. N. et al., "NMR Assignments and Solution Conformation of the DNA-RNA Hybrid Duplex d(GTGAACTT)-r(AAGUUCAC)," Eur. J. Biochem., 1993, 215, 297-306.
Larson, E.J., et al., "Rapid DNA fingerprinting of pathogens by flow cytometry," Cytometry, 2000, 41, 203-208.
Larsson, M., et al., "High-throughput protein expression of cDNA products as a tool in functional genomics," J. Biotechnol., 2000, 80, 143-157.
Le Doan et al., "Sequence-Targeted Chemical Modifications of Nucleic Acids by Complementary Oligonucleotides Covalently Linked to Porphyrins", Nucleic Acid Research, 1987, 15, 8643-8659.

(56) References Cited

OTHER PUBLICATIONS

Lee, R.C. et al., "The *C. elegans* heterochronic gene lin-4 encodes small RNAs with antisense complementarity to lin-14," Cell, 1993, 75(5), 843-854.

Lee, K. et al., "Ring-Constrained (N)-Methanocarba Nucleosides as Adenosine Receptor Agonists: Independent 5'-Uronamide and 2'-Deoxy Modifications," Bioorganic & Medicinal Chemistry Letters, 2001, 11(10), 1333-1337.

Lee, Y. et al., "MicroRNA maturation: stepwise processing and subcellular localization," EMBO J. (2002) 21(17): 4663-4670.

Lee, Y. et al., "The nuclearRNase III Drosha initiates microRNA processing," Nature (2003) 425: 415-419.

Leeds, J.M. et al., "Pharmacokinetic Properties of Phosphorothioate Oligonucleotides," Nucleosides Nucleotides, 1997, 16(7-9), 1689-1693.

Letsinger et al., "Effects of Pendant Groups at Phosphorus on Binding Properties of D-ApA Analogues", Nucleic Acids Research, 1986, 14, 3487-3499.

Letsinger, R.L. et al., "Cholesteryl-conjugated oligonucleotides: Synthesis, properties and activity as inhibitors of replication of human immunodeficiency virus in cell culture", Proc. Natl. Acad. Sci.,1989, 86, 6553-6556.

Lewis, D.L. et al., "Efficient delivery of siRNA for inhibition of gene expression in postnatal mice," Nature Genetics, 2002, 32, 107-108.

Li, S. et al., "Folate-Mediated Targeting of Antisense Oligodeoxynucleotides to Ovarian Cancer Cells," Pharm. Res. (1998) 15(10):1540-1545.

Lima, W. F. et al., "Highly efficient endonucleolytic cleavage of RNA by a CyszHisz zinc-finger peptide," Proc. Natl. Acad. Sci. USA (1999) 96:10010-10015.

Lima, W.F. et al., "Binding affinity and specificity of *Escherichia coli* RNase H1: impact on the kinetics of catalysis of antisense oligonucleotide-RNA hybrids," Biochemistry, vol. 36, pp. 390-398 (1997).

Limbach, P.A. et al., "Summary: the modified nucleosides of RNA," Nucleic Acids Res., 1994, 22(12), 2183-2196.

Lin, K.-Y. et al., "A Cytosine Analogue Capable of Clamp-Like Binding to a Guanine in Helical Nucleic Acids," J. Am. Chem. Soc., 1998, 120(33), 8531-8532.

Lin, K.-Y. et al., "Tricyclic 2'-Deoxycytidine Analogs: Synthesis and Incorporation into Oligodeoxynucleotides Which Have Enhanced Binding to Complementary RNA," J. Am. Chem. Soc., 1995, 117, 3873-3874.

Lin, M. et al., "Inhibition of collagenase type I expression by psoralen antisense oligonucleotides in dermal fibroblasts," Faseb J. 1995, 9, 1371-1377.

Liu, H. et al."A Four Base Paired Genetic Helix with Expanded Size," Science (2003) 302; 868-871.

Liu, H. et al., "Toward a New Genetic System with Expanded Dimensions: Size-Expanded Analogues of Deoxyadenosine and Thymidine," J. Am Chem Soc. (2004) 126(4) 1102-1109.

Liu, K. et al., "Efficient Nuclear Delivery of Antisense Oligodeoxynucleotides and Selective Inhibition of CETP Expression by Apo E Peptide in a Human CETP-Stably Transfected CHO Cell Line," Arterioscler. Thromb. Vasc. Biol. (1999) 19:2207-2213.

Lixin, R. et al., "Novel Properties of the Nucleolar Targeting Signal of Human Angiogenin," Biochem. Biophys. Res. Comm. (2001) 284:185-193.

Loakes, D. et al., "The applications of universal DNA base analogues," Nucleic Acids Res., 2001, 29(12), 2437-2447.

Lukhtanov, E. A. et al., "Direct, Solid Phase Assembly of Dihydropyrroloindole Peptides with Conjugated Oligonucleotides," Bioconjugate Chem. (1996) 7(5):564-567.

Madden, S.L., et al., "Serial analysis of gene expression: from gene discovery to target identification," Drug Discov. Today, Sep. 2000, 5(9), 415-425.

Mahato et al., "Modulation of gene expression by antisense and antigene oligodeoxynucleotides and small interfering RNA," Expert Opinion on Drug Delivery, Jan. 2005, 2(1), 3-28.

Manche et al., "Interactions between double-stranded RNA regulators and the protein kinase DAI," Mol. Cell Biol., 1992, 12(11), 5238-5248.

Manoharan M. et al., "Cholic Acid-Oligonucliotide Conjugates for Antisense Applications", Bioorganic Med. Chem. Letts., 1994, 4, 1053-1060.

Manoharan M. et al., "Oligonucleotide Conjugates: Alteration of the Pharmacokinetic Properties of Antisense Agents", Nucleosides and Nucleotides, 1995, 14, 969-973.

Manoharan, M. et al., "Chemical Modifications to Improve Uptake and Bioavailability of Antisense Oligonucleotides", Annals NY Acad. Sciences, 1992, 660, 306-309.

Manoharan, M. et al., "Introduction of a Lipophilic Thioether Tether in the Minor Groove of Nucleic Acids for Antisense Applications", Bioorg. Med. Chem. Letts., 1993, 3, 2765-2770.

Manoharan, M. et al., "Novel Functionalization of the Sugar Moiety of Nucleic Acids for Multiple Labeling in the Minor Groove," Tetrahedron Letters (1991) 32(49):7171-7174.

Manoharan, M. et al., "Lipidic Nucleic Acids", Tetrahedron Letts., 1995, 36, 3651-3654.

Manoharan, M., "2'-Carbohydrate modifications in antisense oligonucleotide therapy: importance of conformation, configuration and conjugation," Biochimica et Biophysica Acta, 1999, 1489, 117-130.

Manoharan, M., "Designer Antisense Oligonucleotides: Conjugation Chemistry and Functionality Placement," Antisense Research and Applications, Crooke and Lebleu, eds., CRC Press Boca Raton. FL, 1993, Chapter 17, 303-349.

Manoharan, M., "Oligonucleotide Conjugates as Potential Antisense Drugs with Improved Uptake, Biodistribution, Targeted Delivery and Mechanism of Action," Antisense & Nucleic Acid Drug Development (2002) 12:103-128.

Manoharan, M., "Oligonucleotide Conjugates in Antisense Technology," Antisense Drug Technology, Principles, Strategies, and Applications, Crooke, S. T. ed., Marcel Dekker, New York, (2001) Chapter 16, 391-467.

Manoharan, M., "RNA interference and chemically modified small interfering RNAs," Current Opinion in Chemical Biology, 2004, 8, 570-579.

Marcus-Sekura, "Comparative inhibition of chloramphenicol acetyltransferase gene expression by antisense oligonucleotide analogues having alkyl phosphotriester, methylphosphonate and phosphorothioate linkages", Nucleic Acids Res., 1987, 15, 5749-5763.

Marcus-Sekura, "Techniques for Using Antisense Oligodeoxyribonucleotides to Study Gene Expression", Anal. Biochemistry, 1988, 172, 289-295.

Markiewicz, et al., "Simultaneous Protection of 3'- and 5'-Hydroxyl Groups of Nucleosides", Nucleic Acid Chemistry, Part 3, pp. 229-231, L.B. Townsend, et al., Eds., J. Wiley and Sons, New York, 1986, 229-231.

Maruenda, H. et al., "Antisense Sequence-Directed Cross-Linking of DNA Oligonucleotides by Mitomycin C," Bioconjugate Chem. (1996) 7(5):541-544.

Maruenda, H. et al., "Antisense sequence-directed cross-linking of RNA oligonucleotides by mitomycin," Anti-Cancer Drug. Des. (1997) 12, 473-479.

Marwick, C., "First "Antisense" Drug Will Treat CMV Retinitis," J. Am. Med. Assoc., 1998, 280(10), 871.

Matsukura, M. et al., "Phosphorothioate Analogs of Oligodeoxynucleotides: Inhibitors of Replication and Cytopathic Effects of Human Immunodeficiency Virus", Proc. Natl. Acad. Sci. USA, 1987, 84, 7706-7710.

Matteucci, M.D. et al., "Synthesis of Deoxyoligonucleotides on a Polymer Support," J. Am. Chem. Soc., 1981, 103(11), 3185-3191.

McCaffery, A.P. et al., "RNA interference in adult mice," Nature, 2002, 418, 38-39.

McIntyre, K.W. et al., "A Sense Phosphorothioate Oligonucleotide Directed to the Initiation Codon of Transcription Factor NF-kB p65 Causes Sequence-Specific Immune Stimulation," Antisense Res. Dev., 1993, 3, 309-322.

McQueen, C.A. et al., "Effect of Nalidixic Acid on DNA Repair in Rat Hepatocytes," Cell Biol. Toxicol., 1989, 5(2), 201-206.

(56) References Cited

OTHER PUBLICATIONS

Meunier, L. et al., "The nuclear export signal-dependent localization of oligonucleopeptides enhances the inhibition of the protein expression from a gene transcribed in cytosol," Nucleic Acids Res. 1999, 27(13):2730-2736.

Meyer, et al., "Efficient, Specific Cross-Linking and Cleavage of DNA by Stable, Synthetic Complementary Oligodeoxynucleotides", J. Am. Chem. Soc. 1989, 111, 8517-8519.

Mili, S. et al., "Distinct RNP Complexes of Shuttling hnRNP Proteins with Pre-mRNA and mRNA. Candidate Intermediates in Formation and Export of mRNA," Mol. Cell Biol. (2001) 21(21):7307-7319.

Miller, et al., "A New Approach to Chemotherapy Based on Molecular Biology and Nucleic Acid Chemistry: Matagen (Masking Tape for Gene Expression", Anti-Cancer Drug Design, 1987, 2, 117-128.

Miller, et al., "Biochemical and Biological Effects of Nonionic Nucleic Acid Methylphosphonates", Biochemistry 1981, 20, 1874-1880.

Miller, et al., "Nonionic nucleic acid analogues. Synthesis and characterization of dideoxyribonucleoside methylphosphonates", Biochemistry 1979, 18, 5134-5143.

Miller, et al., "Synthesis and properties of adenine and thymine nucleoside alkyl phosphotriesters, the neutral analogs of dinucleoside monophosphates", J. Am. Chem. Soc. 1971, 93, 6657-6664.

Min, K.-L. et al., "Oligonucleotides comprised of alternating 2'-deoxy-2'-fluoro-beta-D-arabinonucleosides and D-2'-deoxyribonucleosides (2'F-ANA/DNA 'Altimers') induce efficient RNA cleavage mediated by RNase H," Bioorganic & Medicinal Chemistry Letters, Sep. 2002, 12, 2651-2654.

Mishra et al., "Improved leishmanicidal effect of phosphorotioate antisense oligonucleotides by LDL-medicated delivery", Biochim. Biophys. Acta, 1995, 1264, 229-237.

Miura et al., "Fluorometric determination of total mRNA with oligo(dT) immobized on microtiter plates", Clin. Chem., 1996, 42(11), 1758-1764.

Moran, S. et al., "A thymidine triphosphate shape analog lacking watson-crick pairing ability is replicated with high sequence selectivity," Proc. Natl. Acad. Sci. USA (1997) 94, 10506-10511.

Moran, S. et al., "Difluorotoluene, a Nonpolar Isostere for Thymine, Codes Specifically and Efficiently for Adenine in DNA Replication," J Am Chem Soc. (1997) 119(8), 2056-2057.

Morita, K. et al., "2'-O,4'-C-Ethylene-Bridged Nucleic Acids (ENA): Highly Nuclease-Resistant and Thermodyamically Stable Oligonucleotides for Antisense Drug," Bioorganic & Medicinal Chemistry Letters, 2002, 12(1), 73-76.

Morita, K. et al., "Synthesis and Properties of 2'-O,4'-C-Ethylene-Bridged Nucleic Acids (ENA) as Effective Antisense Oligonucleotides," Bioorg. Med. Chem., 2003, 11, 2211-2226.

Moulds, C. et al., "Site and Mechanism of Antisense Inhibition by C-5 Propyne Oligonucleotides," Biochemistry, 1995, 34(15), 5044-5053.

Nasevicius, A. et al., "Effective targeted gene 'knockdown' in zebrafish," Nature Genetics, 2000, 26, 216-220.

Nelson, P. S. et al., "Bifunctional oligonucleotide probes synthesized using a novel CPG support are able to detect single base pair mutations," Nucleic Acids Res. (1989) 17(18):7187-7194.

Nestle, F.O. et al., "Cationic Lipid is not Required for Uptake and Selective Inhibitory Activity of ICAM-1 Phosphorothioate Antisense Oligonucleotides in Keratinocytes," J. Invest. Dermatol., 1994, 103, 569-575.

Nielsen et al., "Sequence-Selective Recognition of DNA by Strand Displacement with a Thymine-Substituted Polyamide", Science, 1991, 254, 1497-1500.

Nykänen, A. et al, "ATP Requirements and Small Interfering RNA Structure in the RNA Interference Pathway," Cell, 2001, 107, 309-321.

Oberhauser et al., "Effective incorporation of 2'-O-methyl-oligonucleotides into liposomes and enhanced cell association through modification with thiocholesterol", Nucl. Acids Res., 1992, 20(3), 533-538.

Ogilvie, K.K. et al., "The Use of Silyl Groups in Protecting the Hydroxyl Functions of Ribonucleosides," Tetrahedron Letters, 1974, 15(33), 2861-2863.

Ohtsuka et al., "Recognition by Restriction Endonuclease EcoRI of Deoxyoctanucleotides containing modified sugar moieties," Eur. J. Biochem., Mar. 1984, 447-450.

Olie, R.A. et al., "Analysis of ribosyl-modified, mixed backbone analogs of a bcl-2/bcl-xL antisense oligonucleotide," Biochimica et Biophysica Acta, 1576 (2002), 101-109.

Olsen, D.B., et al., "Study of a Hammerhead Ribozyme Containing 2'-Modified Adenosine Residues," Biochemistry, 1991, 30:, 9735-9741.

O'Neill, B.M. et al., "A Highly Effective Nonpolar Isostere of Deoxyguanosine: Synthesis, Structure, Stacking, and Base Pairing," J. Org. Chem. (2002) 67(17):5869-5875.

Opalinska et al., "Nucleic-acid therapeutics: basic principles and recent applications," Nature Review, 2002, 1, 503-514.

Ørum, H. et al., "Locked nucleic acids: A promising molecular family for gene-function analysis and antisense drug development," Curr. Opin. Mol. Therap., 2001, 3(3), 239-243.

Outten, et al., "Synthetic 1-methoxybenzo[d]naphtho[1,2-b]pyran-6-one c-glycosides", J. Org. Chem. 1987, 52, 5064-5066.

Owen, et al., "Transcriptional activation of a conserved sequence element by ras requires a nuclear factor distinct from c-fos or c-jun", Proc. Natl. Acad. Sci USA, 1990, 87, 3866-3870.

Owen, G.R. et al., "4'-Substituted Nucleosides. 3. Synthesis of Some 4'-Fluorouridine Derivatives," J. Org. Chem., 1976, 41(18), 3010-3017.

Parker, J.S. et al., "Structure insights into mRNA recognition from a PIWI domain-siRNA guide complex," Nature, 2005, 434, 663-666.

Parkes, et al., "A short synthesis of 3'-cyano-3'-Deoxythymidine", Tetra. Lett., 1988, 29, 2995-2996.

Parr, W. et al., "Solid-Phase Peptide Synthesis on an Inorganic Matrix having Organic Groups on the Surface," Angew Chem. Internat. Edit, 1972, 11 (4), 314-315.

Patzel et al., "A Theoretical Approach to Select Effective Antisense Oligodeoxyribonucleotides at High Statistical Probability," Nucleic Acids Research (1999) pp. 4328-4334.

Peracchi, A., "Prospects for antiviral ribozymes and deoxyribozymes," Rev. Med. Virol., vol. 14, pp. 47-64 (2004).

Petersen, M. et al., "The conformations of locked nucleic acids (LNA)," J. Mol. Recognit., 2000, 13, 44-53.

Petersheim, et al., "Base-Stacking and Base-Pairing contributions to helix stability: thermodynamics of double-helix formation with CCGG, CCGGp, CCGGAp, ACCGGp, CCGGUp, and ACCGGUp", Biochemistry, 1983, 22, 256-263.

Pichon, C. et al., "Intracellular Routing and Inhibitory Activity of Oligonucleopeptides Containing a KDEL Motif," Mol. Pharmacol. (1997) 51:431-438.

Pieken, W.A., et al., "Structure-Function Relationship of Hammerhead Ribozymes as Probed by 2'-Modifications," Nucleic Acids Symp Ser., 1991, 24, 51-53.

Pike et al., "Mixed Alkylation (Methylation and Ethylation) of Adenosine by Diazoethane in Aqueous 1,2-Dimethoxyethane," J. Org. Chem., 1974, 39(25), 3674-3676.

Pitts, A.E. et al., "Inhibition of human telomerase by 2'-O-methyl-RNA," Proc. Natl. Acad. Sci. USA, 1998, 95, 11549-11554.

Poopeiko, N.E. et al., "Xylo-configured Oligonucleotides (XNA, Xylo Nucleic Acid): Synthesis of Conformationally Restricted Derivatives and Hybridization Towards DNA and RNA Complements," Biorganic & Medicinal Chemistry Letters 2003, vol. 13, pp. 2285-2290.

Prakash, T. P. et al., Abstract of The 227th ACS National Meeting, Anaheim,CA, Mar. 28-Apr. 1, 2004.

Prakash, T. P. et al., "Synthesis of Site-Specific Oligonucleotide-Polyamine Conjugates," Bioorg. Med. Chem. Lett. (1994) 4(14):1733-1738.

Prashar, Y., et al., "A method for display of 3'-end fragments of restriction enzyme-digested cDNAs for analysis of differential gene expression," Methods Enzymol., 1999, 303, 258-272.

Puglisi, et al., "Absorbance melting curves of RNA", Methods in Enzymology, 1989, 180, 304-325.

(56) References Cited

OTHER PUBLICATIONS

Rajur, S. B. et al., "Covalent Protein-Oligonucleotide Conjugates for Efficient Delivery of Antisense Molecules," Bioconjugate Chem. (1997) 8(6):935-940.
Ranganathan, "Modification of the 21-Position of Purine Nucleosides: Synthesis of 21-a-Substituted-21-Deoxyadenosine Analogs", Tetrahedron Letters, 1977, 15, 1291-1294.
Ransford et al., "2'-O-Ethyl Pyrimidine Nucleosides," J. Carbohydrates—Nucleosides—Nucleotides, 1974, 1(3), 275-278.
Rao, et al., "A Novel One-step Procedure for the Conversion of Thymidine into 2,3'-Anhydrothymidine", J. Chem. Soc. Chem. Commun., 1989, 997-998.
Rausch, J.W. et al., "Hydrolysis of RNA/DNA hybrids containing nonpolar pyrimidine isosteres defines regions essential for HIV type 1 polypurine tract selection," PNAS (2003) 100(20): 11279-11284.
Reddy, M.P. et al., "Fast Cleavage and Deprotection of Oligonucleotides," Tetrahedron Letters, 1994, 35(25), 4311-4314.
Reese, C.B., et al., "4-(1,2,4-Triazol-1-yl)-and 4-(3-Nitro-1,2,4-triazol-1-yl)-1-(β-D-Arabinofuranosyl)cytosine(Ara-C)", J. Chem. Soc. Perkin Trans. I, 1982, pp. 1171-1176.
Renneberg, D. et al. "Antisense properties of tricyclo-DNA," Nucleic Acids Res., 2002, 30(13), 2751-2757.
Renneberg, D., et al., "Watson—Crick base-pairing properties of tricycle-DNA," J. Am. Chem. Soc., 2002, 124, 5993-6002.
Revankar et al., "Synthesis and Antiviral/Antitumor of Certain 3-Seazaguanine Nucleosides and Nucleotides", J. Med. Chem. 1984, 24, 1389-1396.
Rhodes, J. et al., "Therapeutic potentiation of the immune system by costimulatory Schiff-baseforming drugs," Nature (1995) 377(6544):71-75.
Robins, et al., "Nucleic Acid Related Compounds. 42. A General Procedure for the Efficient Deoxygenation of Secondary Alcohols. Regiospecific and Stereoselective Conversion of Ribonucleosides to 2'-Deoxynucleosides", J. Am. Chem. Soc., 1983, 105, 4059-4065.
Robins, et al., "Synthesis of 2'-Deoxytubercidin, 2'-Deoxyadenosine, and Related 2'-Deoxynucleosides via a Novel Direct Stereospecific Sodium Salt Glycosylation Procedure", J. Am. Chem. Soc., 1984, 106, 6379-6382.
Roelen et al., "Synthesis of Nucleic Acid Methylphos-Phonothioates", Nucleic Acids Research 1988, 16(15), 7633-7645.
Rottman et al., "Influence of 2'-O-Alkylation on the Structure of Single-Stranded Polynucleotides and the Stability of 2'-O-Alkylated Polynucleotide Complexes," Biochem., 1974, 13, 2762-2771.
Ruby, et al., "An Early Hierarchic Role of U1 Small Nuclear Ribonucleoprotein in Splicesome Assembly", Science, 1988, 242, 1028-1035.
Rump, E. T. et al., "Preparation of Conjugates of Oligodeoxynucleotides and Lipid Structures and Their interaction with Low-Density Lipoprotein," Bioconjugate Chem. (1998) 9(3):341-349.
Ryan, et al., "Synthesis of 2-Thio-D-ribose and 2'-Thioadenosine Derivatives", J. Org. Chem., 1971, 36(18), 2646-2657.
Sambrook, et al., "Molecular Cloning. A Laboratory Manual", Cold Spring Harbor Laboratory Press, 1989, vol. 2, pp. 11.31-11.32.
San et al., "Safety and short term toxicity of a novel cationic lipid formulation for human gene therapy", Human Gene Therapy, 1993, 4, 781-788.
Sanghvi, Y.S. et al., "Heterocyclic Base Modifications in Nucleic acids and their Applications in Antisense Oligonucleotides", Antisense Research and Applications, CRC Press, Boca Raton, Chapter 15, 1993, 273-288.
Scaringe, S.A. et al., "Novel RNA Synthesis Method Using 5'-O-Silyl-2'-O-orthoester Protecting Groups," J. Am. Chem. Soc., 1998, 120(45), 11820-11821.
Scaringe, S.A., "RNA Oligonucleotide Synthesis via 5'-Silyl-2'-Orthoester Chemistry," Methods, 2001, 23, 206-217.
Scaringe, S.A., Thesis entitled, "Design and Development of New Protecting Groups for RNA Synthesis," University of Colorado (1996).
Scherer et al., "Approaches for the sequence-specific knockdown of mRNA," Nat. Biotechnol., 2003, 21(12), 1457-1465.
Schöning, K.-U., et al., "Chemical etiology of nucleic acid structure: the α-threofuranosyl-(3'→2') oligonucleotide system," Science, 2000, 290, 1347-1351.
Schwartz, et al., "A microtransfection method using the luciferase-encoding reporter gene for the assay of human immunodeficiency virus LTR promoter activity", Gene, 1990, 88, 197-205.
Schwartz, M.E. et al., "Rapid Synthesis of Oligoribonucleotides Using 2'-O-(o-Nitrobenzyloxymethyl)-Protected Monomers," Bioorg. Med. Chem. Lett., 1992, 2(9), 1019-1024.
Schwarz, D.S. et al., "Asymmetry in the Assembly of the RNAi Enzyme Complex," Cell, 2003, 115(2), 199-208.
Searle, M. S. et al., "On the Stability of Nucleic Acid Structures in Solution: Enthalpy-Entropy Compensations, Internal Rotations and Reversibility," Nucl. Acids Res., 1993, 21(9), 2051-2056.
Seela, et al., "Palindromic Octa- and Dodecanucleotides Containing 2'-Deoxytubercidin: Synthesis, Hairpin Formation, and Recognition by the Endodeoxyribonuclease", Biochemistry, 1987, 26, 2232-2238.
Seliger, H., et al., "Synthetic Oligonucleotides for Biomedical Applications," Nucleic Acids Symp Ser., 1991, 24:193-196.
Shea et al., "Synthesis, hybridization properties and antiviral activity of lipid-oligodeoxynucletide conjugates", Nucl. Acids Res., 1990, 18(13), 3777-3783.
Sheehan, D. et al., "Biochemical properties of phosphonoacetate and thiophosphonoactate oligodeoxyribonucleotides," Nucleic Acids Res., 2003, 31(14), 4109-4118.
Shi, Y., "Mammalian RNAi for the masses," Trends in Genetics (2003) 19(1): 9-12.
Sigman, "Nuclease Activity of 1,10-Phenanthroline-Copper Ion", Acc. Chem. Res., 1986, 19, 180-186.
Singer et al., "Alkylation of Ribose in RNA Reacted with Ethylnitrosourea at Neutrality," Biochem., 1976, 15(23), 5052.
Singh, S.K. et al., "LNA (locked nucleic acids): synthesis and high-affinity nucleic acid recognition," Chem. Commun., 1998, 4, 455-456.
Singh, S.K., et al., "Synthesis of 2'-amino-LNA: a novel conformationally restricted high-affinity oligonucleotide analogue with a handle," J. Org. Chem., 1998, 63, 10035-10039.
Skorski, T. et al., "Antileukemia effect of c-myc N3'P5' phosphoramidate antisense oligonucleotides in vivo," Proc. Natl. Acad. Sci. USA, 1997, 94, 3966-3971.
Smith et al., "Antiviral effect of an oligo(nucleoside methylphosphonate) complementary to the splice junction of herpes simplex virus type 1 immediate early pre-mRNAs 4 and 5", Proc. Natl. Acad. Sci. USA, 1986, 83, 2787-2791.
Smith, T.F. et al., "Comparison of Biosequences," Adv. Appl. Math., 1981, 2, 482-489.
Song, E. et al., "RNA interference targeting Fas protects mice from fulmiant hepatitis," Nature Med., 2003, 9(3), 347-351.
Song, J.-J. et al., "The Crystal Structure of Argonaute and Its Implication for RISC Slicer Activity," Science, 2004, 305, 1434-1437.
Song, J.-J. et al., "The crystal structure of the Argonaute2 PAZ domain reveals an RNA binding motif in RNAi effector complexes," Nature Struct. Biol., 2003, 10(12), 1026-1032.
Soutschek, J. et al., "Therapeutic silencing of a endogenous gene by systemic administration of modified siRNAs," Nature, 2004, 432(7014), 173-178.
Sproat, et al., "Highly Efficient Chemical Synthesis of 2'-O-methylioligoribunocleotides and Tetrabiotinylated Derivatives; Novel Probes That are Resistant to Degradation by RNA or DNA Specific Nucleases", Nucleic Acids Research, 1989, 17, 3373-3386.
Sproat, et al., "New synthetic routes to protected purine 2'-O-methylriboside-3'-O-phosphoramidites using a novel alkylation procedure", Nucleic Acids Research, 1990, 18, 41-49.
Steffens, R., et al., "168. Nucleic-acid analogs with constraint conformational flexibility in the sugar-phosphate backbone tricycle-DNA," Helv. Chim. Acta, 1997, 80, 2426-2439.
Stein, et al., "Oligodeoxynucleotides as Inhibitors of Gene Expression: A Review", Cancer Research, 1988, 48, 2659-2668.

(56) References Cited

OTHER PUBLICATIONS

Stein, et al., "Physicochemical properties of phosphorothioate oligodeoxynucleotides", Nucleic Acids Research, 1988, 16, 3209-3221.
Struck, "Vaccine R&D Success Rates and Development Times," Nature Biotechnology, May 1996, 14, 591-593.
Stufkens, et al., "Dynamic Jahn-Teller Effect in the Excited States of SeCl62-, SeBr62-, TeCl62- and TeBr62-", Recueil des Travaux Chimiques des Pays-Bas 1970, 89, 1185-1201.
Suciu et al., "Synthesis of 9-(2,5-dideoxy-β-D-glycero-pent-4-enofuranosyl)adenine", Carbohydrate Research, 1975, 44, 112-115.
Sutcliffe, J.G. et al., "TOGA: An automated parsing technology for analyzing expression of nearly all genes," PNAS, 2000, 97(5), 1976-1981.
Svinarchuk, F.P. et al., "Inhibition of HIV proliferation in MT-4 cells by antisense oligonucleotide conjugated to lipophilic groups," Biochimie, 1993, 75, 49-54.
Tamanini, F. et al., "The fragile X-related proteins FXRlP and FXRZP contain a functional nucleolar-targeting signal equivalent to the HIV-1 regulatory proteins," Hum. Mol. Genet. (2000) 9(10):1487-1493.
Tang, X.-Q. et al., "2'-C-Branched Ribonucleosides: Synthesis of the Phosphoramidite Derivatives of 2'-C-Beta-Methylcytidine and Their Incorporation into Oligonucleotides," J. Org. Chem., 1999, 64(3), 747-754.
Tazawa et al., "A Novel Procedure for the Synthesis of 2'-O-Alkyl Nucleotides" Biochem., 1972, 11(26), 4931.
Thompson, "Applications of Antisense and siRNAs During Preclinical Drug Development," DDT (2002) 7(17): 912-917.
Tidd, D.M. et al., "Evaluation of N-ras oncogene anti-sense, sense and nonsense sequence methylphosphonate oligonucleotide analogues," Anti-Cancer Drug Design, 1988, 3(2), 117-127.
To, K.-Y. "Identification of differential gene expression by high throughput analysis," Comb. Chem. & High Throughput Screen, 2000, 3, 235-241.
U.S. Appl. No. 09/315,298, filed May 20, 1999, by Teng et al.
U.S. Appl. No. 60/423,760, filed Nov. 5, 2002, by Baker et al.
Van der Krol, et al., "Modulation of Eukaryotic Gene Expression by Complementary RNA or DNA Sequences", BioTechniques, 1988, 6, 958-976.
Vickers, T.A. et al., "Efficient Reduction of Target RNAs by Small Interfering RNA and Rnase H-dependent Antisense Agents," J. Biol. Chem., 2003, 278(9), 7108-7118.
Wada, A. et al., "Nuclear export of actin: a novel mechanism regulating the subcellular localization of a major cytoskeletal protein," EMBO J. (1998) 17:1635-1641.
Wahlestedt, C., et al., "Potent and nontoxic antisense oligonucleotides containing locked nucleic acids," Proc. Natl. Acad. Sci. U.S.A., 2000, 97(10), 5633-5638.
Walder, et al., "Antisense DNA and RNA: Progress and Prospects", Genes & Development, 1988, 2, 502-504.
Walder, et al., "Role of RNase H in Hybrid-Arrested Translation by Antisense Oligonucleotides", Proc. Natl. Acad. Sci. USA 1988, 85, 5011-5015.
Wang, J., et al., "Syhthesis and binding property of an oligonucleotide containing tetrafluorophenoxazine," Tetrahedron Lett., 1998, 39, 8385-8388.
Wang, X. et al., "Modular Recognition of RNA by a Human Pumilio-Homology Domain," Cell (2002) 110:501-512.
Wei, Z. et al., "Hybridization properties of oligodeoxynucleotide pairs bridged by polyarginine peptides," Nucleic Acids Res. (1996) 24(4):655-661.
Wein, G. et al., "The 3'-UTR of the mRNA coding for the major protein kinase C substrate MARCKS contains a novel CU-rich element interacting with MRNA stabilizing factors HuD and HuR," Eur. 1. Biochem. (2003) 270:350-365.
Wengel, J., et al., "LNA (locked nucleic acid)," Nucleosides, Nucleotides, 1999, 18(6 & 7), 1365-1370.

Wianny et al., "Specific interference with gene function by double-stranded RNA in early mouse development," Nature Cell Biology (2000) 2: 70-75.
Wilds, C.J., et al., "Duplex recognition by oligonucleotides containing 2'-deoxy-2'-fluoro-D-arabinose and 2'-deoxy-2'-fluoro-D-ribose. Intermolecular 2'-OH-phosphate contacts versus sugar puckering in the stabilization of triple-helical complexes," Bioconjugate Chem., 1999, 10, 299-305.
Williams, D.M., et al., "Properties of 2'-Fluorothymidine-Containing Oligonucleotides: Interaction with Restriction Endonuclease EcoRV," Biochemistry, 1991, 30, 4001-4009.
Wolfe, S., et al., "The guache effect. Some stereochemical consequences of adjacent electron pairs and polar bonds," Acc. of Chem. Res., 1972, 5, 102-111.
Wouters, J. et al., "5-Substituted Pyrimidine 1,5-Anhydronhexitols: Conformational Analysis and Interaction with Viral Thymidine Kinase," Bioorg. Med. Chem. Lett., 1999, 9, 1563-1566.
Wright, P. et al., "Large Scale Synthesis of Oligonucleotides via Phosphoramidite Nucleosides and a High-loaded Polystyrene Support," Tetrahedron Lett., 1993, 34(21), 3373-3376.
Wu, H. et al., "Properties of Cloned and Expressed Human RNase H1," Journal of Biological Chemistry 1999, vol. 274, pp. 28270-28278.
Wu, X., et al., "Base-pairing systems related to TNA: α-threofuranosyl oligonucleotides containing phosphoramidate linkages," Organic Lett., 2002, 4(8), 1279-1282.
Yang, Y. et al., "HIV-1 TAT-mediated protein transduction and subcellular localization using novel expression vectors," FEBS Letters (2002) 532, 36-44.
Yeung, et al., "Photoreactives and Thermal Properties of Psoralen Cross-Links", Biochemistry 1988, 27, 3204-3210.
Zamecnik, P.C. et al., "Inhibition of Rous sarcoma virus replication and cell transformation by a specific oligodeoxynucleotide," Proc. Natl. Acad. Sci. USA, 1978, 75(1), 280-284.
Zamore, P.D. et al., "Ancient Pathways Programmed by Small RNAs," Science, 2002, 296, 1265-1269.
Zamore, P.D. et al., "RNAi: Double-Stranded RNA Directs the ATP-Dependent Cleavage of mRNA at 21 to 23 Nucleotide Intervals," Cell, 2000, 101, 25-33.
Zanta, M. A. et al., "Gene delivery: A single nuclear localization signal peptide is sufficient to carry DNA to the cell nucleus," Proc. Natl. Acad. Sci. USA (1999) 96:91-96.
Zhang et al., "Single Processing Center Models for Human Dicer and Bacterial RNase IIi," Cell, 2004, 118, 57-68.
Zhang et al., "Targeted Gene Silencing by Small Interfering RNA-Based Knock-Down Technology," Current Pharmaceutical Biotechnology, 2004, 5, 1-7.
Zhang, H. et al., "Reduction of liver Fas expression by an antisense oligonucleotide protects mice from fuminant hepatitis," Nature Biotech., 2000, 18, 862-867.
Zhang, J., et al., "PowerBLAST: A new network BLAST application for interactive or automated sequence analysis and annotation," Genome Res., 1997, 7, 649-656.
Zhang, Z. et al., "Uptake of N-(4'-pyridoxyl)amines and release of amines by renal cells: A model for transporter-enhanced delivery of bioactive compounds," Proc. Natl. Acad. Sci. USA (1991) 88:10407-10410.
Zhao, Q. et al., "Effect of Different Chemically Modified Oligodeoxynucleotides on Immune Stimulation," Biochemical Pharmacology, 1996, 51, 173-182.
Zhu, T. et al., "Oligonucleotide-Poly-L-omithine Conjugates: Binding to Complementary DNA and RNA." Antisense Res. Dm. 119931 3:265-275.
Zon, "Oligonucleotide Analogues as Potential Chemotherapy Agents," Pharm. Res., 1988, 5(9), 539-549.
Zon, "Synthesis of Backbone-Modified DNA Analogues for Biological Applications", J. Protein Chemistry, 1987, 6, 131-145.
Zuckermann, R. N. et al., "Site-Selective Cleavage of RNA by a Hybrid Enzyme," J. Am. Chem. SOC. (1988) 110:1614-1615.

* cited by examiner

SEQUENCE LISTING

<160> NUMBER OF SEQ ID NOS: 77

<210> SEQ ID NO 1
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1
cgagaggcgg acgggaccg               19

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
cgagaggcgg acgggaccgt t             21

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
cggtcccgtc cgcctctcgt t             21

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-O-methoxyethyl
<220> FEATURE:
<221> NAME/KEY: misc_feature
<222> LOCATION: (13)..(20)
<223> OTHER INFORMATION: 2'-O-methoxyethyl

<400> SEQUENCE: 4
tccgtcatcg ctcctcaggg              20

<210> SEQ ID NO 5
<211> LENGTH: 20
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-O-methoxyethyl
<220> FEATURE:
<221> NAME/KEY: misc_feature
<222> LOCATION: (16)..(20)
<223> OTHER INFORMATION: 2'-O-methoxyethyl

<400> SEQUENCE: 5
gtgcgcgcga gcccgaaatc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-O-methoxyethyl
<220> FEATURE:
<221> NAME/KEY: misc_feature
<222> LOCATION: (16)..(20)
<223> OTHER INFORMATION: 2'-O-methoxyethyl

<400> SEQUENCE: 6
atgcattctg cccccaagga                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
caaauccaga ggcuagcagt t                                             21

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-O-methyl

<400> SEQUENCE: 8
cugcuagccu cuggauuugt t                                             21

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(6)
<223> OTHER INFORMATION: 2'-O-methyl

<400> SEQUENCE: 9
cugcuagccu cuggauuugt t                                             21
```

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(7)
<223> OTHER INFORMATION: 2'-O-methyl

<400> SEQUENCE: 10
cugcuagccu cuggauuugt t                                      21

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(8)
<223> OTHER INFORMATION: 2'-O-methyl

<400> SEQUENCE: 11
cugcuagccu cuggauuugt t                                      21

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(9)
<223> OTHER INFORMATION: 2'-O-methyl

<400> SEQUENCE: 12
cugcuagccu cuggauuugt t                                      21

<210> SEQ ID NO 13
<211> LENGTH: 21
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(21)
<223> OTHER INFORMATION: 2'-O-methyl modified nucleoside

<400> SEQUENCE: 13
cugcuagccu cuggauuugu u                                      21

<210> SEQ ID NO 14
<211> LENGTH: 21
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(21)
<223> OTHER INFORMATION: 2'-O-methyl modified nucleoside

<400> SEQUENCE: 14

-continued cugcuagccu cuggauuugu u                                              21

<210> SEQ ID NO 15
<211> LENGTH: 20
<212> TYPE: RNA
<213> ORGANISM: Artificial Sequence
<220> FEATURE:
<223> OTHER INFORMATION: Synthetic Construct

<400> SEQUENCE: 15
aaguaaggac cagagacaaa                                                20

<210> SEQ ID NO 16
<211> LENGTH: 20
<212> TYPE: RNA
<213> ORGANISM: Artificial Sequence
<220> FEATURE:
<223> OTHER INFORMATION: Synthetic Construct

<400> SEQUENCE: 16
uuugucucug guccuuacuu                                                20

<210> SEQ ID NO 17
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(20)
<223> OTHER INFORMATION: 2'-O-methyl modified nucleoside

<400> SEQUENCE: 17
uuugucucug guccuuacuu                                                20

<210> SEQ ID NO 18
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(17)
<223> OTHER INFORMATION: 2'-O-methyl modified nucleoside

<400> SEQUENCE: 18
uuugucucug guccuuacuu                                                20

<210> SEQ ID NO 19
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(14)
<223> OTHER INFORMATION: 2'-O-methyl modified nucleoside

<400> SEQUENCE: 19
uuugucucug guccuuacuu                                                20

<210> SEQ ID NO 20
<211> LENGTH: 20
<212> TYPE: RNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (9)..(11)
<223> OTHER INFORMATION: 2'-O-methyl modified nucleoside

<400> SEQUENCE: 20
uuugucucug guccuuacuu                                                         20

<210> SEQ ID NO 21
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(8)
<223> OTHER INFORMATION: 2'-O-methyl modified nucleoside

<400> SEQUENCE: 21
uuugucucug guccuuacuu                                                         20

<210> SEQ ID NO 22
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: 2'-O-methyl modified nucleoside

<400> SEQUENCE: 22
uuugucucug guccuuacuu                                                         20

<210> SEQ ID NO 23
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-O-methyl modified nucleoside

<400> SEQUENCE: 23
uuugucucug guccuuacuu                                                         20

<210> SEQ ID NO 24
<211> LENGTH: 21
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-O-methyl modified nucleoside

<400> SEQUENCE: 24
cugcuagccu cuggauuugu u                                                       21

<210> SEQ ID NO 25
<211> LENGTH: 21
<212> TYPE: RNA
```

```
<213> ORGANISM: Artificial Sequence
<220> FEATURE:
<223> OTHER INFORMATION: Synthetic Construct

<400> SEQUENCE: 25
gucaaaucca gaggcuagca g                                              21

<210> SEQ ID NO 26
<211> LENGTH: 21
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-O-methyl modified nucleoside

<400> SEQUENCE: 26
cugcuagccu cuggauuuga c                                              21

<210> SEQ ID NO 27
<211> LENGTH: 21
<212> TYPE: RNA
<213> ORGANISM: Artificial Sequence
<220> FEATURE:
<223> OTHER INFORMATION: Synthetic Construct

<400> SEQUENCE: 27
cugcuagccu cuggauuuga c                                              21

<210> SEQ ID NO 28
<211> LENGTH: 21
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(21)
<223> OTHER INFORMATION: 2'-O-methyl modified nucleoside

<400> SEQUENCE: 28
caaauccaga ggcuagcagu u                                              21

<210> SEQ ID NO 29
<211> LENGTH: 21
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(21)
<223> OTHER INFORMATION: 2'-O-methyl modified nucleoside

<400> SEQUENCE: 29
cugcuagccu cuggauuugu u                                              21

<210> SEQ ID NO 30
<211> LENGTH: 21
<212> TYPE: RNA
<213> ORGANISM: Artificial Sequence
<220> FEATURE:
<223> OTHER INFORMATION: Synthetic Construct

<400> SEQUENCE: 30
cugcuagccu cuggauuugu u                                              21
```

```
<210> SEQ ID NO 31
<211> LENGTH: 21
<212> TYPE: RNA
<213> ORGANISM: Artificial Sequence
<220> FEATURE:
<223> OTHER INFORMATION: Synthetic Construct

<400> SEQUENCE: 31
caaauccaga ggcuagcagu u                                              21

<210> SEQ ID NO 32
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(20)
<223> OTHER INFORMATION: 2'-O-methyl modified nucleoside

<400> SEQUENCE: 32
uuugucucug guccuuacuu                                                20

<210> SEQ ID NO 33
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(20)
<223> OTHER INFORMATION: 2'-O-methyl modified nucleoside

<400> SEQUENCE: 33
uuugucucug guccuuacuu                                                20

<210> SEQ ID NO 34
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(20)
<223> OTHER INFORMATION: 2'-O-methyl modified nucleoside

<400> SEQUENCE: 34
uuugucucug guccuuacuu                                                20

<210> SEQ ID NO 35
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(7)
<223> OTHER INFORMATION: 2'-O-Me containing monomers with PO linkages
<220> FEATURE:
<221> NAME/KEY: misc_feature
<222> LOCATION: (17)..(20)
<223> OTHER INFORMATION: 2'-O-Me containing monomers with PO linkages

<400> SEQUENCE: 35
```
cugcuagccu cuggauuuga                                              20

<210> SEQ ID NO 36
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-Me containing monomers with PO linkages
<220> FEATURE:
<221> NAME/KEY: misc_feature
<222> LOCATION: (17)..(20)
<223> OTHER INFORMATION: 2'-O-Me containing monomers with PO linkages

<400> SEQUENCE: 36
cugcuagccu cuggauuuga                                              20

<210> SEQ ID NO 37
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: PS linkage
<220> FEATURE:
<221> NAME/KEY: misc_feature
<222> LOCATION: (4)..(7)
<223> OTHER INFORMATION: 2'-O-Me containing monomers with PS linkages
<220> FEATURE:
<221> NAME/KEY: misc_feature
<222> LOCATION: (17)..(17)
<223> OTHER INFORMATION: 2'-O-Me containing monomers with PO linkage
<220> FEATURE:
<221> NAME/KEY: misc_feature
<222> LOCATION: (18)..(20)
<223> OTHER INFORMATION: 2'-O-Me containing monomers with PS linkages

<400> SEQUENCE: 37
cugcuagccu cuggauuuga                                              20

<210> SEQ ID NO 38
<211> LENGTH: 17
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-O-Me containing monomers with PO linkage
<220> FEATURE:
<221> NAME/KEY: misc_feature
<222> LOCATION: (2)..(4)
<223> OTHER INFORMATION: 2'-O-Me containing monomers with PS linkages
<220> FEATURE:
<221> NAME/KEY: misc_feature
<222> LOCATION: (14)..(14)
<223> OTHER INFORMATION: 2'-O-Me containing monomers with PO linkage
<220> FEATURE:
<221> NAME/KEY: misc_feature
<222> LOCATION: (15)..(17)
<223> OTHER INFORMATION: 2'-O-Me containing monomers with PS linkages

<400> SEQUENCE: 38
cuagccucug gauuuga                                                 17

```
<210> SEQ ID NO 39
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(20)
<223> OTHER INFORMATION: PS linkages
<220> FEATURE:
<221> NAME/KEY: misc_feature
<222> LOCATION: (4)..(7)
<223> OTHER INFORMATION: 2'-O-Me containing monomers
<220> FEATURE:
<221> NAME/KEY: misc_feature
<222> LOCATION: (17)..(20)
<223> OTHER INFORMATION: 2'-O-Me containing monomers

<400> SEQUENCE: 39
cugcuagccu cuggauuuga                                              20

<210> SEQ ID NO 40
<211> LENGTH: 17
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-Me containing monomers
<220> FEATURE:
<221> NAME/KEY: misc_feature
<222> LOCATION: (2)..(17)
<223> OTHER INFORMATION: monomers with PS linkages
<220> FEATURE:
<221> NAME/KEY: misc_feature
<222> LOCATION: (14)..(17)
<223> OTHER INFORMATION: 2'-O-Me containing monomers

<400> SEQUENCE: 40
cuagccucug gauuuga                                                 17

<210> SEQ ID NO 41
<211> LENGTH: 17
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-Me containing monomers
<220> FEATURE:
<221> NAME/KEY: misc_feature
<222> LOCATION: (2)..(17)
<223> OTHER INFORMATION: monomers having PS linkages
<220> FEATURE:
<221> NAME/KEY: misc_feature
<222> LOCATION: (14)..(17)
<223> OTHER INFORMATION: 2'-O-Me containing monomers

<400> SEQUENCE: 41
gucucugguc cuuacuu                                                 17

<210> SEQ ID NO 42
<211> LENGTH: 17
<212> TYPE: RNA
<213> ORGANISM: Artificial Sequence
<220> FEATURE:
<223> OTHER INFORMATION: Synthetic Construct
<220> FEATURE:
```

<221> NAME/KEY: misc_feature
<222> LOCATION: (1)..(4)
<223> OTHER INFORMATION: 2'-O-Me containing monomers
<220> FEATURE:
<221> NAME/KEY: misc_feature
<222> LOCATION: (2)..(17)
<223> OTHER INFORMATION: monomers with PS linkages
<220> FEATURE:
<221> NAME/KEY: misc_feature
<222> LOCATION: (14)..(17)
<223> OTHER INFORMATION: 2'-O-Me containing monomers

<400> SEQUENCE: 42
uuuugucucu gguccuu                                                         17

<210> SEQ ID NO 43
<211> LENGTH: 17
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-Me containing monomers
<220> FEATURE:
<221> NAME/KEY: misc_feature
<222> LOCATION: (2)..(17)
<223> OTHER INFORMATION: monomers having PS linkages
<220> FEATURE:
<221> NAME/KEY: misc_feature
<222> LOCATION: (14)..(17)
<223> OTHER INFORMATION: 2'-O-Me containing monomers

<400> SEQUENCE: 43
cugguccuua cuucccc                                                         17

<210> SEQ ID NO 44
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-O-Me containing monomers
<220> FEATURE:
<221> NAME/KEY: misc_feature
<222> LOCATION: (2)..(20)
<223> OTHER INFORMATION: monomers having PS linkages
<220> FEATURE:
<221> NAME/KEY: misc_feature
<222> LOCATION: (18)..(20)
<223> OTHER INFORMATION: 2'-O-Me containing monomers

<400> SEQUENCE: 44
uuugucucug guccuuacuu                                                      20

<210> SEQ ID NO 45
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-O-Me containing monomers
<220> FEATURE:
<221> NAME/KEY: misc_feature
<222> LOCATION: (2)..(20)
<223> OTHER INFORMATION: monomers having PS linkages

```
<220> FEATURE:
<221> NAME/KEY: misc_feature
<222> LOCATION: (16)..(20)
<223> OTHER INFORMATION: 2'-O-Me containing monomers

<400> SEQUENCE: 45
ucucuggucc uuacuucccc                                               20

<210> SEQ ID NO 46
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(20)
<223> OTHER INFORMATION: monomers having PS linkages
<220> FEATURE:
<221> NAME/KEY: misc_feature
<222> LOCATION: (4)..(7)
<223> OTHER INFORMATION: 2'-O-Me containing monomers
<220> FEATURE:
<221> NAME/KEY: misc_feature
<222> LOCATION: (17)..(20)
<223> OTHER INFORMATION: 2'-O-Me containing monomers

<400> SEQUENCE: 46
uuugucucug guccuuacuu                                               20

<210> SEQ ID NO 47
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-F containing monomers with PO linkages
<220> FEATURE:
<221> NAME/KEY: misc_feature
<222> LOCATION: (1)..(1)
<223> OTHER INFORMATION: 5-methyl cytidine
<220> FEATURE:
<221> NAME/KEY: misc_feature
<222> LOCATION: (4)..(4)
<223> OTHER INFORMATION: 5-methyl cytidine
<220> FEATURE:
<221> NAME/KEY: misc_feature
<222> LOCATION: (7)..(8)
<223> OTHER INFORMATION: 5-methyl cytidine
<220> FEATURE:
<221> NAME/KEY: misc_feature
<222> LOCATION: (10)..(10)
<223> OTHER INFORMATION: 5-methyl cytidine

<400> SEQUENCE: 47
cugcuagccu cuggauuugt t                                             21

<210> SEQ ID NO 48
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(21)
<223> OTHER INFORMATION: 2'-F containing monomers with PO linkages
<220> FEATURE:
<221> NAME/KEY: misc_feature
<222> LOCATION: (5)..(5)
```

```
<223> OTHER INFORMATION: 5-methyl cytidine
<220> FEATURE:
<221> NAME/KEY: misc_feature
<222> LOCATION: (9)..(9)
<223> OTHER INFORMATION: 5-methyl cytidine
<220> FEATURE:
<221> NAME/KEY: misc_feature
<222> LOCATION: (15)..(16)
<223> OTHER INFORMATION: 5-methyl cytidine
<220> FEATURE:
<221> NAME/KEY: misc_feature
<222> LOCATION: (21)..(21)
<223> OTHER INFORMATION: 5-methyl cytidine

<400> SEQUENCE: 48
ttgacgaucg gagaccuaaa c                                             21

<210> SEQ ID NO 49
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-F containing monomers with PO linkages

<400> SEQUENCE: 49 uuugcucug guccuuacuu                                                20

<210> SEQ ID NO 50
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-F containing monomers with PO linkages

<400> SEQUENCE: 50
aaacagagac caggaaugaa                                               20

<210> SEQ ID NO 51
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-F containing monomers with PS linkages

<400> SEQUENCE: 51 uuugcucug guccuuacuu                                                20

<210> SEQ ID NO 52
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: monomers with PS linkages
<220> FEATURE:
<221> NAME/KEY: misc_feature
```

```
<222> LOCATION: (15)..(17)
<223> OTHER INFORMATION: 2'-F containing monomers with PS linkages
<220> FEATURE:
<221> NAME/KEY: misc_feature
<222> LOCATION: (18)..(20)
<223> OTHER INFORMATION: monomers with PS linkages

<400> SEQUENCE: 52
uuugucucug guccuuacuu                                               20

<210> SEQ ID NO 53
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(11)
<223> OTHER INFORMATION: monomers with PS linkages
<220> FEATURE:
<221> NAME/KEY: misc_feature
<222> LOCATION: (12)..(14)
<223> OTHER INFORMATION: 2'-F containing monomers with PS linkages
<220> FEATURE:
<221> NAME/KEY: misc_feature
<222> LOCATION: (15)..(20)
<223> OTHER INFORMATION: monomers with PS linkages

<400> SEQUENCE: 53
uuugucucug guccuuacuu                                               20

<210> SEQ ID NO 54
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: monomers with PS linkages
<220> FEATURE:
<221> NAME/KEY: misc_feature
<222> LOCATION: (6)..(8)
<223> OTHER INFORMATION: 2'-F containing monomers with PS linkages
<220> FEATURE:
<221> NAME/KEY: misc_feature
<222> LOCATION: (9)..(20)
<223> OTHER INFORMATION: monomers with PS linkages

<400> SEQUENCE: 54
uuugucucug guccuuacuu                                               20

<210> SEQ ID NO 55
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: monomers with PS linkages
<220> FEATURE:
<221> NAME/KEY: misc_feature
<222> LOCATION: (3)..(5)
<223> OTHER INFORMATION: 2'-F containing monomers with PS linkages
<220> FEATURE:
<221> NAME/KEY: misc_feature
<222> LOCATION: (6)..(20)
<223> OTHER INFORMATION: monomers with PS linkages
```

```
<400> SEQUENCE: 55
uuugucucug guccuuacuu                                                    20

<210> SEQ ID NO 56
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-F containing monomers with PS linkages
<220> FEATURE:
<221> NAME/KEY: misc_feature
<222> LOCATION: (4)..(20)
<223> OTHER INFORMATION: Monomers with PS linkages

<400> SEQUENCE: 56
uuugucucug guccuuacuu                                                    20

<210> SEQ ID NO 57
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: Monomers with PS linkages
<220> FEATURE:
<221> NAME/KEY: misc_feature
<222> LOCATION: (18)..(20)
<223> OTHER INFORMATION: 2'-F containing monomers with PS linkages

<400> SEQUENCE: 57
uuugucucug guccuuacuu                                                    20

<210> SEQ ID NO 58
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(8)
<223> OTHER INFORMATION: Monomers with PS linkages
<220> FEATURE:
<221> NAME/KEY: misc_feature
<222> LOCATION: (9)..(11)
<223> OTHER INFORMATION: 2'-F containing monomers with PS linkages
<220> FEATURE:
<221> NAME/KEY: misc_feature
<222> LOCATION: (12)..(20)
<223> OTHER INFORMATION: Monomers with PS linkages

<400> SEQUENCE: 58
uuugucucug guccuuacuu                                                    20

<210> SEQ ID NO 59
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(15)
<223> OTHER INFORMATION: Monomers with PS linkages
```

```
<220> FEATURE:
<221> NAME/KEY: misc_feature
<222> LOCATION: (16)..(20)
<223> OTHER INFORMATION: 2'-F containing monomers with PS linkages

<400> SEQUENCE: 59
uuugucucug guccuuacuu                                                    20

<210> SEQ ID NO 60
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Monomers with PS linkages
<220> FEATURE:
<221> NAME/KEY: misc_feature
<222> LOCATION: (3)..(5)
<223> OTHER INFORMATION: 2'-F containing monomers with PO linkages
<220> FEATURE:
<221> NAME/KEY: misc_feature
<222> LOCATION: (3)..(5)
<223> OTHER INFORMATION: 2'-F containing monomers with PS linkages
<220> FEATURE:
<221> NAME/KEY: misc_feature
<222> LOCATION: (6)..(20)
<223> OTHER INFORMATION: Monomers with PS linkages

<400> SEQUENCE: 60
uuugucucug guccuuacuu                                                    20

<210> SEQ ID NO 61
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Monomers with PS linkages
<220> FEATURE:
<221> NAME/KEY: misc_feature
<222> LOCATION: (3)..(5)
<223> OTHER INFORMATION: 2'-F containing monomers with PO linkages
<220> FEATURE:
<221> NAME/KEY: misc_feature
<222> LOCATION: (6)..(11)
<223> OTHER INFORMATION: Monomers with PS linkages
<220> FEATURE:
<221> NAME/KEY: misc_feature
<222> LOCATION: (12)..(14)
<223> OTHER INFORMATION: 2'-F containing monomers with PS linkages
<220> FEATURE:
<221> NAME/KEY: misc_feature
<222> LOCATION: (15)..(20)
<223> OTHER INFORMATION: Monomers with PS linkages

<400> SEQUENCE: 61
uuugucucug guccuuacuu                                                    20

<210> SEQ ID NO 62
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
```

```
<223> OTHER INFORMATION: 2'-F containing monomers with PS linkages
<220> FEATURE:
<221> NAME/KEY: misc_feature
<222> LOCATION: (4)..(20)
<223> OTHER INFORMATION: Monomers with PS linkages

<400> SEQUENCE: 62
uuugucucug guccuuacuu                                                      20

<210> SEQ ID NO 63
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-F containing monomers with PS linkages
<220> FEATURE:
<221> NAME/KEY: misc_feature
<222> LOCATION: (4)..(17)
<223> OTHER INFORMATION: Monomers with PS linkages
<220> FEATURE:
<221> NAME/KEY: misc_feature
<222> LOCATION: (18)..(19)
<223> OTHER INFORMATION: 2'-F containing monomers with PS linkages
<220> FEATURE:
<221> NAME/KEY: misc_feature
<222> LOCATION: (20)..(20)
<223> OTHER INFORMATION: Monomers with PS linkages

<400> SEQUENCE: 63
uuugucucug guccuuacuu                                                      20

<210> SEQ ID NO 64
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-F containing monomers
<220> FEATURE:
<221> NAME/KEY: misc_feature
<222> LOCATION: (18)..(19)
<223> OTHER INFORMATION: 2'-F containing monomers

<400> SEQUENCE: 64
uuugucucug guccuuacuu                                                      20

<210> SEQ ID NO 65
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-F containing monomers with PS linkages
<220> FEATURE:
<221> NAME/KEY: misc_feature
<222> LOCATION: (4)..(4)
<223> OTHER INFORMATION: Monomer with PS linkage
<220> FEATURE:
<221> NAME/KEY: misc_feature
<222> LOCATION: (5)..(7)
<223> OTHER INFORMATION: 2'-F containing monomers with PS linkages
<220> FEATURE:
<221> NAME/KEY: misc_feature
```

```
<222> LOCATION: (8)..(13)
<223> OTHER INFORMATION: Monomers with PS linkages
<220> FEATURE:
<221> NAME/KEY: misc_feature
<222> LOCATION: (14)..(16)
<223> OTHER INFORMATION: 2'-F containing monomers with PS linkages
<220> FEATURE:
<221> NAME/KEY: misc_feature
<222> LOCATION: (17)..(17)
<223> OTHER INFORMATION: Monomer with PS linkage
<220> FEATURE:
<221> NAME/KEY: misc_feature
<222> LOCATION: (18)..(19)
<223> OTHER INFORMATION: 2'-F containing monomers with PS linkages
<220> FEATURE:
<221> NAME/KEY: misc_feature
<222> LOCATION: (20)..(20)
<223> OTHER INFORMATION: Monomer with PS linkage

<400> SEQUENCE: 65
uuugucucug guccuuacuu                                                     20

<210> SEQ ID NO 66
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-F containing monomers with PO linkages
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(5)
<223> OTHER INFORMATION: 2'-F containing monomers with PO linkages
<220> FEATURE:
<221> NAME/KEY: misc_feature
<222> LOCATION: (6)..(7)
<223> OTHER INFORMATION: 2'-OMe
<220> FEATURE:
<221> NAME/KEY: misc_feature
<222> LOCATION: (8)..(12)
<223> OTHER INFORMATION: 2'-F containing monomers with PO linkages
<220> FEATURE:
<221> NAME/KEY: misc_feature
<222> LOCATION: (13)..(15)
<223> OTHER INFORMATION: 2'-OMe
<220> FEATURE:
<221> NAME/KEY: misc_feature
<222> LOCATION: (16)..(18)
<223> OTHER INFORMATION: 2'-F containing monomers with PO linkages
<220> FEATURE:
<221> NAME/KEY: misc_feature
<222> LOCATION: (19)..(20)
<223> OTHER INFORMATION: 2'-OMe

<400> SEQUENCE: 66
cugcuagccu cuggauuugu t                                                   21

<210> SEQ ID NO 67
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: PS linkages
<220> FEATURE:
```

```
<221> NAME/KEY: misc_feature
<222> LOCATION: (8)..(9)
<223> OTHER INFORMATION: 2'-F containing monomers
<220> FEATURE:
<221> NAME/KEY: misc_feature
<222> LOCATION: (12)..(13)
<223> OTHER INFORMATION: 2'-F containing monomers
<220> FEATURE:
<221> NAME/KEY: misc_feature
<222> LOCATION: (18)..(20)
<223> OTHER INFORMATION: 2'-OMe

<400> SEQUENCE: 67
uuugucucug guccuuacuu                                               20

<210> SEQ ID NO 68
<211> LENGTH: 20
<212> TYPE: RNA
<213> ORGANISM: Artificial Sequence
<220> FEATURE:
<223> OTHER INFORMATION: Synthetic Construct

<400> SEQUENCE: 68
uucauuccug gucucuguuu                                               20

<210> SEQ ID NO 69
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-methoxyethoxy

<400> SEQUENCE: 69
uucauuccug gucucuguuu                                               20

<210> SEQ ID NO 70
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(6)
<223> OTHER INFORMATION: 2'-methoxyethoxy

<400> SEQUENCE: 70
uucauuccug gucucuguuu                                               20

<210> SEQ ID NO 71
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(9)
<223> OTHER INFORMATION: 2'-methoxyethoxy

<400> SEQUENCE: 71
uucauuccug gucucuguuu                                               20

<210> SEQ ID NO 72
<211> LENGTH: 20
```

```
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(12)
<223> OTHER INFORMATION: 2'-methoxyethoxy

<400> SEQUENCE: 72
uucauuccug gucucuguuu                                                    20

<210> SEQ ID NO 73
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(15)
<223> OTHER INFORMATION: 2'-methoxyethoxy

<400> SEQUENCE: 73
uucauuccug gucucuguuu                                                    20

<210> SEQ ID NO 74
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(18)
<223> OTHER INFORMATION: 2'-methoxyethoxy

<400> SEQUENCE: 74
uucauuccug gucucuguuu                                                    20

<210> SEQ ID NO 75
<211> LENGTH: 20
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(20)
<223> OTHER INFORMATION: 2'-methoxyethoxy

<400> SEQUENCE: 75
uucauuccug gucucuguuu                                                    20

<210> SEQ ID NO 76
<211> LENGTH: 10
<212> TYPE: DNA
<213> ORGANISM: Artificial Sequence
<220> FEATURE:
<223> OTHER INFORMATION: Synthetic Construct

<400> SEQUENCE: 76
tgcatttcag                                                               10

<210> SEQ ID NO 77
<211> LENGTH: 17
<212> TYPE: DNA
<213> ORGANISM: Artificial Sequence
<220> FEATURE:
```

```
<223> OTHER INFORMATION: Synthetic Construct

<400> SEQUENCE: 77
ttctcgctgc atttcag                                                          17
```

CHIMERIC OLIGOMERIC COMPOUNDS AND THEIR USE IN GENE MODULATION

CROSS-REFERENCE TO RELATED APPLICATIONS

The present application is a continuation in part of U.S. Ser. No. 10/078,949 filed Feb. 20, 2002 now U.S Pat. No. 7,695,902 which is a continuation of 09/479,783 filed Jan. 7, 2000, now abandoned which is a divisional of U.S. Ser. No. 08/870,608 filed Jun. 6, 1997 which was issued as U.S. Pat. No. 6,107,094 on Aug. 22, 2002, which is a continuation-in-part of U.S. Ser. No. 08/659,440 filed Jun. 6, 1996 which was issued as U.S. Pat. No. 5,898,031 on Apr. 27, 1999, each of which is incorporated herein by reference in its entirety. The present application also claims benefit to U.S. Provisional Application Ser. No. 60/423,760 filed Nov. 5, 2002, and U.S. Provisional Application Ser. No. 60/503,271 filed Sep. 15, 2003, all of which are incorporated herein by reference in their entirety.

FIELD OF THE INVENTION

The present invention provides modified oligomers that modulate gene expression via a RNA interference pathway. The oligomers of the invention include one or more modifications thereon resulting in differences in various physical properties and attributes compared to wild type nucleic acids. The modified oligomers are used alone or in compositions to modulate the targeted nucleic acids. In preferred embodiments of the invention, the modified oligomers are chimeric in nature.

BACKGROUND OF THE INVENTION

In many species, introduction of double-stranded RNA (dsRNA) induces potent and specific gene silencing. This phenomenon occurs in both plants and animals and has roles in viral defense and transposon silencing mechanisms. This phenomenon was originally described more than a decade ago by researchers working with the petunia flower. While trying to deepen the purple color of these flowers, Jorgensen et al. introduced a pigment-producing gene under the control of a powerful promoter. Instead of the expected deep purple color, many of the flowers appeared variegated or even white. Jorgensen named the observed phenomenon "cosuppression", since the expression of both the introduced gene and the homologous endogenous gene was suppressed (Napoli et al., *Plant Cell,* 1990, 2, 279-289; Jorgensen et al., *Plant Mol. Biol.,* 1996, 31, 957-973).

Cosuppression has since been found to occur in many species of plants, fungi, and has been particularly well characterized in *Neurospora crassa*, where it is known as "quelling" (Cogoni and Macino, *Genes Dev.* 2000, 10, 638-643; Guru, *Nature,* 2000, 404, 804-808).

The first evidence that dsRNA could lead to gene silencing in animals came from work in the nematode, *Caenorhabditis elegans*. In 1995, researchers Guo and Kemphues were attempting to use antisense RNA to shut down expression of the par-1 gene in order to assess its function. As expected, injection of the antisense RNA disrupted expression of par-1, but quizzically, injection of the sense-strand control also disrupted expression (Guo and Kempheus, *Cell,* 1995, 81, 611-620). This result was a puzzle until Fire et al. injected dsRNA (a mixture of both sense and antisense strands) into *C. elegans*. This injection resulted in much more efficient silencing than injection of either the sense or the antisense strands alone. Injection of just a few molecules of dsRNA per cell was sufficient to completely silence the homologous gene's expression. Furthermore, injection of dsRNA into the gut of the worm caused gene silencing not only throughout the worm, but also in first generation offspring (Fire et al., *Nature,* 1998, 391, 806-811).

The potency of this phenomenon led Timmons and Fire to explore the limits of the dsRNA effects by feeding nematodes bacteria that had been engineered to express dsRNA homologous to the *C. elegans* unc-22 gene. Surprisingly, these worms developed an unc-22 null-like phenotype (Timmons and Fire, *Nature* 1998, 395, 854; Timmons et al., *Gene,* 2001, 263, 103-112). Further work showed that soaking worms in dsRNA was also able to induce silencing (Tabara et al., *Science,* 1998, 282, 430-431). PCT publication WO 01/48183 discloses methods of inhibiting expression of a target gene in a nematode worm involving feeding to the worm a food organism which is capable of producing a double-stranded RNA structure having a nucleotide sequence substantially identical to a portion of the target gene following ingestion of the food organism by the nematode, or by introducing a DNA capable of producing the double-stranded RNA structure (Bogaert et al., 2001).

The posttranscriptional gene silencing defined in *Caenorhabditis elegans* resulting from exposure to double-stranded RNA (dsRNA) has since been designated as RNA interference (RNAi). This term has come to generalize all forms of gene silencing involving dsRNA leading to the sequence-specific reduction of endogenous targeted mRNA levels; unlike co-suppression, in which transgenic DNA leads to silencing of both the transgene and the endogenous gene.

Introduction of exogenous double-stranded RNA (dsRNA) into *Caenorhabditis elegans* has been shown to specifically and potently disrupt the activity of genes containing homologous sequences. Montgomery et al. suggests that the primary interference affects of dsRNA are post-transcriptional. This conclusion being derived from examination of the primary DNA sequence after dsRNA-mediated interference and a finding of no evidence of alterations, followed by studies involving alteration of an upstream operon having no effect on the activity of its downstream gene. These results argue against an effect on initiation or elongation of transcription. Finally using in situ hybridization they observed that dsRNA-mediated interference produced a substantial, although not complete, reduction in accumulation of nascent transcripts in the nucleus, while cytoplasmic accumulation of transcripts was virtually eliminated. These results indicate that the endogenous mRNA is the primary target for interference and suggest a mechanism that degrades the targeted mRNA before translation can occur. It was also found that this mechanism is not dependent on the SMG system, an mRNA surveillance system in *C. elegans* responsible for targeting and destroying aberrant messages. The authors further suggest a model of how dsRNA might function as a catalytic mechanism to target homologous mRNAs for degradation. (Montgomery et al., *Proc. Natl. Acad. Sci. USA,* 1998, 95, 15502-15507).

Recently, the development of a cell-free system from syncytial blastoderm Drosophila embryos, which recapitulates many of the features of RNAi, has been reported. The interference observed in this reaction is sequence specific, is promoted by dsRNA but not single-stranded RNA, functions by specific mRNA degradation, and requires a minimum length of dsRNA. Furthermore, preincubation of dsRNA potentiates its activity demonstrating that RNAi can be mediated by sequence-specific processes in soluble reactions (Tuschl et al., *Genes Dev.,* 1999, 13, 3191-3197).

In subsequent experiments, Tuschl et al, using the Drosophila in vitro system, demonstrated that 21- and 22-nt RNA fragments are the sequence-specific mediators of RNAi. These fragments, which they termed short interfering RNAs (siRNAs), were shown to be generated by an RNase III-like processing reaction from long dsRNA. They also showed that chemically synthesized siRNA duplexes with overhanging 3' ends mediate efficient target RNA cleavage in the Drosophila lysate, and that the cleavage site is located near the center of the region spanned by the guiding siRNA. In addition, they suggest that the direction of dsRNA processing determines whether sense or antisense target RNA can be cleaved by the siRNA-protein complex (Elbashir et al., *Genes Dev.,* 2001, 15, 188-200). Further characterization of the suppression of expression of endogenous and heterologous genes caused by the 21-23 nucleotide siRNAs have been investigated in several mammalian cell lines, including human embryonic kidney (293) and HeLa cells (Elbashir et al., *Nature,* 2001, 411, 494-498).

The Drosophila embryo extract system has been exploited, using green fluorescent protein and luciferase tagged siRNAs, to demonstrate that siRNAs can serve as primers to transform the target mRNA into dsRNA. The nascent dsRNA is degraded to eliminate the incorporated target mRNA while generating new siRNAs in a cycle of dsRNA synthesis and degradation. Evidence is also presented that mRNA-dependent siRNA incorporation to form dsRNA is carried out by an RNA-dependent RNA polymerase activity (RdRP) (Lipardi et al., *Cell,* 2001, 107, 297-307).

The involvement of an RNA-directed RNA polymerase and siRNA primers as reported by Lipardi et al. (Lipardi et al., *Cell,* 2001, 107, 297-307) is one of the many intriguing features of gene silencing by RNA interference. This suggests an apparent catalytic nature to the phenomenon. New biochemical and genetic evidence reported by Nishikura et al. also shows that an RNA-directed RNA polymerase chain reaction, primed by siRNA, amplifies the interference caused by a small amount of "trigger" dsRNA (Nishikura, *Cell,* 2001, 107, 415-418).

Investigating the role of "trigger" RNA amplification during RNA interference (RNAi) in *Caenorhabditis elegans,* Sijen et al revealed a substantial fraction of siRNAs that cannot derive directly from input dsRNA. Instead, a population of siRNAs (termed secondary siRNAs) appeared to derive from the action of the previously reported cellular RNA-directed RNA polymerase (RdRP) on mRNAs that are being targeted by the RNAi mechanism. The distribution of secondary siRNAs exhibited a distinct polarity (5'-3'; on the antisense strand), suggesting a cyclic amplification process in which RdRP is primed by existing siRNAs. This amplification mechanism substantially augmented the potency of RNAi-based surveillance, while ensuring that the RNAi machinery will focus on expressed mRNAs (Sijen et al., *Cell,* 2001, 107, 465-476).

Most recently, Tijsterman et al. have shown that, in fact, single-stranded RNA oligomers of antisense polarity can be potent inducers of gene silencing. As is the case for co-suppression, they showed that antisense RNAs act independently of the RNAi genes rde-1 and rde-4 but require the mutator/RNAi gene mut-7 and a putative DEAD box RNA helicase, mut-14. According to the authors, their data favor the hypothesis that gene silencing is accomplished by RNA primer extension using the mRNA as template, leading to dsRNA that is subsequently degraded suggesting that single-stranded RNA oligomers are ultimately responsible for the RNAi phenomenon (Tijsterman et al., *Science,* 2002, 295, 694-697).

Several recent publications have described the structural requirements for the dsRNA trigger required for RNAi activity. Recent reports have indicated that ideal dsRNA sequences are 21 nt in length containing 2 nt 3'-end overhangs (Elbashir et al, EMBO (2001), 20, 6877-6887, Sabine Brantl, *Biochimica et Biophysica Acta,* 2002, 1575, 15-25.) In this system, substitution of the 4 nucleosides from the 3'-end with 2'-deoxynucleosides has been demonstrated to not affect activity. On the other hand, substitution with 2'-deoxynucleosides or 2'-OMe-nucleosides throughout the sequence (sense or antisense) was shown to be deleterious to RNAi activity.

Investigation of the structural requirements for RNA silencing in *C. elegans* has demonstrated modification of the internucleotide linkage (phosphorothioate) to not interfere with activity (Parrish et al., *Molecular Cell,* 2000, 6, 1077-1087.) It was also shown by Parrish et al., that chemical modification like 2'-amino or 5-iodouridine are well tolerated in the sense strand but not the antisense strand of the dsRNA suggesting differing roles for the 2 strands in RNAi. Base modification such as guanine to inosine (where one hydrogen bond is lost) has been demonstrated to decrease RNAi activity independently of the position of the modification (sense or antisense). Some "position independent" loss of activity has been observed following the introduction of mismatches in the dsRNA trigger. Some types of modifications, for example introduction of sterically demanding bases such as 5-iodoU, have been shown to be deleterious to RNAi activity when positioned in the antisense strand, whereas modifications positioned in the sense strand were shown to be less detrimental to RNAi activity. As was the case for the 21 nt dsRNA sequences, RNA-DNA heteroduplexes did not serve as triggers for RNAi. However, dsRNA containing 2'-F-2'-deoxynucleosides appeared to be efficient in triggering RNAi response independent of the position (sense or antisense) of the 2'-F-2'-deoxynucleosides.

In one study the reduction of gene expression was studied using electroporated dsRNA and a 25mer morpholino oligomer in post implantation mouse embryos (Mellitzer et al., *Mehanisms of Development,* 2002, 118, 57-63). The morpholino oligomer did show activity but was not as effective as the dsRNA.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

U.S. Pat. Nos. 5,898,031 and 6,107,094, each of which is commonly owned with this application and each of which is herein incorporated by reference, describe certain oligonucleotide having RNA like properties. When hybridized with RNA, these oligonucleotides serve as substrates for a dsRNase enzyme with resultant cleavage of the RNA by the enzyme.

In another recently published paper (Martinez et al., *Cell,* 2002, 110, 563-574) it was shown that single stranded as well as double stranded siRNA resides in the RNA-induced silencing complex (RISC) together with elF2C1 and elf2C2 (human GERp950) Argonaute proteins. The activity of 5'-phosphorylated single stranded siRNA was comparable to the double stranded siRNA in the system studied. In a related study, the inclusion of a 5'-phosphate moiety was shown to enhance activity of siRNA's in vivo in Drosophilia embryos (Boutla, et al., *Curr. Biol.,* 2001, 11, 1776-1780). In another study, it was reported that the 5'-phosphate was required for siRNA function in human HeLa cells (Schwarz et al., *Molecular Cell,* 2002, 10, 537-548).

In yet another recently published paper (Chiu et al., *Molecular Cell,* 2002, 10, 549-561) it was shown that the 5'-hydroxyl group of the siRNA is essential as it is phosphorylated for activity while the 3'-hydroxyl group is not essential and tolerates substitute groups such as biotin. It was further shown that bulge structures in one or both of the sense or antisense strands either abolished or severely lowered the activity relative to the unmodified siRNA duplex. Also shown was severe lowering of activity when psoralen was used to cross link an siRNA duplex.

Like the RNAse H pathway, the RNA interference pathway for modulation of gene expression is an effective means for modulating the levels of specific gene products and, thus, would be useful in a number of therapeutic, diagnostic, and research applications involving gene silencing. The present invention therefore provides oligomeric compounds useful for modulating gene expression pathways, including those relying on mechanisms of action such as RNA interference and dsRNA enzymes, as well as antisense and non-antisense mechanisms. One having skill in the art, once armed with this disclosure will be able, without undue experimentation, to identify preferred oligonucleotide compounds for these uses.

SUMMARY OF THE INVENTION

In certain aspects, the invention relates to compositions comprising a first oligomer and a second oligomer, each having linked nucleosidic bases. At least a portion of the first oligomer is capable of hybridizing with at least a portion of the second oligomer, at least a portion of the first oligomer is complementary to and capable of hybridizing to a selected target nucleic acid, and at least one of the oligomers is a chimeric oligomeric compound.

In some embodiments, the chimeric oligomeric compound is a gapmer, an inverted gapmer, a 3'-hemimer, a 5'-hemimer or a blockmer. In certain embodiments, the chimeric oligomeric compound comprises at least two of DNA, RNA, PNA segments, and mixtures thereof.

The chimeric oligomeric compound may be a gapmer. In certain compositions, the gapmer comprises two terminal RNA segments having nucleotides of a first type and an internal RNA segment having nucleotides of a second type and where said nucleotides of said first type are different from said nucleotides of said second type. In other compositions, the nucleotides of the first type independently include at least one sugar substituent which is halogen, amino, trifluoroalkyl, trifluoroalkoxy, azido, aminooxy, alkyl, alkenyl, alkynyl, O—, S—, or N(R*)-alkyl; O—, S—, or N(R*)-alkenyl; O—, S— or N(R*)-alkynyl; O—, S— or N-aryl, O—, S—, or N(R*)-aralkyl; where the alkyl, alkenyl, alkynyl, aryl and aralkyl may be substituted or unsubstituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl; and said substituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl comprising substitution with alkoxy, thioalkoxy, phthalimido, halogen, amino, keto, carboxyl, nitro, nitroso, cyano, trifluoromethyl, trifluoromethoxy, imidazole, azido, hydrazino, aminooxy, isocyanato, sulfoxide, sulfone, disulfide, silyl, heterocycle, carbocycle, an intercalator, a reporter group, a conjugate, a polyamine, a polyamide, a polyalkylene glycol, or a polyether of the formula (—O-alkyl)$_m$, where m is 1 to about 10; and R* is hydrogen, or a protecting group.

In certain embodiments, the chimeric oligomeric compound is an inverted gapmer. In some embodiments, the inverted gapmer comprises two terminal RNA segments having nucleotides of a second type and an internal RNA segment having nucleotides of a first type and where said nucleotides of said first type are different from said nucleotides of said second type. In other embodiments, each of the nucleotides of said first type independently have at least one sugar substituent that is halogen, amino, trifluoroalkyl, trifluoroalkoxy, azido, aminooxy, alkyl, alkenyl, alkynyl, O—, S—, or N(R*)-alkyl; O—, S—, or N(R*)-alkenyl; O—, S— or N(R*)-alkynyl; O—, S— or N-aryl, O—, S—, or N(R*)-aralkyl; where the alkyl, alkenyl, alkynyl, aryl and aralkyl may be substituted or unsubstituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl; and said substituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl comprising substitution with alkoxy, thioalkoxy, phthalimido, halogen, amino, keto, carboxyl, nitro, nitroso, cyano, trifluoromethyl, trifluoro-methoxy, imidazole, azido, hydrazino, aminooxy, isocyanato, sulfoxide, sulfone, disulfide, silyl, heterocycle, carbocycle, an intercalator, a reporter group, a conjugate, a polyamine, a polyamide, a polyalkylene glycol, or a polyether of the formula (—O-alkyl)$_m$, where m is 1 to about 10; and R* is hydrogen, or a protecting group.

In some compositions, the chimeric oligomeric compound is 3'-hemimer. In certain embodiments, the 3'-hemimer comprises a terminal RNA segment having nucleotides of a first type and a further RNA segment having nucleotides of a second type and where said nucleotides of said first type are different from said nucleotides of said second type. In certain compositions, each of the nucleotides of the first type independently includes at least one sugar substituent that is halogen, amino, trifluoroalkyl, trifluoroalkoxy, azido, aminooxy, alkyl, alkenyl, alkynyl, O—, S—, or N(R*)-alkyl; O—, S—, or N(R*)-alkenyl; O—, S— or N(R*)-alkynyl; O—, S— or N-aryl, O—, S—, or N(R*)-aralkyl; where the alkyl, alkenyl, alkynyl, aryl and aralkyl may be substituted or unsubstituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl; and said substituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl comprising substitution with alkoxy, thioalkoxy, phthalimido, halogen, amino, keto, carboxyl, nitro, nitroso, cyano, trifluoromethyl, trifluoromethoxy, imidazole, azido, hydrazino, aminooxy, isocyanato, sulfoxide, sulfone, disulfide, silyl, heterocycle, carbocycle, an intercalator, a reporter group, a conjugate, a polyamine, a polyamide, a polyalkylene glycol, or a polyether of the formula (—O-alkyl)$_m$, where m is 1 to about 10; and R* is hydrogen, or a protecting group.

In certain aspects, the invention concerns compositions where chimeric oligomeric compound is 5'-hemimer. In some compositions, the 5'-hemimer comprises a terminal RNA segment having nucleotides of a first type and a further RNA segment having nucleotides of a second type and where said nucleotides of said first type are different from said nucleotides of said second type. Some embodiments have each of the nucleotides of said first type independently includes at least one sugar substituent that is halogen, amino, trifluoroalkyl, trifluoroalkoxy, azido, aminooxy, alkyl, alkenyl, alkynyl, O—, S—, or N(R*)-alkyl; O—, S—, or N(R*)-alkenyl; O—, S— or N(R*)-alkynyl; O—, S— or N-aryl, O—, S—, or N(R*)-aralkyl; where the alkyl, alkenyl, alkynyl, aryl and aralkyl may be substituted or unsubstituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl; and said substituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl comprising substitution with alkoxy, thioalkoxy, phthalimido, halogen, amino, keto, carboxyl, nitro, nitroso, cyano, trifluoromethyl, trifluoromethoxy, imidazole, azido, hydrazino, aminooxy, isocyanato, sulfoxide, sulfone, disulfide, silyl, heterocycle, carbocycle, an intercalator, a reporter group, a conjugate, a polyamine, a polyamide, a polyalkylene glycol, or a polyether of the formula (—O-alkyl)$_m$, where m is 1 to about 10; and R* is hydrogen, or a protecting group.

In other embodiments, the chimeric oligomeric compound comprises a blockmer. In some embodiments, the blockmer is an oligonucleotide having a block of at least two consecutive nucleotides of a first type located immediately adjacent at least one nucleotide of a second type and where said nucleotides of said first type are different from said nucleotides of said second type. In other compositions, each of the nucleotides of said first type independently includes at least one sugar substituent that is halogen, amino, trifluoroalkyl, trifluoroalkoxy, azido, aminooxy, alkyl, alkenyl, alkynyl, O—, S—, or N(R*)-alkyl; O—, S—, or N(R*)-alkenyl; O—, S— or N(R*)-alkynyl; O—, S— or N-aryl, O—, S—, or N(R*)-aralkyl; where the alkyl, alkenyl, alkynyl, aryl and aralkyl may be substituted or unsubstituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl; and said substituted $C_1$ to $C_{10}$ alkyl, $C_2$ to $C_{10}$ alkenyl, $C_2$ to $C_{10}$ alkynyl, $C_5$-$C_{20}$ aryl or $C_6$-$C_{20}$ aralkyl comprising substitution with alkoxy, thioalkoxy, phthalimido, halogen, amino, keto, carboxyl, nitro, nitroso, cyano, trifluoromethyl, trifluoro-methoxy, imidazole, azido, hydrazino, aminooxy, isocyanato, sulfoxide, sulfone, disulfide, silyl, heterocycle, carbocycle, an intercalator, a reporter group, a conjugate, a polyamine, a polyamide, a polyalkylene glycol, or a polyether of the formula (—O-alkyl)$_m$, where m is 1 to about 10; and R* is hydrogen, or a protecting group. In some preferred embodiments, the nucleotides of said of said second type comprise 2'-OH nucleotides.

Some embodiments further comprise a plurality of blocks of at least two consecutive nucleotides of a first type and wherein each of said blocks of nucleotides of said first type is separated from others of said blocks of nucleotides of said first type by a nucleotide of said second type.

In other aspects of the invention, the chimeric oligomer compound comprises a gapmer of the formula PNA-RNA-PNA. In certain embodiments, the chimeric oligomeric compound comprises a 5'-hemimer the formula PNA-RNA or a 3'-hemimer of the formula RNA-PNA. In yet other embodiments, the chimeric oligomeric compound comprises an inverted gapmer of the formula RNA-PNA-RNA.

The compounds of the invention may be chimeric oligomeric compound that are divided into at least two regions: a first region comprising α-nucleosides linked by charged or neutral 3'-5' phosphorous linkages; α-nucleosides linked by charged or neutral 2'-5' phosphorous linkages; α-nucleosides linked by non-phosphorous linkages; 4'-thionucleosides linked by charged or neutral 3'-5' phosphorous linkages; 4'-thionucleosides linked by charged or neutral 2'-5' phosphorous linkages; 4'-thionucleosides linked by non-phosphorous linkages; carbocyclic-nucleosides linked by charged or neutral 3'-5' phosphorous linkages; carbocyclic-nucleosides linked by charged or neutral 2'-5' phosphorous linkages; carbocyclic-nucleosides linked by non-phosphorous linkages; β-nucleosides linked by charged or neutral 3'-5' linkages; β-nucleosides linked by charged or neutral 2'-5' linkages; or β-nucleosides linked by non-phosphorous linkages; and a second region consists of 2'-ribo-β-nucleosides linked by charged 3'-5' phosphorous linkages.

Some preferred embodiments, are divided into at least two regions: a first region comprising α-nucleosides linked by charged or neutral 3'-5' phosphorous linkages, α-nucleosides linked by charged or neutral 2'-5' phosphorous linkages, α-nucleosides linked by non-phosphorous linkages, 4'-thionucleosides linked by charged or neutral 3'-5' phosphorous linkages, 4' thionucleosides linked by charged or neutral 2'-5' phosphorous linkages, 4'-thionucleosides linked by non-phosphorous linkages, carbocyclic-nucleosides linked by charged or neutral phosphorous linkages, carbocyclic-nucleosides linked by non-phosphorous linkages, β-nucleosides linked by charged or neutral 3'-5' linkages, β-nucleosides linked by charged or neutral 2'-5' linkages, or β-nucleosides linked by non-phosphorous linkages; and a second region comprising nucleobases linked by non-phosphorous linkages or nucleobases that are attached to phosphate linkages via a non-sugar tethering moiety.

In other embodiments, the chimeric oligomeric compound is divided into at least two regions: a first region comprising nucleobases linked by non-phosphorous linkages and nucleobases that are attached to phosphate linkages via non-sugar tethering groups, and nucleosides selected from α-nucleosides linked by charged or neutral 3'-5' phosphorous linkages, α-nucleosides linked by charged or neutral 2'-5' phosphorous linkages, α-nucleosides linked by non-phosphorous linkages, 4'-thionucleosides linked by charged or neutral 3'-5' phosphorous linkages, 4'-thionucleosides linked by charged or neutral 2'-5' phosphorous linkages, 4'-thionucleosides linked by non-phosphorous linkages, carbocyclic-nucleosides linked by charged or neutral 3'-5' phosphorous linkages, carbocyclic-nucleosides linked by charged or neutral 2'-5' phosphorous linkages, carbocyclic-nucleosides linked by non-phosphorous linkages, β-nucleosides linked by charged or neutral 3'-5' linkages; β-nucleosides linked by charged or neutral 2'-5' linkages, or β-nucleosides linked by non-phosphorous linkages; and a second region comprising 2'-ribo-β-nucleosides linked by charged 3'-5' phosphorous linkages wherein the 3'-5' phosphorous linkages.

Certain embodiments comprise at least two segments, wherein at least one segment comprises non-naturally occurring internucleoside linkages.

Other embodiments comprise an oligomer mimetic.

In certain embodiments, the nucleotides of the first type comprise nucleotides having a 2' halogen sugar substituent. In some embodiments, the halogen is F. In other embodiments, the nucleotides of the first type comprise nucleotides having a 2' O-alkyl sugar substituent. In certain embodiments, the —O-alkyl is —O—$CH_3$. In still other embodiments, the nucleotides of said first type comprise nucleotides having a 2' sugar substituent and where said 2' sugar substituent is of the formula —X—Y, wherein:

X is O, S, NR**, or CR* wherein each R** is independently H or $C_{1-6}$ alkyl; and Y is substituted or unsubstituted $C_{1-20}$ alkyl, substituted or unsubstituted $C_{2-20}$ alkenyl, or substituted or unsubstituted $C_{6-20}$ aryl.

In certain other embodiments, the invention is directed to oligonucleomer/protein compositions comprising an oligomer complementary to and capable of hybridizing to a selected target nucleic acid, and at least one protein comprising at least a portion of a RNA-induced silencing complex (RISC). The oligomer is a chimeric oligomeric compound.

In other aspects, the invention relates to oligomers having at least a first region and a second region where the first region is complementary to and capable of hybridizing with the second region, and at least a portion of the oligomer is complementary to and is capable of hybridizing to a selected target nucleic acid. At least one of the regions is a chimeric oligomeric composition.

The first and second oligomers preferably each have 10 to 40 nucleosidic bases. In other embodiments, each of the first and second oligomers have 18 to 30 nucleosidic bases. In yet other embodiments, the first and second oligomers have 21 to 24 nucleosidic bases.

Also provided by the present invention are pharmaceutical compositions comprising any of the above compositions or oligomeric compounds and a pharmaceutically acceptable carrier.

Methods for modulating the expression of a target nucleic acid in a cell are also provided, wherein the methods comprise contacting the cell with any of the above compositions or oligomeric compounds.

The invention also concerns methods of treating or preventing a disease or condition associated with a target nucleic acid are also provided, wherein the methods comprise administering to a patient having or predisposed to the disease or condition a therapeutically effective amount of any of the above compositions or oligomeric compounds.

DETAILED DESCRIPTION OF THE INVENTION

The present invention provides oligomeric compounds useful in the modulation of gene expression. Although not intending to be bound by theory, oligomeric compounds of the invention are believed to modulate gene expression by hybridizing to a nucleic acid target resulting in loss of normal function of the target nucleic acid. As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In a preferred embodiment of this invention modulation of gene expression is effected via modulation of a RNA associated with the particular gene RNA.

The invention provides for modulation of a target nucleic acid that is a messenger RNA. The messenger RNA is degraded by the RNA interference mechanism as well as other mechanisms in which double stranded RNA/RNA structures are recognized and degraded, cleaved or otherwise rendered inoperable.

The functions of RNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

Compounds of the Invention

The present invention concerns certain modified oligomeric compounds that are not uniform in chemical composition. Discussed herein are numerous modifications that may be made to oligomeric compounds. In certain embodiments, more than one of these modifications may be incorporated in a single oligomeric compound or even at a single monomeric subunit such as a nucleoside within a oligomeric compound.

Modified oligomeric compounds of the present invention include chimeric oligomeric compounds. "Chimeric" oligomeric compounds, or "chimeras," in the context of this invention, are oligomeric compounds that contain two or more chemically distinct regions, each made up of at least one monomer unit, e.g., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described herein. Such oligomeric compounds have also been referred to in the art as hybrids, hemimers, gapmers or inverted gapmers. Representative United States patents that teach the preparation of such structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The terms blockmer, 3'-hemimer, 5'-hemimer, gapmer and inverted gapmer are used in this specification to identify certain motifs or positional placement of types or segments of nucleotides in an oligomer. Depending on the number of nucleotide or nucleoside subunits and their position in the oligomer, one or more than one of these terms might apply to a particular construction and could be used for identification purposes. A blockmer has at least one block or segment of at least two consecutively located nucleotide or nucleoside subunits of a first type positioned adjacent to at least one nucleotide or nucleoside of a second type. Thus for instances if the nucleotides or nucleosides of the first type are represented by "X" and those of the second type are represented by "Y" and if " . . . " represent nucleotides or nucleosides other that the X or Y type nucleotides or the absence of any nucleotides then the following structures . . . XXY . . . ; . . . XXYXX . . . ; . . . XXYXXY . . . ; . . . XXYXXYXX . . . on so on for higher homologs are possible where each X containing segment includes two members and each Y containing segment includes only one member. If each X containing segment includes two members and each Y subunit also includes two members other representational blockmers include . . . XXYY . . . ; . . . XXYYXX . . . ; . . . XXYYXXYY . . . ; . . . XXYYXXYYXX . . . and so on for high homologs. These can be extended to other representative structures having more X and/or Y members in the blocks or segments, as for instances the structures YXXXXYYYXXXY; YYXXX-YYXXXYY; and YYYYXXXXYYYYXXXX.

If a block or segment of the first type of nucleotides or nucleoside resides at the 5' or the 3' terminus and all of the remaining nucleotides or nucleosides of the oligomer are of the second type, then that blockmer is also a hemimer. Using the same X and Y representation and selecting five members for each segment and basing the hemimer designation on the X members then the representations XXXXXYYYYY and YYYYYXXXX represent, respectively, 5' and 3' hemimers.

In gapmers, a block or segment of one type of nucleotides or nucleosides is interspaced between first and second blocks of the second type. As before if the designation is based on the X members then XXXXYYYYYXXXX represents a gapmer and YYYYXXXXYYYY represents an inverterted gapmer.

The chimric oligomeric compounds may contain any modification known to those skilled in the art. Examples of suitable modifications include modification of the sugar moiety, replacement of the sugar with a sugar surrogate, and modification to the backbone.

In some embodiments, the chimeric compound comprises at least two segments that are DNA segments, RNA segments, oligomer mimetic segments, or mixtures thereof. In certain preferred embodiments, the oligomer mimetic is a peptide nucleic acid (PNA). In one preferred embodiment, a chimeric oligomeric compound according to the invention contains DNA and peptide nucleic acid (PNA) segments.

Oligonucleoside segments according to the invention are formed from units that have pentofuranosyl sugars and naturally-occurring or non-naturally occurring nucleobases. DNA segments are formed from nucleoside units that have 2'-deoxy-erythro-pentofuranosyl sugar moieties and such a nucleobase, while RNA segments are formed from nucleoside units that have 2'-hydroxy-erythro-pentofuranosyl sugar moieties and such a nucleobase. Modified oligonucleoside segments are formed from nucleoside units that have some other type of pentofuranosyl sugar. The nucleosides are linked together and/or to other moieties by linkages disclosed herein. Such linkages include phosphodiester linkages, phosphorothioate linkages and/or phosphorodithioate linkages. In certain preferred compounds of the invention each of the nucleosides of the 2'-deoxyoligonucleotide portion are linked together by phosphorothioate linkages. In other preferred embodiments, they are linked together by phosphodiester linkages and in even further preferred embodiments, a mixture of phosphodiester and phosphorothioate linkages.

The peptide nucleic acid segments of the compounds typically increase the binding affinity of the compound to a complementary strand of nucleic acid. They also typically provide for nuclease stability of the compound against degradation by cellular nucleases. Selecting the 2'-deoxyoligonucleotide portion of the compound to include one or more or all phosphorothioate or phosphorodithioate linkages provides further nuclease stability to the compounds of the invention.

The PNA portions of the compounds of the invention are made up of units comprising a N-(2-aminoethyl)glycine or analogues thereof having a nucleobase attached thereto via a linker such as a carboxymethyl moiety or analogues thereof to the nitrogen atom of the glycine portion of the unit. The units are coupled together via amide bonds formed between the carboxyl group of the glycine moiety and the amine group of the aminoethyl moiety. The nucleobase can be one of the four common nucleobases of nucleic acids or they can include other natural or synthetic nucleobases. PNA compositions are discussed in more detail below.

In one embodiment, the chimera is a PNA-RNA-PNA composition where each PNA and RNA segment comprises at least one PNA or RNA monomer (also referred to herein as a "subunit"). In another embodiment, the chimera is RNA-PNA-RNA. Some segments may contain at least two subunits. Other segments contain at least three subunits. Yet other segments may contain five or more subunits.

In some preferred compounds of the invention the PNA-DNA-PNA structure is formed by connecting together the respective N-(2-aminoethyl)glycine PNA units and the respective 2'-ribose sugar phosphate RNA units. Thus the nucleobases of the PNA portion of the compounds of the invention are carried on a backbone composed of N-(2-aminoethyl)glycine PNA units and the nucleobases of the RNA portion of the compounds of the invention are carried on a backbone composed of 2'-ribose sugar phosphate units. Together, the nucleobases of the PNA portions and the nucleobases of the RNA portion of the compounds of the invention are connected by their respective backbone units in a sequence that is hybridizable to a complementary nucleic acid, as for instance, a targeted RNA stand.

In some preferred compounds of the invention the PNA and the RNA portions are joined together with amide linkages. Such preferred compound of the invention are of the structure:

PNA-(amide link)-RNA-(amide link)-PNA.

The amide linkage may be oriented as —C(O)NH— or —NHC(O)—. Other linkages that can be used to join the PNA and the RNA portions include those internucleoside linkages disclosed below. In some preferred embodiment, the linkages are amine ester linkages.

In another embodiment, the chimera is a PNA-RNA or RNA-PNA composition wherein the PNA and DNA segments are as described above.

Mixed PNA and DNA compositions are discussed in detail in U.S. Pat. No. 5,700,922, the disclosure of which is incorporated in its entirety by reference herein. Mixed RNA and PNA compositions may be made by analogous methods.

In some embodiments the chimeric oligomeric composition may be a modified RNA. In some embodiments, these chimeric oligomers may be gapmers, an inverted gapmer, or a hemimers. In certain embodiments, the modified segment of RNA comprises a 2'-substituted-oligoribonucleotide. For purposes of the invention, the term "2'-substituted" means replacement of the 2'-OH of the ribose molecule with a sugar substituent other than H. The sugar substituent may be any one of the sugar substituents disclosed herein. In some embodiments, the sugar substituent is —O-alkyl containing 1-6 carbon atoms, aryl or substituted aryl or $C_{2-6}$ allyl. Examples of these substituents are 2'-OMe, 2'-O-allyl, 2'-O-aryl, 2'-O-alkyl, 2'-halo, and 2'-amino. In some preferred embodiments, the sugar substituent is —O-alkyl. In other embodiments, the sugar substituent is F. In certain embodiments, allyl, aryl, or alkyl groups may be optionally substituted with substituents that include one or more halo, hydroxy, trifluoromethyl, cyano, nitro, acyl, acyloxy, alkoxy, carboxyl, carbalkoxyl and amino groups. Modified sugar compositions are discussed in more detail in U.S. Pat. Nos. 5,652,355 and 5,652,356, the disclosures of which are incorporated herein by reference in their entirety.

In yet other embodiments, the chimeric oligomeric compositions comprise modified internucleoside linkages and the use of α-nucleosides and β-nucleosides. Such modifications may produce segments that increase binding affinity of the oligonucleotide to a complementary strand of nucleic acid. See U.S. Pat. No. 5,623,065, the disclosure of which is incorporated herein by reference in its entirety.

In certain preferred embodiments, the nucleotide units that bear such substituents can be divided into a first nucleotide unit sub-sequence and a second nucleotide unit sub-sequence, with 2'-deoxy-erythro-pentofuranosyl structures being positioned within the oligonucleotide between the first nucleotide unit sub-sequence and the second nucleotide unit sub-sequence. In certain embodiments, it is preferred that all such intervening nucleotide units be 2'-deoxy-erythro-pentofuranosyl units.

In further preferred oligomers of the invention, nucleotide units bearing substituents that increase binding affinity are located at one or both of the 3' or the 5' termini of the oligomer. There can be from one to about eight nucleotide units that are substituted with substituent groups. Preferably, at least five sequential nucleotide units are 2'-deoxy-erythro-pentofuranosyl sugar moieties.

The present invention also provides compounds formed from a plurality of linked nucleosides selected from α-nucleosides, β-nucleosides including 2'-deoxy-erythro-pentofuranosyl β-nucleosides, 4'-thionucleosides, and carbocyclic-nucleosides. These nucleosides are connected by linkages in a sequence that is hybridizable to a complementary nucleic acid. The linkages are selected from charged phosphorous linkages, neutral phosphorous linkages, and non-phosphorous linkages. The sequence of linked nucleosides is divided into at least two regions. The first nucleoside region includes the following types of nucleosides: α-nucleosides linked by charged or neutral 3'-5' phosphorous linkages; α-nucleosides linked by charged or neutral 2'-5' phosphorous linkages; α-nucleosides linked by non-phosphorous linkages; 4'-thionucleosides linked by charged or neutral 3'-5' phosphorous linkages; 4'-thionucleosides linked by charged or neutral 2'-5' phosphorous linkages; 4'-thionucleosides linked by non-phosphorous linkages; carbocyclic-nucleosides linked by charged or neutral 3'-5' phosphorous linkages; carbocyclic-nucleosides linked by charged or neutral 2'-5' phosphorous linkages; carbocyclic-nucleosides linked by non-phosphorous linkages; β-nucleosides linked by charged or neutral 3'-5' linkages; β-nucleosides linked by charged or neutral 2'-5' linkages; and β-nucleosides linked by non-phosphorous linkages. A second nucleoside region consists of 2'-ribo-β-nucleosides linked by charged 3'-5' phosphorous linkages. In some embodiments, the 3'-5' phosphorous linkages have a negative charge at physiological pH. In preferred embodiments, the compounds include at least 3 of said 2'-deoxy-erythro-pentofuranosyl β-nucleosides, more preferably at least 5 of said 2'-deoxy-erythro-pentofuranosyl β-nucleotides. In further preferred embodiments there exists a third nucleoside region whose nucleosides are selected from those selectable for the first region. In preferred embodiments the second region is positioned between the first and third regions.

Certain preferred charged phosphorous linkages include phosphodiester, phosphorothioate, phosphorodithioate, phosphoroselenate and phosphorodiselenate linkages; phosphodiester and phosphorothioate linkages are particularly preferred. Preferred neutral phosphorous linkages include alkyl and aryl phosphonates, alkyl and aryl phosphoroamidites, alkyl and aryl phosphotriesters, hydrogen phosphonate and boranophosphate linkages. Preferred non-phosphorous linkages include peptide linkages, hydrazine linkages, hydroxy-amine linkages, carbamate linkages, morpholine linkages, carbonate linkages, amide linkages, oxymethyleneimine linkages, hydrazide linkages, silyl linkages, sulfide linkages, disulfide linkages, sulfone linkages, sulfoxide linkages, sulfonate linkages, sulfonamide linkages, formacetal linkages, thioformacetal linkages, oxime linkages and ethylene glycol linkages.

The invention also provides compounds formed from a plurality of linked units, each of which is selected from nucleosides and nucleobases. The nucleosides include α-nucleosides, β-nucleosides including 2'-deoxy-erythro-pentofuranosyl β-nucleosides, 4'-thionucleosides and carbocyclic-nucleosides. The nucleobases include purin-9-yl and pyrimidin-1-yl heterocyclic bases. The nucleosides and nucleobases of the units are linked together by linkages in a sequence wherein the sequence is hybridizable to a complementary nucleic acid and the sequence of linked units is divided into at least two regions. The linkages are selected from charged 3'-5' phosphorous, neutral 3'-5' phosphorous, charged 2'-5' phosphorous, neutral 2'-5' phosphorous or non-phosphorous linkages. A first of the regions includes nucleobases linked by non-phosphorous linkages and nucleobases that are attached to phosphate linkages via non-sugar tethering groups, and nucleosides selected from α-nucleosides linked by charged or neutral 3'-5' phosphorous linkages, α-nucleosides linked by charged or neutral 2'-5' phosphorous linkages, α-nucleosides linked by non-phosphorous linkages, 4'-thionucleosides linked by charged or neutral 3'-5' phosphorous linkages, 4'-thionucleosides linked by charged or neutral 2'-5' phosphorous linkages, 4'-thionucleosides linked by non-phosphorous linkages, carbocyclic-nucleosides linked by charged or neutral 3'-5' phosphorous linkages, carbocyclic-nucleosides linked by charged or neutral 2'-5' phosphorous linkages, carbocyclic-nucleosides linked by non-phosphorous linkages, β-nucleosides linked by charged or neutral 3'-5' linkages; β-nucleosides linked by charged or neutral 2'-5' linkages, and β-nucleosides linked by non-phosphorous linkages. A second of the regions includes only 2'-ribo-β-nucleosides linked by charged 3'-5' phosphorous linkages. In some embodiments the 3'-5' phosphorous linkages have a negative charge at physiological pH.

In certain preferred embodiments, the first region includes at least two nucleobases joined by a non-phosphate linkage such as a peptide linkage. In preferred embodiments, the compounds include a third region that is selected from the same groups as described above for the first region. In preferred embodiments, the second region is located between the first and third regions.

The invention also provides compounds that have a plurality of linked units, each of which is selected from nucleosides and nucleobases. The nucleosides are selected from α-nucleosides, β-nucleosides, 4'-thionucleosides and carbocyclic-nucleosides and the nucleobases are selected from purin-9-yl and pyrimidin-1-yl heterocyclic bases. The nucleosides and nucleobases of said units are linked together by linkages in a sequence wherein the sequence is hybridizable to a complementary nucleic acid. The sequence of linked units is divided into at least two regions. The linkages are selected from charged phosphorous, neutral phosphorous or non-phosphorous linkages. A first of the regions include α-nucleosides linked by charged or neutral 3'-5' phosphorous linkages, α-nucleosides linked by charged or neutral 2'-5' phosphorous linkages, α-nucleosides linked by non-phosphorous linkages, 4'-thionucleosides linked by charged or neutral 3'-5' phosphorous linkages, 4'-thionucleosides linked by charged or neutral 2'-5' phosphorous linkages, 4'-thionucleosides linked by non-phosphorous linkages, carbocyclic-nucleosides linked by charged or neutral phosphorous linkages, carbocyclic-nucleosides linked by non-phosphorous linkages, β-nucleosides linked by charged or neutral 3'-5' linkages, β-nucleosides linked by charged or neutral 2'-5' linkages, and β-nucleosides linked by non-phosphorous linkages. A second of the regions include nucleobases linked by non-phosphorous linkages and nucleobases that are attached to phosphate linkages via a non-sugar tethering moiety.

In certain embodiments, two regions of the instant oligomers may be linked by a hinge region. Hinge regions consist of nucleosidic or non-nucleosidic polymers which preferably facilitate the specific binding of the monomers of the oligomer regions with their targets. Generally, the oligonucleotide regions may be connected to hinge regions and/or binding moieties in either 5'→3' or 3'→45' orientations. The hinge region is designed to permit specific hybridization of the oligomer regions to their respective target sequences hinge regions applicable to the instant invention include those disclosed in U.S. Pat. No. 6,048,974, the disclosure of which is incorporated herein by reference.

In other embodiments, the invention concerns a composition comprising a gapmer composition where the wings are a modified oligomeric composition that is linked by a region of unpaired monomers. In such compositions, the wing segments are complementary to each other. Such compositions may be made by methods disclosed in U.S. Pat. No. 5,565,350, which is incorporated herein by reference.

In certain chimeric oligomeric compositions, at least one segment is modified to comprise at least one non-naturally occurring internucleoside linkages. In some compositons, the linkage is a phosphoramidate linkage. Suitable chimeric oligomeric compositions include gapmers, inverted gapmers, and hemimers. In some compositions, the modification is at one or both of the 5' and 3' terminus. Phosphoramidate compositions may be made by methods disclosed in U.S. Pat. No. 5,256,775, the disclosure of which is incorporated herein in its entirety.

In yet other embodiments, the chimeric oligomeric composition is modified at the 3'-terminal end to comprise linkages that are resistant to degradation within cells and body fluids. Such modifications include those where the modified 3'-terminal internucleotide phosphodiester linkage is a phosphotriester, phosphonate, phosphoramidate, phosphorothioate, or phosphoroselenate linkage. Such linkages are discussed in U.S. Pat. Nos. 5,491,133 and 5,220,007, which are incorporated herein by reference in their entirety.

One preferred composition comprises chimeric phosphoramidate oligonucleotides having both N3'-phosphoramidate linkages and phosphodiester linkages. In these compositions, at least one of the phosphodiester linkages is at the 3' end of the oligonucleotide. These mixed phosphodiester/phosphoramidate linkage compositions are described in U.S. Pat. No. 6,043,070, the disclosure of which is incorporated herein in its entirety by reference.

The chimeric oligomeric composition may comprise a mixed phosphate backbone oligonucleotide consisting essentially of an internal segment of modified nucleotides which activates RNase H and two modified nucleotide sequences which do not activate RNAse H, in which the two modified nucleotide sequences flank the internal segments, one on each side of the internal segment, wherein the internucleoside bridging phosphate residues of the internal segment are modified phosphates which are phosphorothioates and the internucleoside bridging phosphate residues of the two flanking modified nucleotide sequences are modified phosphate selected from the group consisting of: methyl phosphonates, phosphoromorpholidates, phosphoropiperazidates, and phosphoramidates. Such linkages are discussed in U.S. Pat. No. 6,060,456, the disclosure of which is incorporated herein by reference in its entirety.

In certain embodiments, the present compounds incorporate one or more polynucleoside segments having chirally-pure or chirally-enriched modified (non-phosphodiester) internucleoside linkages. The chirally-selected linkage segments are preferably selected to include linkages having R chirality at the asymmetric phosphorus atom of one or more of the linkage structures ("$R_p$ chirality"). Preferably, at least about 40% of the linkages in a given chirally-selected segment will be $R_p$-chiral. Also included are segments selectively including one or more $S_p$-chiral linkages. In one preferred embodiment, chirally-selected segments are situated at the terminal (3' and 5') portions of the compound, surrounding (flanking) a central RNaseH-activating region. The flanking chirally-selected segments preferably are substantially non-RNaseH-activating. The RNaseH-activating region, if linked with asymmetric (chiral) linkage groups, may alternatively or additionally be chirally selected. In a related embodiment, the RNaseH-activating region is situated at or near one terminus of the compound, and all or a portion of the remainder of the compound is chirally selected and preferably is non-RNaseH-activating.

The chirally-selected $R_p$-enriched segments of the invention serve to increase the binding affinity of the compound as compared to racemic compounds. In addition, because the chirally-selected modified linkage structures are more resistant to degradation by endo- and/or exonucleases than are non-modified phosphodiester linkages, the chirally-selected segments will tend to protect the compound from degradation in the in vivo environment. Such linkages are discussed in U.S. Pat. No. 6,262,036, the disclosure of which is incorporated herein by reference in its entirety.

In certain embodiments, the internucleoside bridging phosphate residues of the two flanking modified nucleotide sequences are methyl phosphonates. In other embodiments, the internucleoside bridging phosphate residues of the two flanking modified nucleotide sequences are phosphoromorpholidates. In yet other embodiments, the internucleoside bridging phosphate residues of the two flanking modified nucleotide sequences are phosphoropiperazidates. Still other embodiments are those where the internucleoside bridging phosphate residues of the two flanking modified nucleotide sequences are phosphoramidates. These compositions may be made by methods disclosed in U.S. Pat. Nos. 5,149,797 and 5,366,878, the disclosures of which are incorporated herein in their entirety.

Some compositions of the invention have an abasic moiety at the 3' end or at the 5' end or at both the 3' end and the 5' end of the molecule, wherein said abasic moiety lacks a nucleic acid base. Abasic moieties are discussed in U.S. Pat. No. 6,117,657, which is incorporated herein by reference in its entirety.

Other chimeric compounds of the invention comprise terminal 3'-3' and 5'-5' linkages. These compounds are stable to nucleases. These linkages are discussed in U.S. Pat. No. 5,750,669, the disclosure of which is incorporated herein by reference.

In yet another embodiment, the 3' and/or 5' end of the oligomer may be capped with one or more guanines that are not complementary to the target sequence. In some embodiments, the number of non-complementary guanines is two to six, more preferably from three to five, and still more preferably four. Use of guanine caps is discussed in U.S. Pat. No. 6,121,434, the disclosure of which is incorporated herein by reference in its entirety.

Certain embodiments comprise a composition with a terminal modification that is of the formula:

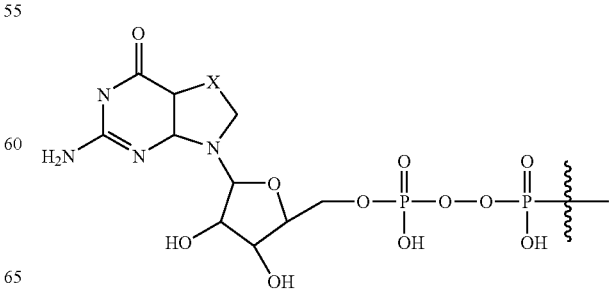

where X is N or N(CH$_3$)$^+$. In a preferred embodiment, the modification is a 5' terminal modification. This terminal group can be made by methods taught in U.S. Pat. No. 5,837,852, the disclosure of which is incorporated herein by reference in its entirety.

Hybridization

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An oligomeric compound of the invention is believed to specifically hybridize to the target nucleic acid and interfere with its normal function to cause a loss of activity. There is preferably a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the context of the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention; "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, then the position of hydrogen bonding between the oligomer and the target nucleic acid is considered to be a complementary position. The oligomeric compound and the target nucleic acid are complementary to each other when a sufficient number of complementary positions in each molecule are occupied by nucleobases that can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomer and a target nucleic acid.

It is understood in the art that the sequence of the oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). It is preferred that the oligomeric compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Targets of the Invention

"Targeting" an oligomeric compound to a particular nucleic acid molecule, in the context of this invention, can be a multistep process. The process usually begins with the identification of a target nucleic acid whose function is to be modulated. This target nucleic acid may be, for example, a mRNA transcribed from a cellular gene whose expression is associated with a particular disorder or disease state, or a nucleic acid molecule from an infectious agent.

The targeting process usually also includes determination of at least one target region, segment, or site within the target nucleic acid for the interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using oligomeric compounds targeted to, for example, pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which preferred compounds and compositions of the invention hybridize are herein below referred to as "preferred target segments." As used herein the term "preferred target segment" is defined as at least an 8-nucleobase portion of a target region to which an active antisense oligomeric compound is targeted. While not wishing to be bound by theory, it is presently believed that these target segments represent portions of the target nucleic acid that are accessible for hybridization.

Once one or more target regions, segments or sites have been identified, oligomeric compounds are chosen which are sufficiently complementary to the target, i.e., hybridize sufficiently well and with sufficient specificity, to give the desired effect.

In accordance with an embodiment of the this invention, a series of nucleic acid duplexes comprising the antisense strand oligomeric compounds of the present invention and their respective complement sense strand compounds can be designed for a specific target or targets. The ends of the strands may be modified by the addition of one or more natural or modified nucleobases to form an overhang. The sense strand of the duplex is designed and synthesized as the complement of the antisense strand and may also contain modifications or additions to either terminus. For example, in one embodiment, both strands of the duplex would be complementary over the central nucleobases, each having overhangs at one or both termini.

For the purposes of describing an embodiment of this invention, the combination of an antisense strand and a sense strand, each of can be of a specified length, for example from 18 to 29 nucleotides long, is identified as a complementary pair of siRNA oligomers. This complementary pair of siRNA oligomers can include additional nucleotides on either of their 5' or 3' ends. Further they can include other molecules or molecular structures on their 3' or 5' ends such as a phosphate group on the 5' end. A preferred group of compounds of the invention include a phosphate group on the 5' end of the antisense strand compound. Other preferred compounds also include a phosphate group on the 5' end of the sense strand compound. Even further preferred compounds would include additional nucleotides such as a two base overhang on the 3' end.

For example, a preferred siRNA complementary pair of oligomers comprise an antisense strand oligomeric compound having the sequence CGAGAGGCGGACGGGACCG (SEQ ID NO:1) and having a two-nucleobase overhang of deoxythymidine(dT) and its complement sense strand. These oligomers would have the following structure:

```
5'   cgagaggcggacgggaccgTT 3' Antisense Strand (SEQ ID NO: 2)
     |||||||||||||||||||||
3'   TTgctctccgcctgccctggc    5' Complement Strand (SEQ ID NO: 3)
```

In an additional embodiment of the invention, a single oligomer having both the antisense portion as a first region in the oligomer and the sense portion as a second region in the oligomer is selected. The first and second regions are linked together by either a nucleotide linker (a string of one or more nucleotides that are linked together in a sequence) or by a non-nucleotide linker region or by a combination of both a nucleotide and non-nucleotide structure. In each of these structures, the oligomer, when folded back on itself, would be complementary at least between the first region, the antisense portion, and the second region, the sense portion. Thus the oligomer would have a palindrome within it structure wherein the first region, the antisense portion in the 5' to 3' direction, is complementary to the second region, the sense portion in the 3' to 5' direction.

In a further embodiment, the invention includes oligomer/protein compositions. Such compositions have both an oligomer component and a protein component. The oligomer component comprises at least one oligomer, either the antisense or the sense oligomer but preferably the antisense oligomer (the oligomer that is antisense to the target nucleic acid). The oligomer component can also comprise both the antisense and the sense strand oligomers. The protein component of the composition comprises at least one protein that forms a portion of the RNA-induced silencing complex, i.e., the RISC complex.

RISC is a ribonucleoprotein complex that contains an oligomer component and proteins of the Argonaute family of proteins, among others. While we do not wish to be bound by theory, the Argonaute proteins make up a highly conserved family whose members have been implicated in RNA interference and the regulation of related phenomena. Members of this family have been shown to possess the canonical PAZ and Piwi domains, thought to be a region of protein-protein interaction. Other proteins containing these domains have been shown to effect target cleavage, including the RNAse, Dicer. The Argonaute family of proteins includes, but depending on species, are not necessary limited to, eIF2C1 and eIF2C2. eIF2C2 is also known as human GERp95. While we do not wish to be bound by theory, at least the antisense oligomer strand is bound to the protein component of the RISC complex. Additionally, the complex might also include the sense strand oligomer. Carmell et al, Genes and Development 2002, 16, 2733-2742.

Also, while we do not wish to be bound by theory, it is further believe that the RISC complex may interact with one or more of the translation machinery components. Translation machinery components include but are not limited to proteins that effect or aid in the translation of an RNA into protein including the ribosomes or polyribosome complex. Therefore, in a further embodiment of the invention, the oligomer component of the invention is associated with a RISC protein component and further associates with the translation machinery of a cell. Such interaction with the translation machinery of the cell would include interaction with structural and enzymatic proteins of the translation machinery including but not limited to the polyribosome and ribosomal subunits.

In a further embodiment of the invention, the oligomer of the invention is associated with cellular factors such as transporters or chaperones. These cellular factors can be protein, lipid or carbohydrate based and can have structural or enzymatic functions that may or may not require the complexation of one or more metal ions.

Furthermore, the oligomer of the invention itself may have one or more moieties which are bound to the oligomer which facilitate the active or passive transport, localization or compartmentalization of the oligomer. Cellular localization includes, but is not limited to, localization to within the nucleus, the nucleolus or the cytoplasm. Compartmentalization includes, but is not limited to, any directed movement of the oligomers of the invention to a cellular compartment including the nucleus, nucleolus, mitochondrion, or imbedding into a cellular membrane surrounding a compartment or the cell itself.

In a further embodiment of the invention, the oligomer of the invention is associated with cellular factors that affect gene expression, more specifically those involved in RNA modifications. These modifications include, but are not limited to posttrascriptional modifications such as methylation. Furthermore, the oligomer of the invention itself may have one or more moieties which are bound to the oligomer which facilitate the posttranscriptional modification.

The oligomeric compounds of the invention may be used in the form of single-stranded, double-stranded, circular or hairpin oligomeric compounds and may contain structural elements such as internal or terminal bulges or loops. Once introduced to a system, the oligomeric compounds of the invention may interact with or elicit the action of one or more enzymes or may interact with one or more structural proteins to effect modification of the target nucleic acid.

One non-limiting example of such an interaction is the RISC complex. Use of the RISC complex to effect cleavage of RNA targets thereby greatly enhances the efficiency of oligomer-mediated inhibition of gene expression. Similar roles have been postulated for other ribonucleases such as those in the RNase III and ribonuclease L family of enzymes.

Preferred forms of oligomeric compound of the invention include a single-stranded antisense oligomer that binds in a RISC complex, a double stranded antisense/sense pair of oligomer or a single strand oligomer that includes both an antisense portion and a sense portion. Each of these compounds or compositions is used to induce potent and specific modulation of gene function. Such specific modulation of gene function has been shown in many species by the introduction of double-stranded structures, such as double-stranded RNA (dsRNA) molecules and has been shown to induce potent and specific antisense-mediated reduction of the function of a gene or its associated gene products. This phenomenon occurs in both plants and animals and is believed to have an evolutionary connection to viral defense and transposon silencing.

The compounds and compositions of the invention are used to modulate the expression of a target nucleic acid. "Modulators" are those oligomeric compounds that decrease or increase the expression of a nucleic acid molecule encoding a target and which comprise at least an 8-nucleobase portion that is complementary to a preferred target segment. The screening method comprises the steps of contacting a preferred target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

Oligomeric Compounds

In the context of the present invention, the term "oligomeric compound" refers to a polymeric structure capable of hybridizing a region of a nucleic acid molecule. This term includes oligonucleotides, oligonucleosides, oligonucleotide analogs, oligonucleotide mimetics and combinations of these. Oligomeric compounds are routinely prepared linearly but can be joined or otherwise prepared to be circular, and may also include branching. Oligomeric compounds can hybridized to form double stranded compounds that can be blunt ended or may include overhangs. In general an oligomeric compound comprises a backbone of linked monomeric subunits where each linked monomeric subunit is directly or indirectly attached to a heterocyclic base moiety. The linkages joining the monomeric subunits, the sugar moieties or surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligomers, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligomer structure, the phosphate groups are commonly referred to as forming the internucleoside linkages of the oligomer. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions which function in a similar manner to oligonulceotides. Such non-naturally occurring oligonucleotides are often preferred over the naturally occurring forms because of desirable properties such as, for example, enhanced cellular uptake, enhanced affinity for nucleic acid target and increased stability in the presence of nucleases.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetal, formacetal, thioformacetal, methylene formacetal, thioformacetal, alkeneyl, sulfamate; methyleneimino, methylenehydrazino, sulfonate, sulfonamide, amide and others having mixed N, O, S and $CH_2$ component parts.

In addition to the modifications described above, the nucleosides of the oligomeric compounds of the invention can have a variety of other modifications so long as these other modifications either alone or in combination with other nucleosides enhance one or more of the desired properties described above. Thus, for nucleotides that are incorporated into oligomers of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

Altered base moieties or altered sugar moieties also include other modifications consistent with the spirit of this invention. Such oligomers are best described as being structurally distinguishable from, yet functionally interchangeable with, naturally occurring or synthetic wild type oligonucleotides. All such oligomers are comprehended by this invention so long as they function effectively to mimic the structure of a desired RNA or DNA strand. A class of representative base modifications include tricyclic cytosine analog, termed "G clamp" (Lin, et al., *J. Am. Chem. Soc.* 1998, 120, 8531). This analog makes four hydrogen bonds to a complementary guanine (G) within a helix by simultaneously recognizing the Watson-Crick and Hoogsteen faces of the targeted G. This G clamp modification when incorporated into phosphorothioate oligomers, dramatically enhances antisense potencies in cell culture. The oligomers of the invention also can include phenoxazine-substituted bases of the type disclosed by Flanagan, et al., *Nat. Biotechnol.* 1999, 17(1), 48-52.

The oligomeric compounds in accordance with this invention preferably comprise from about 8 to about 80 nucleobases (i.e. from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the oligomeric compounds of the invention are 12 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the oligomeric compounds of the invention are 15 to 30 nucleobases in length. One having ordinary skill in the art will appreciate that this embodies oligomeric compounds of 15, 16, 17, 18, 19, 20, 21, 22, 23, 24, 25, 26, 27, 28, 29, or 30 nucleobases in length.

Particularly preferred oligomeric compounds are oligomers from about 15 to about 30 nucleobases, even more preferably those comprising from about 21 to about 24 nucleobases.

General Oligomer Synthesis

Oligomerization of modified and unmodified nucleosides is performed according to literature procedures for DNA-like compounds (Protocols for Oligonucleotides and Analogs, Ed. Agrawal (1993), Humana Press) and/or RNA like compounds (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

RNA oligomers can be synthesized by methods disclosed herein or purchased from various RNA synthesis companies such as for example Dharmacon Research Inc., (Lafayette, Colo.).

Irrespective of the particular protocol used, the oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

For double stranded structures of the invention, once synthesized, the complementary strands preferably are annealed. The single strands are aliquoted and diluted to a concentration of 50 uM. Once diluted, 30 uL of each strand is combined with 15uL of a 5×solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexes are evaluated for their ability to modulate target expression. When cells reach 80% confluency, they are treated with synthetic duplexes comprising at least one oligomeric compound of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligomers, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligomers, the phosphate groups are commonly referred to as forming the internucleoside linkage or in conjunction with the sugar ring the backbone of the oligomer. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligomers containing modified e.g. non-naturally occurring internucleoside linkages. As defined in this specification, oligomers having modified internucleoside linkages include internucleoside linkages that retain a phosphorus atom and internucleoside linkages that do not have a phosphorus atom. For the purposes of this specification, and as sometimes referenced in the art, modified oligomers that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligomer backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligomers having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but-are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester internucleotide linkage is represented as —O—P(=O)(OH)—O—$CH_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligomer backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetal and thioformacetal backbones; methylene formacetal and thioformacetal backbones; riboacetal backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., Science, 1991, 254, 1497-1500.

One oligonucleotide mimetic that has been reported to have excellent hybridization properties is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

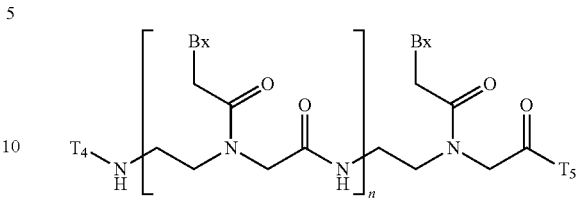

wherein

Bx is a heterocyclic base moiety;

$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, Biochemistry, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

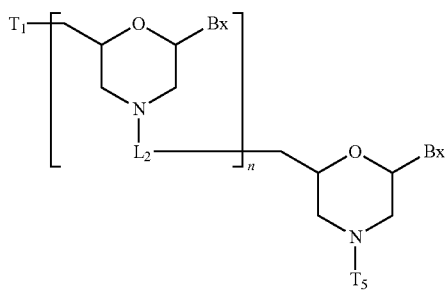

wherein

T$_1$ is hydroxyl or a protected hydroxyl;

T$_5$ is hydrogen or a phosphate or phosphate derivative;

L$_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligomers having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

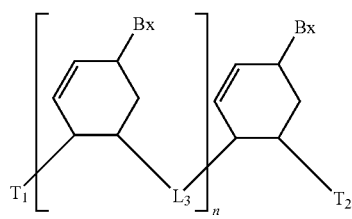

wherein each Bx is a heterocyclic base moiety;

T$_1$ is hydroxyl or a protected hydroxyl; and

T2 is hydroxyl or a protected hydroxyl.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

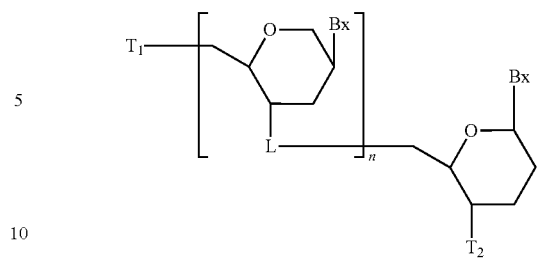

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene (—CH$_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

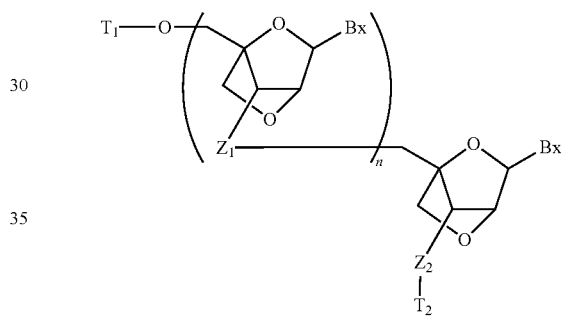

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligomers containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

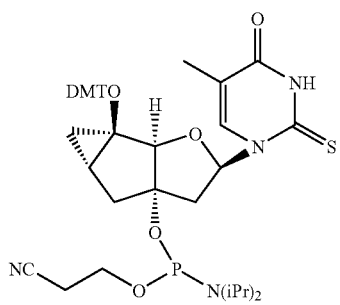

-continued

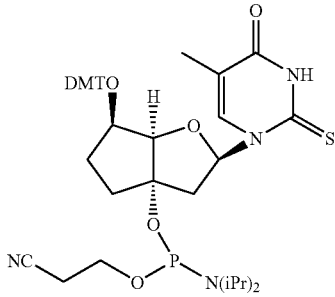

(see Steffens et al., *Helv. Chim. Acta,* 1997, 80, 2426-2439; Steffens et al., *J. Am. Chem. Soc.,* 1999, 121, 3249-3255; and Renneberg et al., *J. Am. Chem. Soc.,* 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of variables see: U.S. Pat. Nos. 5,874,553 and 6,127,346 herein incorporated by reference in their entirety) is shown below.

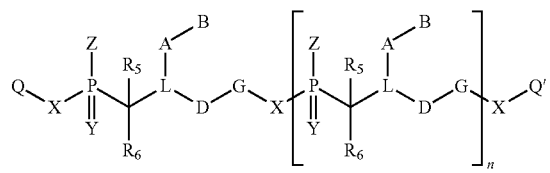

Another oligonucleotide mimetic has been reported wherein the furanosyl ring has been replaced by a cyclobutyl moiety.

Modified Sugars

Oligomeric compounds of the invention may also contain one or more substituted sugar moieties. Preferred oligomeric compounds comprise a sugar substituent group selected from: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligomers comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomer, or a group for improving the pharmacodynamic properties of an oligomer, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other preferred sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligomers and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula $I_a$ or $II_a$:

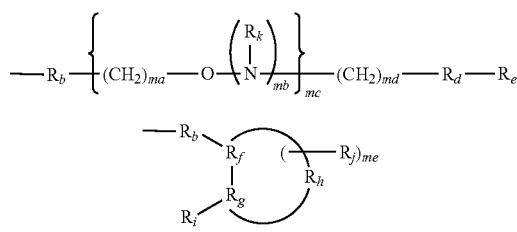

Ia

IIa wherein:

$R_b$ is O, S or NH;

$R_d$ is a single bond, O, S or C(=O);

$R_e$ is $C_1$-$C_{10}$ alkyl, $N(R_k)(R_m)$, $N(R_k)(R_n)$, N=$C(R_p)(R_q)$, N=$C(R_p)(R_r)$ or has formula $III_a$;

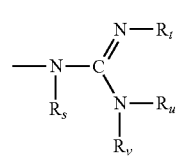

IIIa $R_p$ and $R_q$ are each independently hydrogen or $C_1$-$C_{10}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, a nitrogen protecting group or —$R_x$—$R_y$;

$R_p$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituent groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

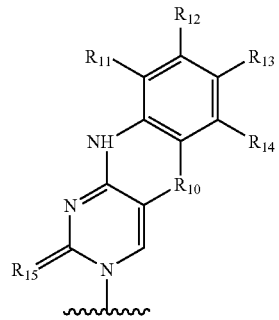

Representative cytosine analogs that make 3 hydrogen bonds with a guanosine in a second strand include 1,3-diazaphenoxazine-2-one ($R_{10}$=O, $R_{11}$—$R_{14}$=H) [Kurchavov, et al., *Nucleosides and Nucleotides*, 1997, 16, 1837-1846], 1,3-diazaphenothiazine-2-one ($R_{10}$=S, $R_{11}$—$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$—$R_{14}$=F) [Wang, J.; Lin, K.-Y., Matteucci, M. Tetrahedron Lett. 1998, 39, 8385-8388]. Incorporated into oligomers these base modifications were shown to hybridize with complementary guanine and the latter was also shown to hybridize with adenine and to enhance helical thermal stability by extended stacking interactions (also see U.S. Patent Application entitled "Modified Peptide Nucleic Acids" filed May 24, 2002, Ser. No. 10/155,920; and U.S. Patent Application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. Ser. No. 6,028,183, which issued on May 22, 2000, and U.S. Pat. Ser. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity make them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligomer design and to better understand the impact of these heterocyclic modifications on the biological activity, it is important to evaluate their effect on the nuclease stability of the oligomers.

Further modified polycyclic heterocyclic compounds useful as heterocyclcic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and Unites States patent application Ser. No. 09/996,292 filed Nov. 28, 2001, certain of which are commonly owned with the instant application, and each of which is herein incorporated by reference.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., dihexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligomer-drug conjugates and their preparation are described in U.S. patent application Ser. No. 09/334,130 (filed Jun. 15, 1999) which is incorporated herein by reference in its entirety.

Representative United States patents that teach the preparation of such oligomer conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

3'-endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Conformation Scheme

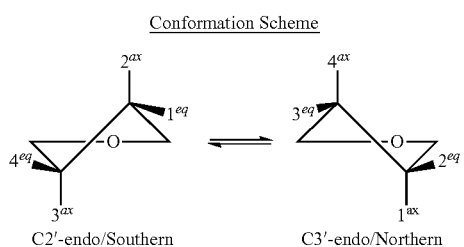

C2'-endo/Southern      C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Table I. These examples are meant to be representative and not exhaustive.

TABLE I

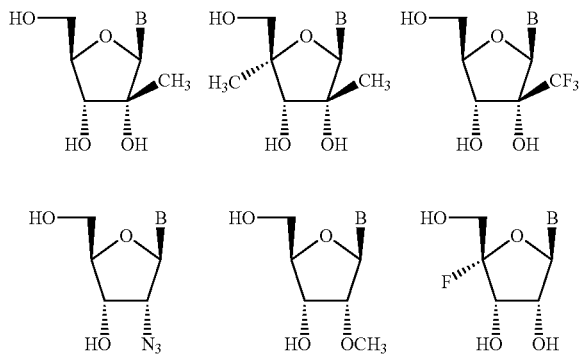

TABLE I-continued

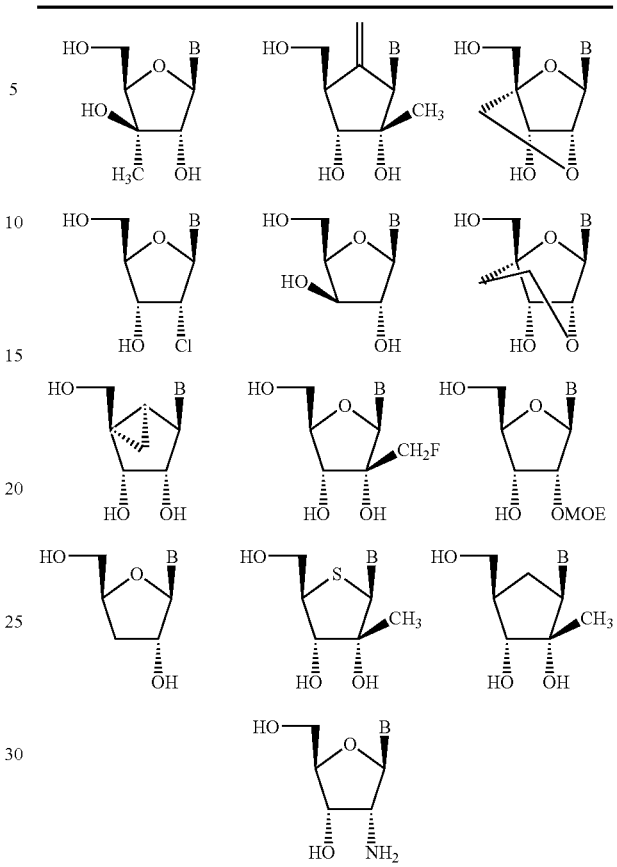

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.)

In one aspect, the present invention is directed to oligomers that are prepared having enhanced properties compared to native RNA against nucleic acid targets. A target is identified and an oligomer is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504.) In general, RNA:RNA duplexes are more stable and have higher melting temperatures (Tm's) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research*, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed between a target RNA and a synthetic sequence is central to therapies such as but not limited to antisense and RNA interference as these mechanisms require the binding of a synthetic oligomer strand to an RNA target strand. In the case of antisense, effective inhibition of the mRNA requires that the antisense DNA have a very high binding affinity with the mRNA. Otherwise the desired interaction between the synthetic oligomer strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligomers having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligomers having the 2'-MOE modification displayed improved RNA affinity and higher nuclease resistance. Chimeric oligomers having 2'-MOE substituents in the wing nucleosides and an internal region of deoxy-phosphorothioate nucleotides (also termed a gapped oligomer or gapmer) have shown effective reduction in the growth of tumors in animal models at low doses. 2'-MOE substituted oligomers have also shown outstanding promise as antisense agents in several disease states. One such MOE substituted oligomer is presently being investigated in clinical trials for the treatment of CMV retinitis.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

The term haloalkyl is defined as an alkyl containing one or more halogen atoms. In some embodiments, the alkyl is fully halogenated. For example, the haloalkyl may be trifluoromethyl. Similarly, the term haloalkoxy is defined as an alkoxy group where the alkyl group is a haloalkyl. For example, the haloalkoxy may be trifluoroalkoxy.

Unless otherwise defined herein, where a moiety is defined as a compound moiety, such as hetarylalkyl (hetaryl and alkyl), aralkyl (aryl and alkyl), haloalkyl, etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g.—$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

Screening, Target Validation and Drug Discovery

For use in screening and target validation, the compounds and compositions of the invention are used to modulate the expression of a selected protein. "Modulators" are those oligomeric compounds and compositions that decrease or increase the expression of a nucleic acid molecule encoding a protein and which comprise at least an 8-nucleobase portion which is complementary to a preferred target segment. The screening method comprises the steps of contacting a preferred target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The conduction such screening and target validation studies, oligomeric compounds of invention can be used combined with their respective complementary strand oligomeric compound to form stabilized double-stranded (duplexed) oligomers. Double stranded oligomer moieties have been shown to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200; Nishikura et al., Cell (2001), 107, 415-416; and Bass et al., Cell (2000), 101, 235-238.) For example, such double-stranded moieties have been shown to inhibit the target by the classical hybridization of antisense strand of the duplex to the target, thereby triggering enzymatic degradation of the target (Tijsterman et al., Science, 2002, 295, 694-697).

For use in drug discovery and target validation, oligomeric compounds of the present invention are used to elucidate relationships that exist between proteins and a disease state, phenotype, or condition. These methods include detecting or modulating a target peptide comprising contacting a sample, tissue, cell, or organism with the oligomeric compounds and compositions of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a disease or disorder.

Kits, Research Reagents, Diagnostics, and Therapeutics

The oligomeric compounds and compositions of the present invention can additionally be utilized for diagnostics, therapeutics, prophylaxis and as research reagents and kits. Such uses allows for those of ordinary skill to elucidate the function of particular genes or to distinguish between functions of various members of a biological pathway.

For use in kits and diagnostics, the oligomeric compounds and compositions of the present invention, either alone or in combination with other compounds or therapeutics, can be used as tools in differential and/or combinatorial analyses to elucidate expression patterns of a portion or the entire complement of genes expressed within cells and tissues.

As one non-limiting example, expression patterns within cells or tissues treated with one or more compounds or compositions of the invention are compared to control cells or tissues not treated with the compounds or compositions and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compounds and compositions of the invention are useful for research and diagnostics, because these compounds and compositions hybridize to nucleic acids encoding proteins. Hybridization of the compounds and compositions of the invention with a nucleic acid can be detected by means known in the art. Such means may include conjugation of an enzyme to the compound or composition, radiolabelling or any other suitable detection means. Kits using such detection means for detecting the level of selected proteins in a sample may also be prepared.

The specificity and sensitivity of compounds and compositions can also be harnessed by those of skill in the art for therapeutic uses. Antisense oligomeric compounds have been employed as therapeutic moieties in the treatment of disease states in animals, including humans. Antisense oligomer drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, preferably a human, suspected of having a disease or disorder that can be treated by modulating the expression of a selected protein is treated by administering the compounds and compositions. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In one embodiment, the activity or expression of a protein in an animal is inhibited by about 10%. Preferably, the activity or expression of a protein in an animal is inhibited by about 30%. More preferably, the activity or expression of a protein in an animal is inhibited by 50% or more.

For example, the reduction of the expression of a protein may be measured in serum, adipose tissue, liver or any other body fluid, tissue or organ of the animal. Preferably, the cells contained within the fluids, tissues or organs being analyzed contain a nucleic acid molecule encoding a protein and/or the protein itself.

The compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

Formulations

The compounds and compositions of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds and compositions of the invention: i.e., salts that retain the desired biological activity of the parent compound and do not impart undesired toxicological effects thereto. For oligomers, preferred examples of pharmaceutically acceptable salts and their uses are further described in U.S. Pat. No. 6,287,860, which is incorporated herein in its entirety.

The present invention also includes pharmaceutical compositions and formulations that include the compounds and compositions of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compounds and compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligomers of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, compounds and compositions of the invention may be encapsulated within liposomes or may form complexes thereto, in particular to cationic liposomes. Alternatively, they may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets.

Thickeners, flavoring agents, diluents, emulsifiers, dispersing aids or binders may be desirable. Preferred oral formulations are those in which oligomers of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/ salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Compounds and compositions of the invention may be delivered orally, in granular form including sprayed dried particles, or complexed to form micro or nanoparticles. Complexing agents and their uses are further described in U.S. Pat. No. 6,287,860, which is incorporated herein in its entirety. Certain oral formulations for oligomers and their preparation are described in detail in U.S. application Ser. Nos. 09/108, 673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more of the compounds and compositions of the invention and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the oligomeric compounds of the invention, such chemotherapeutic agents may be used individually (e.g., 5-FU and oligomer), sequentially (e.g., 5-FU and oligomer for a period of time followed by MTX and oligomer), or in combination with one or more other such chemotherapeutic agents (e.g., 5-FU, MTX and oligomer, or 5-FU, radiotherapy and oligomer). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of compounds and compositions of the invention and other drugs are also within the scope of this invention. Two or more combined compounds such as two oligomeric compounds or one oligomeric compound combined with further compounds may be used together or sequentially.

In another related embodiment, compositions of the invention may contain one or more of the compounds and compositions of the invention targeted to a first nucleic acid and one or more additional compounds such as antisense oligomeric compounds targeted to a second nucleic acid target. Numerous examples of antisense oligomeric compounds are known in the art. Alternatively, compositions of the invention may contain two or more oligomeric compounds and compositions targeted to different regions of the same nucleic acid target. Two or more combined compounds may be used together or sequentially Dosing The formulation of therapeutic compounds and compositions of the invention and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

The entire disclosure of each patent, patent application, and publication cited or described in this document is hereby incorporated by reference.

EXAMPLE 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-NN-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N$^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N$^4$-isobutyrylguanosin-3'-O-yl]-2-cyanoethyl-NN-diisopropylphosphoramidite (MOE G amidite), 2'-O-(Aminooxyethyl) nucleoside amidites and 2'-O-(dimethylaminooxy-ethyl) nucleoside amidites, 2'-(Dimethylaminooxyethoxy) nucleoside amidites, 5'-O-tert-Butyldiphenylsilyl-O$_2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyi-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

EXAMPLE 2

Oligomer and Oligonucleoside Synthesis

Oligomers: Unsubstituted and substituted phosphodiester (P=O) oligomers are synthesized on an automated DNA synthesizer (Applied Biosystems model 394) using standard phosphoramidite chemistry with oxidation by iodine.

Phosphorothioates (P=S) are synthesized similar to phosphodiester oligomers with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligomers were recovered by precipitating with >3 volumes of ethanol from a 1 M NH$_4$OAc solution. Phosphinate oligomers are prepared as described in U.S. Pat. No. 5,508,270, herein incorporated by reference.

Alkyl phosphonate oligomers are prepared as described in U.S. Pat. No. 4,469,863, herein incorporated by reference.

3'-Deoxy-3'-methylene phosphonate oligomers are prepared as described in U.S. Pat. Nos. 5,610,289 or 5,625,050, herein incorporated by reference.

Phosphoramidite oligomers are prepared as described in U.S. Pat. No. 5,256,775 or U.S. Pat. No. 5,366,878, herein incorporated by reference.

Alkylphosphonothioate oligomers are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligomers are prepared as described in U.S. Pat. No. 5,476,925, herein incorporated by reference.

Phosphotriester oligomers are prepared as described in U.S. Pat. No. 5,023,243, herein incorporated by reference.

Borano phosphate oligomers are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleo-sides, as well as mixed backbone oligomeric compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

EXAMPLE 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligomer synthesis. However, after oligomer synthesis the oligomer is treated with methylamine which not only cleaves the oligomer from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligomer synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand,.* 1990, 44, 639-641; Reddy, M. P., et al., *Tetrahedrom Lett.*, 1994, 25, 43114314; Wincott, F. et al., *Nucleic Acids Res.*, 1995, 23, 2677-2684; Griffin, B. E., et al., *Tetrahedron,* 1967, 23, 2301-2313; Griffin, B. E., et al., *Tetrahedron,* 1967, 23, 2315-2331).

EXAMPLE 4

Synthesis of Chimeric Oligomers

Chimeric oligomers, oligonucleosides or mixed oligomers/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligomers of the first type are also known in the art as "gapmers" or gapped oligomers. Oligomers of the second type are also known in the art as "hemimers" or "wingmers".

[2'-O—Me]-[2'-deoxy]-[2'-O-Me] Chimeric Phosphorothioate Oligomers

Chimeric oligomers having 2'-O-alkyl phosphorothioate and 2'-deoxy phosphorothioate oligomer segments are synthesized using an Applied Biosystems automated DNA synthesizer Model 394, as above. Oligomers are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligomer is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligomers

[2'-O-(2-methoxyethyl)]-[2'-deoxy]-[-2'-O-(methoxyethyl)] chimeric phosphorothioate oligomers were prepared as per the procedure above for the 2'-O-methyl chimeric oligomer, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligomers

[2'-O-(2-methoxyethyl phosphodiester]-[2'-deoxy phosphorothioate]-[2'-O -(methoxyethyl) phosphodiester] chimeric oligomers are prepared as per the above procedure for the 2'-O-methyl chimeric oligomer with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligomers, chimeric oligonucleosides and mixed chimeric oligomers/oligonucleosides are synthesized according to U.S. Pat. No. 5,623,065, herein incorporated by reference.

EXAMPLE 5

Low Load t-butyloxycarbonylglycyl Merrifield Resin t-Butyloxycarbonylglycyl Merrifield resin may be synthesized methods detailed in U.S. Pat. No. 5,700,922.

EXAMPLE 6

Oligomer Having 2'-Substituted Oligomer Regions Flanking A Central 2'-Deoxy Phosphoroselenate Oligomer Region The aforementioned composition may be synthesized methods detailed in U.S. Pat. No. 5,623,065.

Example 7

T(5'-Amino)-$G^{PAC}$-$C^{PAC}$-$A^{PAC}$-T-T(3'-Carboxy)-T(p)-$C^z$(p)-$A^z$(p)-$G^z$(p)-Gly-O-Resin (SEQ ID No. 76)

The aforementioned composition may be synthesized methods detailed in U.S. Pat. No. 5,700,922.

EXAMPLE 8

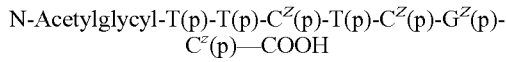

The aforementioned composition may be synthesized methods detailed in U.S. Pat. No. 5,700,922.

EXAMPLE 9

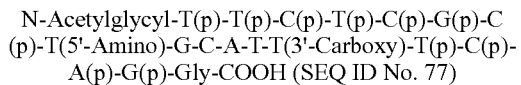

The aforementioned composition may be synthesized methods detailed in U.S. Pat. No. 5,700,922.

EXAMPLE 10

Synthesis of Hybrid Oligomer Phosphorothioates

Hybrid oligomeric phosphorthioates may be made by methods disclosed in U.S. Pat. No. 5,652,355.

EXAMPLE 11

Oligomer Having a Oligomer Regions Flanking Central Beta Oligomer Region

A. α-β Mixed Oligomer Having Non-Symmetrical 3'-3' and 5'-5' Linkages

α-β Mixed oligomers having non-symmetrical 3'-3' and 5'-5' linkages may be synthesized by methods taught in U.S. Pat. No. 5,623,065.

B. α-β Mixed Oligomer Having Symmetrical 4 Atom Linkages

α-β Mixed oligomers having symmetrical 4 atom linkages may be synthesized by methods taught in U.S. Pat. No. 5,623,065.

EXAMPLE 12

Oligomer Having 2'-5' Phosphodiester Oligomer Regions Flanking a Central 2'-Deoxy 3'-5' Phosphorothioate Oligomer Region The aforementioned compositions may be synthesized by methods taught in U.S. Pat. No. 5,623,065.

EXAMPLE 13

Macromolecule Having Regions of Cyclobutyl Surrogate Nucleosides Linked by Phosphodiester Linkages Flanking a Central 2'-Deoxy 3'-5' Phosphorothioate Oligomer Region The aforementioned compositions may be synthesized by methods taught in U.S. Pat. No. 5,623,065.

EXAMPLE 14

Oligomer Having 4'-Thionucleotide Regions Flanking a Central 2'-Deoxy Phosphorothioate Oligomer Region The aforementioned compositions may be synthesized by methods taught in U.S. Pat. No. 5,623,065.

EXAMPLE 15

Oligomer Having 2'-Substituted Methyl Phosphonate Linked Oligomer Regions Flanking a Central 2'-Deoxy Phosphorothioate Oligomer Region The aforementioned compositions may be synthesized by methods taught in U.S. Pat. No. 5,623,065.

EXAMPLE 16

Oligomer Having Phosphoramidate Linkages at the 3' and 5' Terminal Segments Flanking a Diester Linked Segment The aforementioned compositions may be synthesized by methods taught in U.S. Pat. No. 5,256,775.

EXAMPLE 17

Oligomer Having 2'-O-Methyl-Nucleotide Segments Flanking a Deoxynucleotide Segment The aforementioned compositions may be synthesized by methods taught in U.S. Pat. No. 5,013,830.

EXAMPLE 18

Design and Screening of Duplexed Oligomeric Compounds Targeting a Target

In accordance with the present invention, a series of nucleic acid duplexes comprising the antisense oligomeric compounds of the present invention and their complements can be designed to target a target. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO:1) and having a two-nucleobase overhang of deoxythymidine(dT) would have the following structure:

```
5'  cgagaggcggacgggaccgTT 3'  Antisense Strand (SEQ ID NO: 2)
    |||||||||||||||||||
3'  TTgctctccgcctgccctggc     5' Complement Strand (SEQ ID NO: 3)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5×solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense oligomeric compounds are evaluated for their ability to modulate a target expression.

When cells reached 80% confluency, they are treated with duplexed antisense oligomeric compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense oligomeric compound at a final concentration of 200 nM. After 5 hours of treatment, the medium is replaced with fresh medium. Cells are harvested 16 hours after treatment, at which time RNA is isolated and target reduction measured by RT-PCR.

EXAMPLE 19

Oligomer Isolation

After cleavage from the controlled pore glass solid support and deblocking in concentrated ammonium hydroxide at 55° C. for 12-16 hours, the oligomers or oligonucleosides are recovered by precipitation out of 1 M NH$_4$OAc with >3 volumes of ethanol. Synthesized oligomers were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligomers were purified by HPLC, as described by Chiang et al., *J. Biol. Chem.* 1991, 266, 18162-18171. Results obtained with HPLC-purified material were similar to those obtained with non-HPLC purified material.

EXAMPLE 20

Oligomer Synthesis—96 Well Plate Format

Oligomers were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldi-isopropyl phosphoramidites.

Oligomers were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

EXAMPLE 21

Oligomer Analysis—96-Well Plate Format

The concentration of oligomer in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the oligomeric compounds utilizing electrospray-mass spectroscopy. All assay test plates were diluted from the master plate using single and multi-channel robotic pipettors. Plates were judged to be acceptable if at least 85% of the oligomeric compounds on the plate were at least 85% full length.

EXAMPLE 22

Cell Culture and Oligomer Treatment

The effect of oligomeric compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligomer.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per 1 nL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with antisense oligomeric compounds:

When cells reached 65-75% confluency, they were treated with oligomer. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligomer. Cells are treated and data are obtained in triplicate. After 4-7 hours of treatment at 37° C., the medium was replaced with fresh medium. Cells were harvested 16-24 hours after oligomer treatment.

The concentration of oligomer used varies from cell line to cell line. To determine the optimal oligomer concentration for a particular cell line, the cells are treated with a positive control oligomer at a range of concentrations. For human cells the positive control oligomer is selected from either ISIS 13920 (TCCGTCATCGCTCCTCAGGG, SEQ ID NO: 4) which is targeted to human H-ras, or ISIS 18078, (GTGCGCGCGAGCCCGAAATC, SEQ ID NO: 5) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligomer is ISIS 15770, ATG-CATTCTGCCCCCAAGGA (SEQ ID NO: 6) a 2'-O-methoxyethyl gapmer (2'-O -methoxyethyls shown in bold) with a phosphorothioate backbone which is targeted to both mouse and rat c-raf. The concentration of positive control oligomer that results in 80% inhibition of c-H-ras (for ISIS 13920), JNK2 (for ISIS 18078) or c-raf (for ISIS 15770) mRNA is then utilized as the screening concentration for new oligomers in subsequent experiments for that cell line. If 80% inhibition is not achieved, the lowest concentration of positive control oligomer that results in 60% inhibition of c-H-ras, JNK2 or c-raf mRNA is then utilized as the oligomer screening concentration in subsequent experiments for that cell line. If 60% inhibition is not achieved, that particular cell line is deemed as unsuitable for oligomer transfection experiments. The concentrations of antisense oligomers used herein are from 50 nM to 300 nM.

EXAMPLE 23

Analysis of Oligomer Inhibition of a Target Expression

Modulation of a target expression can be assayed in a variety of ways known in the art. For example, a target mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

EXAMPLE 24

Design of Phenotypic Assays and in Vivo Studies for the Use of a Target Inhibitors Phenotypic Assays Once a target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints. Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or a target inhibitor. Furthermore, to prevent the doctors from being biased in treatments, they are not informed as to whether the medication they are administering is a a target inhibitor or a placebo. Using this randomization approach, each volunteer has the same chance of being given either the new treatment or the placebo.

Volunteers receive either the a target inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding a target or a target protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and a target inhibitor treatment. In general, the volunteers treated with placebo have little or no response to treatment, whereas the volunteers treated with the target inhibitor show positive trends in their disease state or condition index at the conclusion of the study.

EXAMPLE 25

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY$_{96}$™ well plate attached to a QIA-VAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIA-VAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

EXAMPLE 26

Real-time Quantitative PCR Analysis of a Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligomer probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligomer treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (*Analytical Biochemistry*, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers are designed to hybridize to a human a target sequence, using published sequence information.

EXAMPLE 27

Northern Blot Analysis of a Target mRNA Levels

Eighteen hours after treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBONDTM-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human a target, a human a target specific primer probe set is prepared by PCR To normalize for variations in loading and transfer efficiency membranes are stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

EXAMPLE 28

Inhibition of Human a Target Expression by Oligomers

In accordance with the present invention, a series of oligomeric compounds are designed to target different regions of the human target RNA. The oligomeric compounds are analyzed for their effect on human target mRNA levels by quantitative real-time PCR as described in other examples herein. Data are averages from three experiments. The target regions to which these preferred sequences are complementary are herein referred to as "preferred target segments" and are therefore preferred for targeting by oligomeric compounds of the present invention. The sequences represent the reverse complement of the preferred antisense oligomeric compounds.

As these "preferred target segments" have been found by experimentation to be open to, and accessible for, hybridization with the antisense oligomeric compounds of the present invention, one of skill in the art will recognize or be able to ascertain, using no more than routine experimentation, further embodiments of the invention that encompass other oligomeric compounds that specifically hybridize to these preferred target segments and consequently inhibit the expression of a target.

According to the present invention, antisense oligomeric compounds include antisense oligomeric compounds, antisense oligomers, ribozymes, external guide sequence (EGS) oligomers, alternate splicers, primers, probes, and other short oligomeric compounds that hybridize to at least a portion of the target nucleic acid.

EXAMPLE 29

Western Blot Analysis of a Target Protein Levels

Western blot analysis (immunoblot analysis) is carried out using standard methods. Cells are harvested 16-20 h after oligomer treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

EXAMPLE 30

Blockmer Walk of 5 2'-O-methy Modified Nucleosides in the Antisense Strand of siRNA's Assayed for PTEN mRNA Levels Against Untreated Control The antisense (AS) strands listed below having SEQ ID NO: 8 were individually duplexed with the sense (S) strand having SEQ ID NO: 7 and the activity was measured to determine the relative positional effect of the 5 modifications.

| SEQ ID NO:/ ISIS NO | Sequence |
|---|---|
| 7/271790(S) | 5'-CAAAUCCAGAGGCUAGCAG-dTdT-3' |
| 8/271071(AS) | 3'-dTdT-GUUUAGGUCUCCG<u>AUCGUC</u>-5' |
| 9/271072(AS) | 3'-dTdT-GUUUAGGUCUCCG<u>AUCGU</u>C -5' |
| 10/271073(AS) | 3'-dTdT-GUUUAGGUCUCC<u>GAUCG</u>UC-5' |
| 11/271074(AS) | 3'-dTdT-GUUUAGGUCUC<u>CGAUC</u>GUC-5' |
| 12/271075(AS) | 3'-dTdT-GUUUAGGUCU<u>CCGAU</u>CGUC-5' |

Underlined nucleosides are 2'-O-methyl modified nucleosides, dT's are deoxy thymidines, all other nucleosides are ribonucleosides and all internucleoside linkages are phosphodiester.

The siRNA's having 5,2'-O-methyl groups at least 2 positions removed from the 5'-end of the antisense strand reduced PTEN mRNA levels to from 25 to 35% of untreated control. The remaining 2 constructs increased PTEN mRNA levels above untreated control.

EXAMPLE 31

Solid Block of 2'-O-methyl Modified Nucleosides in the Antisense Strand of siRNA's Assayed for PTEN mRNA Levels Against Untreated Control The antisense strands listed below having SEQ ID NO:9 were individually duplexed with the sense strand having SEQ ID NO:7 and the activity was measured to determine the relative effect of adding either 9 or 14, 2'-O-methyl modified nucleosides at the 3'-end of the resulting siRNA's.

| SEQ ID NO:/ ISIS NO | Sequence |
|---|---|
| 7/271790(S) | 5'-CAAAUCCAGAGGCUAGCAG-dTdT-3' |
| 13/271079(AS) | 3'-<u>UUGUUUAGGU</u>CUCCGAUCGUC-5' |
| 14/271081(AS) | 3'-<u>UUGUUUAGGUCUCCG</u>AUCGUC-5' |

Underlined nucleosides are 2'-O-methyl modified nucleosides, dT's are deoxy thymidines, all other nucleosides are ribonucleosides and all internucleoside linkages are phosphodiester.

The siRNA having 9, 2'-O-methyl nucleosides reduced PTEN mRNA levels to about 40% of untreated control whereas the construct having 14, 2'-O-methyl nucleosides only reduced PTEN mRNA levels to about 98% of control.

EXAMPLE 32

2'-O-methy Blockmers (siRNA vs asRNA)

A series of blockmers were prepared as duplexed siRNA's and also as single strand asRNA's. The antisense strands were identical for the siRNA's and the asRNA's. Underlined nucleosides are 2'-O-methyl modified nucleosides, all other nucleosides are ribonucleosides and all internucleoside linkages for the AS strands are phosphorothioate and the intemucleoside linkages for the S strand are phosphodiester.

| SEQ ID NO:/ ISIS NO | Sequence 5'-3' | |
|---|---|---|
| 15/308746 (S) | 5'-AAGUAAGGACCAGAGACAAA-3' | (PO) |
| 16/303912 (AS) | 3'-UUCAUUCCGGUCUCUGUUU-P 5' | (PS) |
| 17/316449 (AS) | 3'-<u>UUC</u>AUUCCUGGUCUCUGUUU-P 5' | (PS) |
| 18/335223 (AS) | 3'-UUC<u>AUU</u>CCUGGUCUCUGUUU-P 5' | (PS) |
| 19/335224 (AS) | 3'-UUCAUU<u>CC</u>UGGUCUCUGUUU-P 5' | (PS) |
| 20/335225 (AS) | 3'-UUCAUUCC<u>UGG</u>UCUCUGUUU-P 5' | (PS) |
| 21/335226 (AS) | 3'-UUCAUUCCUGGU<u>CUC</u>UGUUU-P 5' | (PS) |
| 22/335227 (AS) | 3'-UUCAUUCCUGGUCUC<u>UGU</u>UU-P 5' | (PS) |
| 23/335228 (AS) | 3'-UUCAUUCCUGGUCUCUG<u>UUU</u>-P 5' | (PS) |

| SEQ ID NO: | Sequence (5'-3') |
|---|---|
| 15 | AAGUAAGGACCAGAGACAAA |
| 16 | UUUGUCUCUGGUCCUUACUU |

The constructs were assayed for activity for measuring the levels of PTEN mRNA in T24 cells against untreated control levels. All of the asRNA's and siRNA's showed activity with the asRNA's having the best activity in each case. A clear dose response was seen for all the siRNA constructs (20, 40, 80 and 150 nm doses). There was a good dose response for the asRNA's for 50, 100 and 200 nm doses. In general the siRNA's were more active in this system at lower doses than the asRNA's and at the 150 nm dose was able to reduce PTEN mRNA levels to from 15 to 40% of untreated control. The unmodified siRNA 303912 reduced PTEN mRNA levels to about 19% of the untreated control.

EXAMPLE 33

3'-Hemimer 2'-O-methyl siRNA Constructs

Blunt and overhanging siRNA constructs were prepared having a block of 5, 2'-O-methyl nucleosides at the 3'-terminus.

| SEQ ID NO:/ISIS NO | Sequence (overhangs) |
|---|---|
| 7/271790 (S) | 5'-CAAAUCCAGAGGCUAGCAG-dTdT-3' |
| 24/xxxxxx (AS) | 3'-UUGUUUAGGUCUCCGA<u>UCGUC</u>-5' |

| SEQ ID NO:/ISIS NO | Sequence (blunt) |
|---|---|
| 25/xxxxx (S) | 5'-GUCAAAUCCAGAGGCUAGCAG-3' |
| 26/xxxxxx (AS) | 3'-CAGUUUAGGUCUCCGA<u>UCGUC</u>-5' |

Underlined nucleosides are 2'-O-methyl modified nucleosides, all other nucleosides are ribonucleosides and all internucleoside linkages for the AS strands are phosphorothioate and the internucleoside linkages for the S strand are phosphodiester.

| SEQ ID NO: | Sequence (5'-3') |
|---|---|
| 25 | GUCAAAUCCAGAGGCUAGCAG |
| 27 | CUGCUAGCCUCUGGAUUUGAC |

The construct having overhangs was able to reduce PTEN mRNA levels to about 36% of untreated control whereas the blunt ended construct was able to reduce the PTEN mRNA levels to about 27% of untreated control.

EXAMPLE 34 siRNA Hemimer Constructs

Three siRNA hemimer constructs were prepared and examined in a PTEN assay. The hemimer constructs had 7, 2'-O-methyl nucleosides at the 3'-end. The hemimer was put in the sense strand only, the antisense strand only and in both strands to compare the effects.

| SEQ ID NO:/ISIS NO | Constructs (overhangs) |
|---|---|
| 28/271068 (S) | 5'-CAAAUCCAGAGGCU<u>AGCAGUU</u>-3' |
| 29/ (AS) | 3'-<u>UUGUUUA</u>GGUCUCCGAUCGUC-5' |
| 28/271068 (S) | 5'-CAAAUCCAGAGGCU<u>AGCAGUU</u>-3' |
| 30/ (AS) | 3'-UUGUUUAGGUCUCCGAUCGUC-5' |
| 31/ (S) | 5'-CAAAUCCAGAGGCUAGCAGUU-3' |
| 29/ (AS) | 3'-<u>UUGUUUA</u>GGUCUCCGAUCGUC-5' |

Underlined nucleosides are 2'-O-methyl modified nucleosides, all other nucleosides are ribonucleosides and all internucleoside linkages for the AS strands are phosphorothioate and the internucleoside linkages for the S strand are phosphodiester.

| SEQ ID NO: | Sequence (5'-3') |
|---|---|
| 31 | CAAAUCCAGAGGCUAGCAGUU |
| 35 | |

The construct having the 7, 2'-O-methyl nucleosides only in the antisense strand reduced PTEN mRNA levels to about 23% of untreated control. The construct having the 7, 2'-O-methyl nucleosides in both strands reduced the PTEN mRNA levels to about 25% of untreated control. When the 7, 2'-O-methyl nucleosides were only in the sense strand PTEN mRNA levels were reduced to about 31% of untreated control.

EXAMPLE 35 siRNA vs asRNA Hemimers

Four hemimers were prepared and assayed as the asRNA's and also as the siRNA's in a PTEN assay. The unmodified sequence was also tested as the asRNA and as the siRNA.

| SEQ ID NO:/ISIS NO | Constructs (overhangs) |
|---|---|
| 15/308746 (S) | 5'-AAGUAAGGACCAGAGACAAA-3' |
| 16/303912 (AS) | 3'-UUCAUUCCUGGUCUCUGUUU-P 5' |
| 17/316449 (AS) | 3'-<u>UUC</u>AUUCCUGGUCUCUGUUU-P 5' |
| 32/319013 (AS) | 3'-<u>UUCA</u>UUCCUGGUCUCUGUUU-P 5' |
| 33/319014 (AS) | 3'-<u>UUCAU</u>UCCUGGUCUCUGUUU-P 5' |
| 34/319015 (AS) | 3'-<u>UUCAUU</u>CCUGGUCUCUGUUU-P 5' |

Underlined nucleosides are 2'-O-methyl modified nucleosides, all other nucleosides are ribonucleosides and all internucleoside linkages for the AS strands are phosphorothioate and the internucleoside linkages for the S strand are phosphodiester.

| Construct | siRNA (% mRNA) | asRNA (% mRNA) |
|---|---|---|
| 11/303912 | 21 | 32 |
| 11/316449 | 17 | 26 |
| 11/319013 | 34 | 32 |
| 11/319014 | 54 | 42 |
| 11/319015 | 51 | 42 |

Percent mRNA is relative to untreated control in PTEN assay.

EXAMPLE 36

Representative siRNA's Prepared Having 2'O—Me Gapmers

The following antisense strands of siRNA's were hybridized to the complementary full phosphodiester sense strand. Bolded monomers are 2'-OMe containing monomers. Underlined monomers have PS linkages. Monomers without underlines have PO linkages.

| SEQ ID NO/ISIS NO | Sequence | |
|---|---|---|
| 35/300852 | 5'-OH-CUG CUA GCC UCU GGA UUU GA | (OMe/PO) |
| 35/300853 | 5'-P- CUG CUA GCC UCU GGA UUU GA | (OMe/PO) |
| 36/300854 | 5'-OH-CUG CUA GCC UCU GGA UUU GA | (OMe/PO) |
| 37/300855 | 5'-P- C<u>UG</u> <u>CUA</u> GCC UCU GGA UU<u>U</u> <u>GA</u> | (OMe/PO/<u>PS</u>) |
| 38/300856 | 5'OH- <u>CUA</u> GCC UCU GGA UU<u>U</u> <u>GA</u> | (OMe/PO/<u>PS</u>) |
| 39/300858 | 5'-OH-C<u>UG</u> <u>CUA</u> G<u>CC</u> <u>UCU</u> <u>GGA</u> <u>UUU</u> <u>GA</u> | (OMe/<u>PS</u>) |
| 39/300859 | 5'-P- C<u>UG</u> <u>CUA</u> G<u>CC</u> <u>UCU</u> <u>GGA</u> <u>UUU</u> <u>GA</u> | (OMe/<u>PS</u>) |
| 40/300860 | 5'-OH-<u>CUA</u> G<u>CC</u> <u>UCU</u> <u>GGA</u> <u>UUU</u> <u>GA</u> | (OMe/<u>PS</u>) |
| 41/303913 | 5'-OH-<u>GUC</u> <u>UCU</u> <u>GGU</u> <u>CCU</u> <u>UAC</u> <u>UU</u> | (OMe/<u>PS</u>) |
| 42/303915 | 5'-OH-<u>UUU</u> <u>UGU</u> <u>CUC</u> <u>UGG</u> <u>UCC</u> <u>UU</u> | (OMe/<u>PS</u>) |
| 43/303917 | 5'-OH-<u>CUG</u> <u>GUC</u> <u>CUU</u> <u>ACU</u> <u>UCC</u> <u>CC</u> | (OMe/PS) |
| 44/308743 | 5'P- <u>UUU</u> <u>GUC</u> <u>UCU</u> <u>GGU</u> <u>CCU</u> <u>UAC</u> <u>UU</u> | (OMe/<u>PS</u>) |
| 45/308744 | 5'-P- <u>UCU</u> <u>CUG</u> <u>GUC</u> <u>CUU</u> <u>ACU</u> <u>UCC</u> <u>CC</u> | (OMe/<u>PS</u>) |
| 46/328795 | 5'-P- <u>UUU</u> <u>GUC</u> <u>UCU</u> <u>GGU</u> <u>CCU</u> <u>UAC</u> <u>UU</u> | (OMe/<u>PS</u>) |

EXAMPLE 38

Representative siRNA's Prepared Having 2'-F-methyl Modified Nucleosides and Various Structural Motifs The following antisense strands of siRNA's were hybridized to the complementary full phosphodiester sense strand. Bolded monomers are 2'-F containing monomers. Underlined monomers have PS linkages. Monomers without underlines have PO linkages. Sense stands (S) are listed 3' ->5'. Antisense strands (AS) are listed 5' ->3'.

| SEQ ID NO/ISIS NO | Sequence | Features |
|---|---|---|
| 47/279471 AS | $^m$CUG $^m$CUA G$^m$C$^m$C U$^m$CU GGA UUU G dTdT | (F/PO) |
| 48/279467 S | $^m$CAA AU$^m$C $^m$CAG AGG $^m$CUA G$^m$CA G dTdT | (F/PO) |
| 49/319018 AS | UU UGU CUC UGG UCC UUA CUU | (F/PO) |
| 50/319019 S | AAG UAA GGA CCA GAG ACA AA | (F/PO) |
| 51/319022 AS | <u>UU</u> <u>UGU</u> <u>CUC</u> <u>UGG</u> <u>UCC</u> <u>UUA</u> <u>CUU</u> | (F/<u>PS</u>) |

-continued

| SEQ ID NO/ISIS NO | Sequence | Features |
|---|---|---|
| 52/333749 AS | UU UGU CUC UGG UCC UUA CUU | (F/OH/PS) |
| 53/333750 AS | UU UGU CUC UGG UCC UUA CUU | (F/OH/PS) |
| 53/333751 AS | UU UGU CUC UGG UCC UUA CUU | (F/OH/PS) |
| 54/333752 AS | UU UGU CUC UGG UCC UUA CUU | (F/OH/PS) |
| 55/333753 AS | UU UGU CUC UGG UCC UUA CUU | (F/OH/PS) |
| 56/333754 AS | UU UGU CUC UGG UCC UUA CUU | (F/OH/PS) |
| 57/333756 AS | UU UGU CUC UGG UCC UUA CUU | (F/OH/PS) |
| 58/334253 AS | UU UGU CUC UGG UCC UUA CUU | (F/OH/PS) |
| 59/334254 AS | UU UGU CUC UGG UCC UUA CUU | (F/OH/PS) |
| 60/334255 AS | UU UGU CUC UGG UCC UUA CUU | (F/OH/PS) |
| 61/334256 AS | UU UGU CUC UGG UCC UUA CUU | (F/OH/PS) |
| 62/334257 AS | UU UGU CUC UGG UCC UUA CUU | (F/OH/PS) |
| 63/317466 AS | UUU GUC UCU GGU CCU UAC UU | PS |
| 64/317468 AS | UUU GUC UCU GGU CCU UAC UU | PO |
| 65/317502 AS | UUU GUC UCU GGU CCU UAC UU | PS |

Results from a PTEN assay are presented below. Percent mRNA is relative to control in PTEN assay.

| | % mRNA | |
|---|---|---|
| Construct | 100 nM asRNA | 100 nM siRNA |
| 303912 | 35 | 18 |
| 317466 | — | 28 |
| 317408 | — | 18 |
| 317502 | — | 21 |
| 334254 | — | 33 |
| 333756 | 42 | 19 |
| 334257 | 34 | 23 |
| 334255 | 44 | 21 |

-continued

| | % mRNA | |
|---|---|---|
| Construct | 100 nM asRNA | 100 nM siRNA |
| 333752 | 42 | 18 |
| 334253 | 38 | 15 |
| 333750 | 43 | 21 |
| 333749 | 34 | 21 |

EXAMPLE 39

Representative siRNA's Prepared Having 2'-F and 2'-OMe Modified Nucleosides

The following antisense strands of siRNA's were hybridized to the complementary full phosphodiester sense strand. Where the antisense strand has a TT 3'-terminus the corresponding sense strand also has a 3'-TT (deoxyT's). Bolded monomers are 2'-F containing monomers. Underlined monomers are 2'-OMe. Monomers that are not bolded or underlined do not contain a sugar surrogate. Linkages are shown in the parenthesis after the sequence.

| SEQ ID NO./ISIS NO. | Composition (5' 3') | Features |
|---|---|---|
| 66/283546 | CUG CUA GCC UCU GGA UUU GU.dT-3' | (OMe/F/PO) |
| 67/336240 | UUU GUC UCU GGU CCU UAC UU | (OMe/F/PS) |

EXAMPLE 39

Representative siRNA's Prepared Having 2'-MOE Modified Nucleosides Assayed for PTEN mRNA Levels Against Untreated Control The following antisense strands of siRNA's were hybridized to the complementary full phosphodiester sense strand. Bolded monomers are 2'-MOE (2'-methoxyethoxy). Linkages are phosphothioate.

| SEQ ID NO | Composition | PTEN mRNA level (% UTC) 100 nM oligomer |
|---|---|---|
| 68 | UUC AUU CCU GGU CUC UGU UU | — |
| 69 | UUC AUU CCU GGU CUC UGU UU | 50 |
| 70 | UUC AUU CCU GGU CUC UGU UU | — |
| 71 | UUC AUU CCU GGU CUC UGU UU | 43 |
| 72 | UUC AUU CCU GGU CUC UGU UU | 42 |
| 73 | UUC AUU CCU GGU CUC UGU UU | 47 |
| 74 | UUC AUU CCU GGU CUC UGU UU | 63 |
| 75 | UUC AUU CCU GGU CUC UGU UU | 106 |

What is claimed is:

1. A composition comprising a duplex consisting of a first chemically synthesized oligonucleotide and a second chemically synthesized oligonucleotide, wherein:
- each of the first chemically synthesized oligonucleotide and the second chemically synthesized oligonucleotide independently consists of 17 to 25 linked nucleosides, each nucleoside comprising a nucleobase and a sugar;
- the first chemically synthesized oligonucleotide is 100% complementary to the second chemically synthesized oligonucleotide and to a target mRNA;
- the first chemically synthesized oligonucleotide and the second chemically synthesized oligonucleotide are not covalently linked to each other; and
- the first chemically synthesized oligonucleotide is a gapmer, wherein the gap comprises at least 4 nucleosides, each comprising a 2'-hydroxy-pentofuranosyl sugar moiety, and wherein each nucleoside of each wing comprises a 2'-sugar modification; and
- the second chemically synthesized oligonucleotide comprises at least one nucleoside that comprises a 2'-sugar modification.

2. The composition of claim 1, wherein the second chemically synthesized oligonucleotide is a gapmer, wherein the gap comprises at least 4 nucleosides, each comprising a 2'-hydroxyl pentofuranosyl sugar moiety, and wherein each nucleoside of each wing comprises a 2' modification.

3. The composition of claim 1, wherein each nucleoside of at least one of the wings of the gapmer comprises a 2' sugar modification selected from fluoro, alkoxy, amino-alkoxy, allyloxy, imidazolylalkoxy, and methoxyethoxy.

4. The composition of claim 1, wherein each nucleoside of the 3' wing of the gapmer comprises a 2'-$OCH_3$.

5. The composition of claim 1, wherein each wing of the gapmer is from two to seven nucleosides in length.

6. The composition of claim 1, wherein at least one of the first chemically synthesized oligonucleotide and the second chemically synthesized oligonucleotide comprises at least one phosphorothioate linkage.

7. The composition of claim 6, wherein each of the first chemically synthesized oligonucleotide and the second chemically synthesized oligonucleotide comprises at least one phosphorothioate linkage.

\* \* \* \* \*